United States Patent [19]

Tsuji et al.

[11] Patent Number: 5,112,998

[45] Date of Patent: May 12, 1992

[54] PREGNANE DERIVATIVES AND PROCESSES FOR PRODUCTION THEREOF

[75] Inventors: Jiro Tsuji, Okayama; Takashi Takahashi, Tokyo; Masao Tsuji, Okayama; Naoshi Nakagawa, Okayama; Tetsuo Takigawa, Okayama, all of Japan

[73] Assignee: Kuraray Co., Ltd., Kurashiki, Japan

[21] Appl. No.: 545,120

[22] Filed: Jun. 15, 1990

Related U.S. Application Data

[63] Continuation of Ser. No. 283,927, filed as PCT/JP88/00313, Mar. 29, 1988, abandoned.

[30] Foreign Application Priority Data

| Mar. 30, 1987 | [JP] | Japan | 62-77849 |
| Mar. 30, 1987 | [JP] | Japan | 62-77850 |
| Mar. 30, 1987 | [JP] | Japan | 62-77851 |
| Mar. 31, 1987 | [JP] | Japan | 62-80588 |
| Mar. 31, 1987 | [JP] | Japan | 62-80589 |

[51] Int. Cl.$^5$ .............................. C07J 21/00; C07J 9/00
[52] U.S. Cl. .................................... 552/559; 552/560; 552/562; 552/580; 552/582; 552/583
[58] Field of Search .............. 552/586, 587, 610, 636, 552/553, 559, 560, 582, 583, 562

[56] References Cited

U.S. PATENT DOCUMENTS 4,193,921  3/1980  Furst .
4,310,467  1/1982  Batcho et al. ............. 552/501

FOREIGN PATENT DOCUMENTS 0084199   7/1983  European Pat. Off. ......... 552/501
2547119   5/1976  Fed. Rep. of Germany ..... 552/501
53-50152  5/1978  Japan .

Primary Examiner—Asok Pal
Assistant Examiner—P. Achutamurthy
Attorney, Agent, or Firm—Oblon, Spivak, McClelland, Maier & Neustadt

[57] ABSTRACT

There are provided pregnane derivatives represented by formula

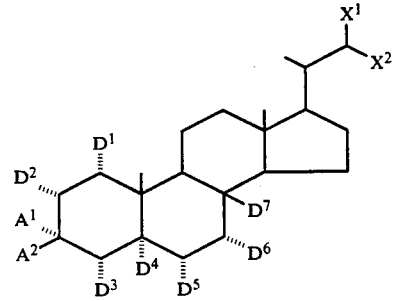

wherein $A^1$ represents a hydrogen atom or a hydroxyl group, $A^2$ represents a substituent such as a hydroxyl group when $A^1$ represents a hydrogen atom, or $A^2$ represents a hydrogen atom when $A^1$ represents a hydroxyl group, or $A^1$ and $A^2$ are combined together to form an oxo group; $D^1$ represents a substitutent such as a hydroxyl group, and $D^2$ represents a hydrogen atom, or $D^1$ and $D^2$ are combined together to form an epoxy group or a single bond; $D^3$, $D^5$ and $D^7$ each represents a hydrogen atom, $D^4$ represents a hydroxyl group, and $D^6$ represents a substitutent such as a hydroxyl group, or $D^3$ and $D^4$ may be combined together to form an epoxy group or a single bond, or $D^4$ and $D^5$ may be combined together to form a single bond, or $D^5$ and $D^6$ may be combined together to form an epoxy group or a single bond, or $D^6$ and $D^7$ may be combined together to form a singel bond; and $X^1$ and $X^2$ each represents a lower alkoxyl group or, when combined together, they represent a lower alkylenedioxy or oxo group, and a process for their preparation.

The pregnane derivatives are useful as intermediates for synthesizing vitamin $D_3$ derivatives having a hydroxyl group in the 1α-position.

10 Claims, No Drawings

PREGNANE DERIVATIVES AND PROCESSES FOR PRODUCTION THEREOF

This application is a continuation of application Ser. No. 07/283,927, filed on Nov. 30, 1988, now abandoned.

TECHNICAL FIELD

The present invention relates to novel pregnane derivatives and to processes for producing the same.

The pregnane derivatives according to the invention are of value as synthetic intermediates for the production of vitamin $D_3$ derivatives having a hydroxy group in the 1α-position, such as 1α-hydroxy-vitamin $D_3$, which are known to be effective in the treatment of disorders of calcium metabolism such as chronic renal failure, dysparathyroidism, osteomalacia, osteoporosis and so on.

BACKGROUND ART

The hitherto-known processes for producing vitamin $D_3$ derivatives having a hydroxy group in the 1α-position include, for example, the process for producing 1α-hydroxy-vitamin $D_3$ using cholesterol as a starting material (Japanese Patent Application Laid-open No. 48-62750 and No. 49-95956), the process for producing 1α, 25-dihydroxy-vitamin $D_3$ using cholesta-1,5,7-trien-3-on-25-ol derived from cholesta-1,4,6-trien-3-on-25-ol as a synthetic intermediate (Japanese Patent Application Laid-open No. 51-100056), and the process for producing (24R)-1α,24,25-trihydroxy-vitamin $D_3$ by subjecting (24R)-1α,3β,24,25-tetrahydroxycholesta-5,7-diene to ultraviolet irradiation in an inert organic solvent and, then, isomerizing the resulting (24R)-1α, 24, 25-trihydroxy-previtamin $D_3$ (Japanese Patent Application Laid-open No. 51-108046). It is also known that certain pregnane derivatives, such as (20S)-1α,3β-diacetoxypregn-5-ene-20-carbaldehyde, etc., which are derived from (20S)-21-hydroxy-20-methyl-6β-methoxy-3α,5-cyclo-5α-pregnane, (20S)-21-hydroxy-20-methylpregna-1,4-dien-3-one, etc. by the processes shown below can be converted to 1α,25-dihydroxy-vitamin $D_3$ and other compounds (Japanese Patent Application Laid-open No. 53-50152).

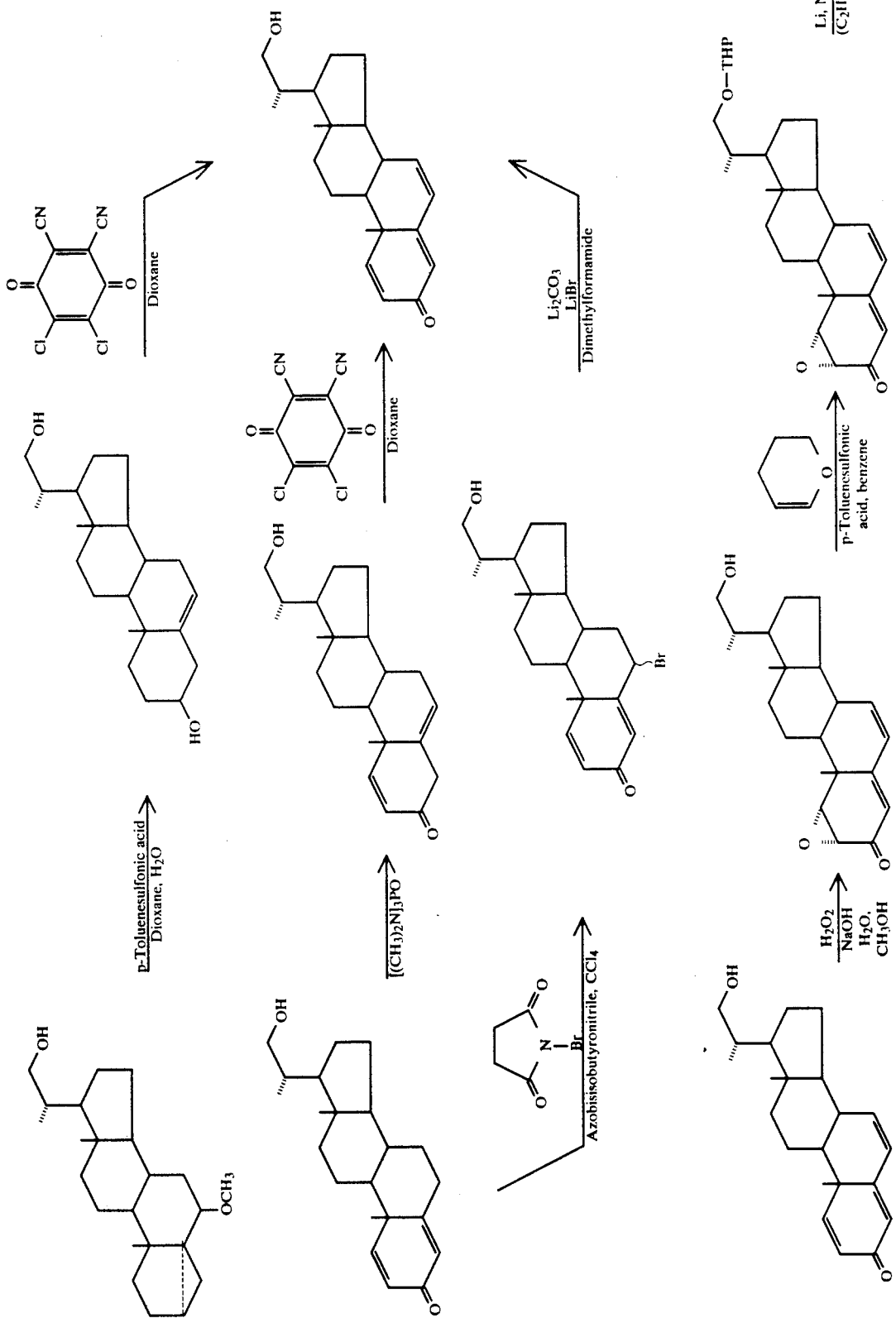

-continued
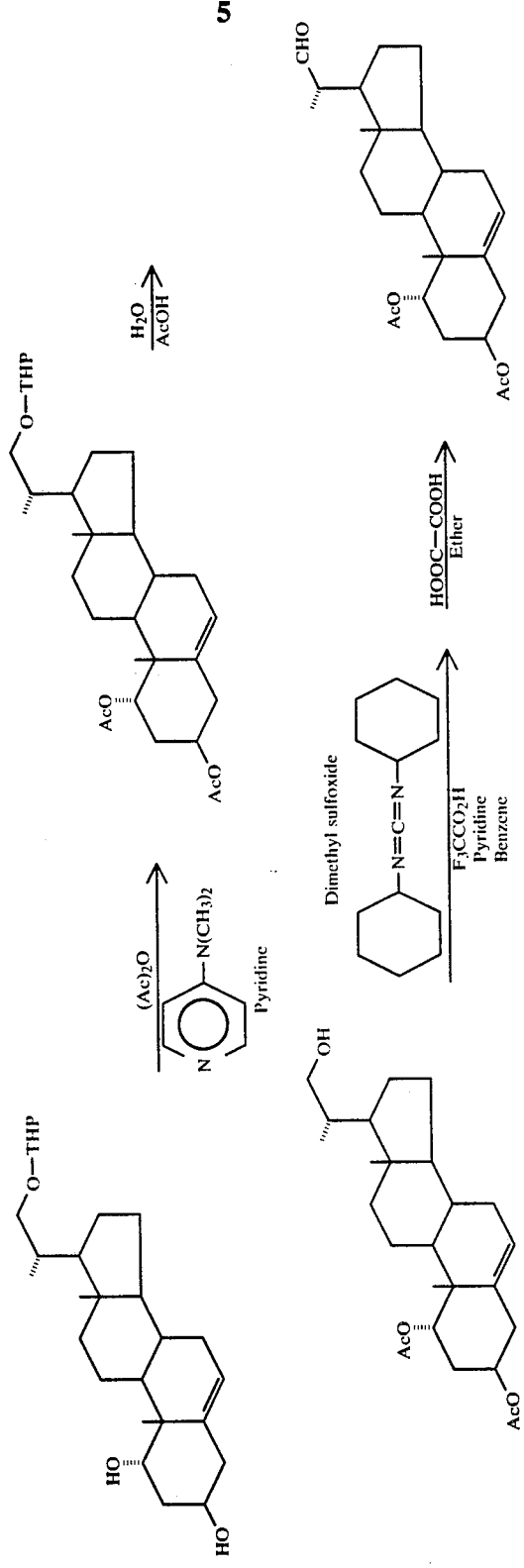

In the above formulas, THP is a 2-tetrahydropyranyl group; Ac is an acetyl group; the dotted line ( . . . ) indicates that the substituent is in the α-configuration; the solid line (—) indicates that the substituent is in the β-configuration; the wavy line (~) indicates that the substituent is either in the α-configuration or in the β-configuration.

There is also known a process by which 1α,25,26-trihydroxy-vitamin D$_3$ is synthesized from the aforementioned (20S)-1α,3β-diacetoxypregn-5-ene-20-carbaldehyde (Japanese Patent Application Laid-open No. 56-51447).

While a variety of processes are thus known for the production of vitamin D$_3$ derivatives having a hydroxy group in the 1α-position, it is obviously preferable that, in the production of such vitamin D$_3$ derivatives having a hydroxy group in the 1α-position, one have as many compounds as possible to choose from as synthetic intermediates, for one would then enjoy the utmost flexibility in selecting the optimum process sequence according to the availability of starting compounds.

It is, therefore, an object of the invention to provide novel compounds which can be converted to various vitamin D$_3$ derivatives having a hydroxy group in the 1α-position.

It is another object of the invention to provide processes for producing such novel compounds.

Disclosure of Invention

The aforementioned objects of the present invention are accomplished by providing pregnane derivatives of the following general formula

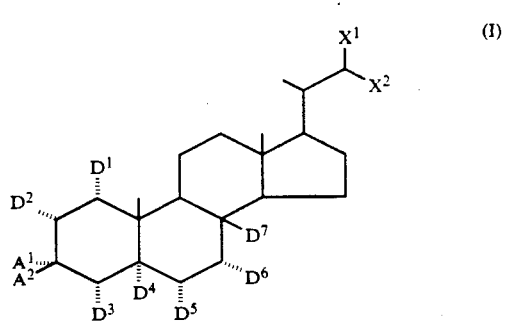

(I)

wherein $A^1$ is in the α-configuration and represents a hydrogen atom or a hydroxyl group, and $A^2$ is such that where $A^1$ is in the α-configuration and represents a hydrogen atom, $A^2$ is in the β-configuration and represents a hydroxyl group, an acyloxy group, a lower alkoxycarbonyloxy group, an N-lower alkylcarbamoyloxy group, an N-arylcarbamoyloxy group, an N,N-di(lower alkyl)carbamoyloxy group, a tri-substituted silyloxy group or an alkoxymethoxy group which may optionally be substituted and that where $A^1$ is in the α-configuration and represents a hydroxyl group, $A^2$ is in the β-configuration and represents a hydrogen atom, or $A^1$ and $A^2$ jointly represent an oxo group (=O); $D^1$ is in the α-configuration and represents a hydroxyl group, an acyloxy group, a lower alkoxycarbonyloxy group, an N-lower alkylcarbamoyloxy group, an N-arylcarbamoyloxy group, an N,N-di(lower alkyl)-carbamoyloxy group, a tri-substituted silyloxy group or an alkoxymethoxy group which may optionally be substituted, and $D^2$ is in the α-configuration and represents a hydrogen atom, or $D^1$ and $D^2$ jointly represent an epoxy group (—O—) which is in the α-configuration or a single bond; $D^3$ is in the α-configuration and represents a hydrogen atom, $D^4$ is in the α-configuration and represents a hydroxyl group, $D^5$ is in the α-configuration and represents a hydrogen atom, $D^6$ is in the α-configuration and represents a hydroxyl group, a lower alkoxycarbonyloxy group, an acyloxy group, an N-lower alkylcarbamoyloxy group, an N-arylcarbamoyloxy group or an N,N-di(lower alkyl)carbamoyloxy group, $D^7$ is in the β-configuration and represents a hydrogen atom; provided that $D^3$ and $D^4$ may jointly represent an epoxy group (—O—) which is in the α-configuration or a single bond, $D^4$ and $D^5$ may jointly represent a single bond, $D^5$ and $D^6$ may jointly represent an epoxy group (—O—) which is in the α-configuration or a single bond, and $D^6$ and $D^7$ may jointly represent a single bond; and $X^1$ and $X^2$ each is a lower alkoxyl group or jointly represent a lower alkylenedioxy group or an oxo group (=O); and the production processes described hereinafter under (1) through (5).

(1) A process for producing a 7α-hydroxypregna-1,4-dien-3-one-20-carbaldehyde characterized by cultivating a microbe of the genus Alcaligenes which is capable of producing 7α-hydroxypregna-1,4-dien-3-one-20-carbaldehyde by utilizing 3α,7α-dihydroxy-5β-cholanic acid and/or a salt thereof as a substrate, in a medium containing 3α,7α-dihydroxy-5β-cholanic acid and/or a salt thereof.

(2) A process for producing a pregnane derivative of the general formula

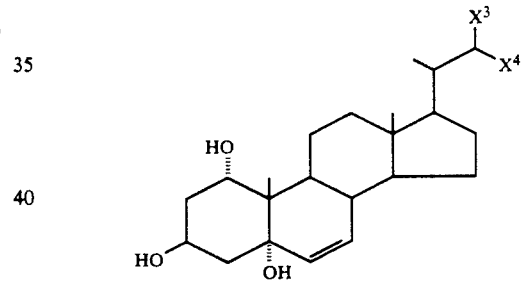

wherein $X^3$ and $X^4$ have the meanings defined hereinafter, characterized by reducing a pregnane derivative of the general formula

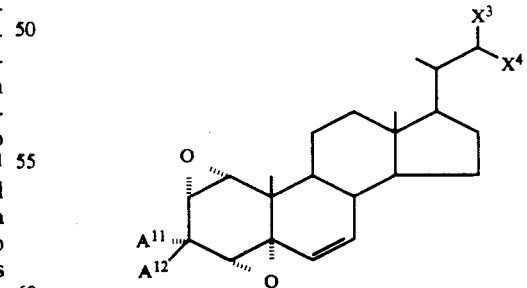

wherein $A^{11}$ is in the α-configuration and represents a hydrogen atom and $A^{12}$ is in the β-configuration and represents a hydroxyl group, an acyloxy group, a lower alkoxycarbonyloxy group, an N-lower alkylcarbamoyloxy group, an N-arylcarbamoyloxy group or an N,N-di(lower alkyl)carbamoyloxy group, or $A^{11}$ and $A^{12}$ jointly represent an oxo group (=O); and $X^3$ and $X^4$ each is a lower alkoxyl group or jointly represent a lower alkylenedioxy group.

(3) A process for producing a pregnane derivative of the general formula

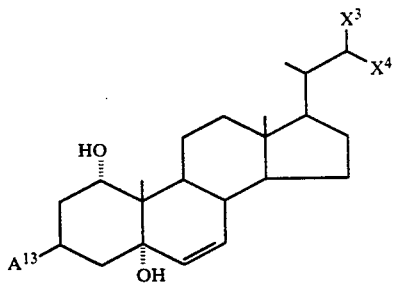

wherein $A^{13}$, $X^3$ and $X^4$ have the meanings defined hereinafter, characterized by reducing a pregnane derivative of the general formula

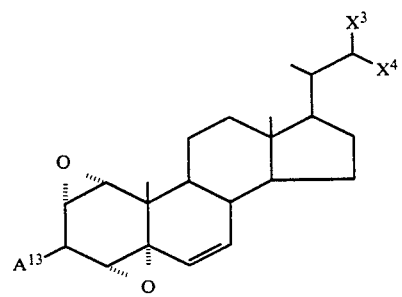

wherein $A^{13}$ is in the $\beta$-configuration and represents a tri-substituted silyloxy group or an alkoxymethoxy group which may optionally be substituted; $X^3$ and $X^4$ have the meanings defined hereinbefore.

(4) A process for producing a pregnane derivative of the general formula

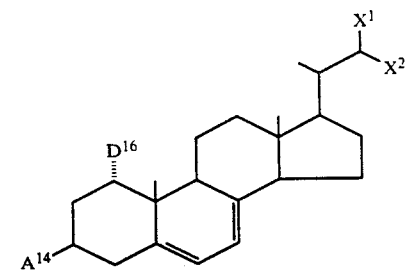

wherein $A^{14}$, $D^{16}$, $X^1$ and $X^2$ have the meanings defined hereinafter, characterized in that a pregnane derivative of the general formula

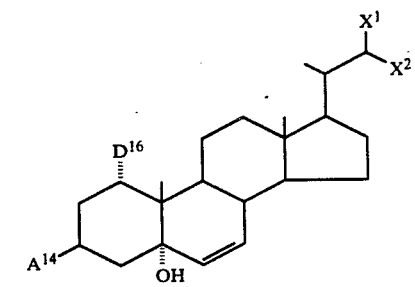

wherein $A^{14}$ is in the $\beta$-configuration and represents a hydroxyl group, an acyloxy group, a lower alkoxycarbonyloxy group, an N-lower alkylcarbamoyloxy group, an N-arylcarbamoyloxy group, an N,N-di(lower alkyl)-carbamoyloxy group, a tri-substituted silyloxy group or an alkoxymethoxy group which may optionally be substituted; $D^{16}$ is in the $\alpha$-configuration and represents a hydroxyl group, an acyloxy group, a lower alkoxycarbonyloxy group, an N-lower alkylcarbamoyloxy group, an N-arylcarbamoyloxy group, an N,N-di(lower alkyl)-carbamoyloxy group, a tri-substituted silyloxy group or an alkoxymethoxy group which may optionally be substituted; $X^1$ and $X^2$ have the meanings defined hereinbefore, is subjected to dehydration reaction.

(5) A process for producing a pregnane derivative of the general formula

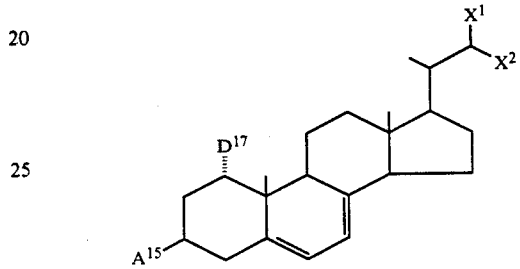

wherein $A^{15}$, $A^{17}$, $X^1$ and $X^2$ have the meanings defined hereinafter, characterized in that a pregnane derivative of the general formula

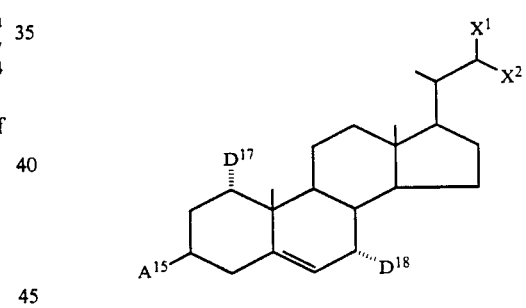

wherein $A^{15}$ is in the $\beta$-configuration and represents a hydroxyl group, an acyloxy group, a lower alkoxycarbonyloxy group, an N-lower alkylcarbamoyloxy group, an N-arylcarbamoyloxy group, an N,N-di(lower alkyl)-carbamoyloxy group, a tri-substituted silyloxy group or an alkoxymethoxy group which may optionally be substituted; $D^{17}$ is in the $\alpha$-configuration and represents a hydroxyl group, an acyloxy group, a lower alkoxycarbonyloxy group, an N-lower alkylcarbamoyloxy group, an N-arylcarbamoyloxy group, an N,N-di(lower alkyl)-carbamoyloxy group, a tri-substituted silyloxy group or a lower alkoxymethoxy group; $D^{18}$ is in the $\alpha$-configuration and represents an acyloxy group, a lower alkoxycarbonyloxy group, an N-lower alkylcarbamoyloxy group, an N-arylcarbamoyloxy group or an N,N-di(lower alkyl)carbamoyloxy group; $X^1$ and $X^2$ have the meanings defined hereinbefore, is caused to react in the presence of a palladium compound.

The pregnane derivatives of general formula (I) which are provided by the present invention can be roughly grouped into a class of pregnane derivatives of the general formula

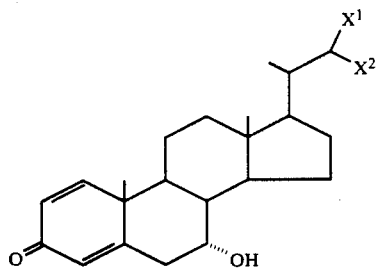

wherein $X^1$ and $X^2$ have the meanings defined hereinbefore (which compounds will hereinafter be referred to sometimes as pregnane derivative (I-1)); a class of pregnane derivatives of the general formula

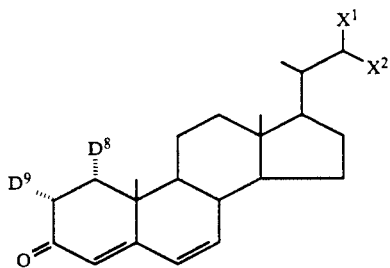

wherein $D^8$ and $D^9$ jointly represent an epoxy group (—O—) which is in the α-configuration or a single bond, and $X^1$ and $X^2$ have the meanings defined hereinbefore (which compounds will hereinafter be referred to sometimes as pregnane derivative (I-2)); a class of pregnane derivatives of the general formula

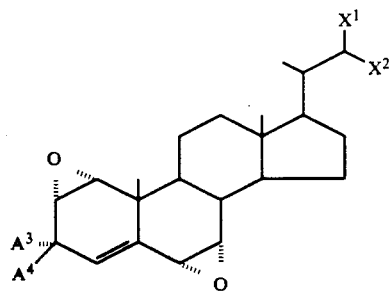

wherein $A^3$ is in the α-configuration and represents a hydrogen atom, $A^4$ is in the β-configuration and represents a hydroxyl group or a lower alkanoyloxy group, or $A^3$ and $A^4$ jointly represent an oxo group (=O); and $X^1$ and $X^2$ have the meanings defined hereinbefore (which compounds will hereinafter be referred to sometimes as pregnane derivative (I-3)); a class of pregnane derivatives of the general formula

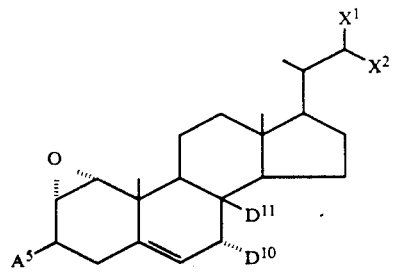

wherein $A^5$ is in the β-configuration and represents a hydroxyl group or a lower alkanoyloxy group; $D^{10}$ is in the α-configuration and represents a hydroxyl group, a lower alkoxycarbonyloxy group, a lower alkanoyloxy group, an N-lower alkylcarbamoyloxy group, an N-arylcarbamoyloxy group or an N,N-di(lower alkyl)carbamoyloxy group, and $D^{11}$ is in the β-configuration and represents a hydrogen atom, or $D^{10}$ and $D^{11}$ jointly represent a single bond; and $X^1$ and $X^2$ have the meanings defined hereinbefore (which compounds will hereinafter be referred to sometimes as pregnane derivative (I-4)); a class of pregnane derivatives of the general formula (I-5)

wherein $A^6$ is in the β-configuration and represents a hydroxyl group, an acyloxy group, a lower alkoxycarbonyloxy group, an N-lower alkylcarbamoyloxy group, an N-arylcarbamoyloxy group, an N,N-di(lower alkyl)-carbamoyloxy group, a tri-substituted silyloxy group or an alkoxymethoxy group which may optionally be substituted; $D^{12}$ is in the α-configuration and represents a hydroxyl group, an acyloxy group, a lower alkoxycarbonyloxy group, an N-lower alkylcarbamoyloxy group, an N-arylcarbamoyloxy group, an N,N-di(lower alkyl)-carbamoyloxy group, a tri-substituted silyloxy group or an alkoxymethoxy group which may optionally be substituted; and $X^1$ and $X^2$ have the meanings defined hereinbefore (which compounds will hereinafter be referred to sometimes as pregnane derivative (I-5)); a class of pregnane derivatives of the general formula (I-6)

wherein $X^1$ and $X^2$ have the meanings defined hereinbefore (which compounds will hereinafter be referred to sometimes as pregnane derivative (I-6)); a class of pregnane derivatives of the general formula

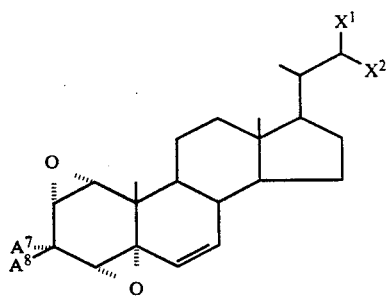
(I-7)

wherein $A^7$ is in the α-configuration and represents a hydrogen atom or a hydroxyl group, and $A^8$ is such that where $A^7$ is a hydrogen atom in the α-configuration, $A^8$ is in the β-configuration and represents a hydroxyl group, an acyloxy group, a lower alkoxycarbonyloxy group, an N-lower alkylcarbamoyloxy group, an N-arylcarbamoyloxy group, an N,N-di(lower alkyl)carbamoyloxy group, a tri-substituted silyloxy group or an alkoxymethoxy group which may optionally be substituted and where $A^7$ is a hydroxyl group in the α-configuration, $A^8$ is in the β-configuration and represents a hydrogen atom, or $A^7$ and $A^8$ jointly represent an oxo group (=O); and $X^1$ and $X^2$ have the meanings defined hereinbefore (which compounds will hereinafter be referred to sometimes as pregnane derivative (I-7)); a class of pregnane derivatives of the general formula

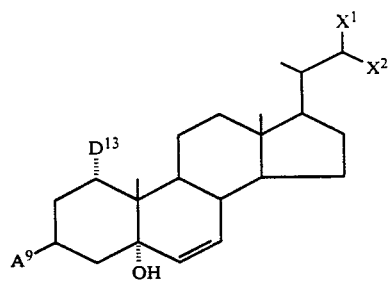
(I-8)

wherein $A^9$ is in the β-configuration and represents a hydroxyl group, an acyloxy group, a lower alkoxycarbonyloxy group, an N-lower alkylcarbamoyloxy group, an N-arylcarbamoyloxy group, an N,N-di(lower alkyl)carbamoyloxy group, a tri-substituted silyloxy group or an alkoxymethoxy group which may optionally be substituted; $D^{13}$ is in the α-configuration and represents a hydroxyl group, an acyloxy group, a lower alkoxycarbonyloxy group, an N-lower alkylcarbamoyloxy group, an N-arylcarbamoyloxy group, an N,N-di(lower alkyl)carbamoyloxy group, a tri-substituted silyloxy group or an alkoxymethoxy group which may optionally be substituted; and $X^1$ and $X^2$ have the meanings defined hereinbefore (which compounds will hereinafter be referred to sometimes as pregnane derivative (I-8)); and a class of pregnane derivatives of the general formula

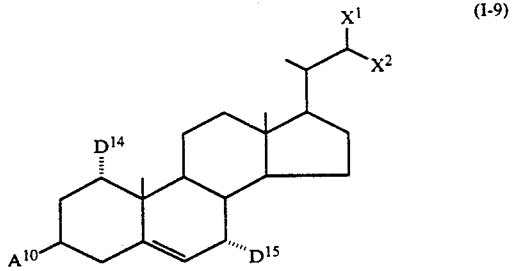
(I-9)

wherein $A^{10}$ is in the β-configuration and represents a hydroxyl group, an acyloxy group, a lower alkoxycarbonyloxy group, an N-lower alkylcarbamoyloxy group, an N-arylcarbamoyloxy group, an N,N-di(lower alkyl)carbamoyloxy group, a tri-substituted silyloxy group or an alkoxymethoxy group which may optionally be substituted; $D^{14}$ is in the α-configuration and represents a hydroxyl group, an acyloxy group, a lower alkoxycarbonyloxy group, an N-lower alkylcarbamoyloxy group, an N-arylcarbamoyloxy group, an N,N-di(lower alkyl)carbamoyloxy group, a tri-substituted silyloxy group or an alkoxymethoxy group which may optionally be substituted; $D^{15}$ is in the α-configuration and represents a hydroxyl group, an acyloxy group, a lower alkoxycarbonyloxy group, an N-lower alkylcarbamoyloxy group, an N-arylcarbamoyloxy group or an N,N-di(lower alkyl)carbamoyloxy group; and $X^1$ and $X^2$ have the meanings defined hereinbefore (which compounds will hereinafter be referred to sometimes as pregnane derivative (I-9)).

Referring to the above general formulas, $A^2$, $A^4$, $A^5$, $A^6$, $A^8$, $A^9$, $A^{10}$, $A^{12}$, $A^{13}$, $A^{14}$, $A^{15}$, $D^1$, $D^6$, $D^{10}$, $D^{12}$, $D^{13}$, $D^{14}$, $D^{15}$, $D^{16}$, $D^{17}$, $D^{18}$, $X^1$, $X^2$, $X^3$ and $X^4$ are explained in detail below.

The acyloxy group represented by $A^2$, $A^6$, $A^8$, $A^9$, $A^{10}$, $A^{12}$, $A^{14}$, $A^{15}$, $D^1$, $D^6$, $D^{12}$, $D^{13}$, $D^{14}$, $D^{15}$, $D^{16}$, $D^{17}$ or $D^{18}$ is exemplified by lower alkanoyloxy groups such as acetoxy, propionyloxy, butyryloxy, valeryloxy, etc. and aroyloxy groups such as benzoyloxy, methylbenzoyloxy, naphthoyloxy and so on. The lower alkanoyloxy group represented by $A^4$, $A^5$ or $D^{10}$ is exemplified by acetoxy, propionyloxy, butyryloxy, valeryloxy and so on. The lower alkoxycarbonyloxy group represented by $A^2$, $A^6$, $A^8$, $A^9$, $A^{10}$, $A^{12}$, $A^{14}$, $A^{15}$, $D^1$, $D^6$, $D^{10}$, $D^{12}$, $D^{13}$, $D^{14}$, $D^{15}$, $D^{16}$, $D^{17}$ or is exemplified by methoxycarbonyloxy, ethoxycarbonyloxy, propoxycarbonyloxy, butoxycarbonyloxy and so on. The N-lower alkylcarbamoyloxy group represented by $A^2$, $A^6$, $A^8$, $A^9$, $A^{10}$, $A^{12}$, $A^{14}$, $A^{15}$, $D^1$, $D^6$, $D^{10}$, $D^{12}$, $D^{13}$, $D^{14}$, $D^{15}$, $D^{16}$, $D^{17}$ or $D^{18}$ is exemplified by N-methylcarbamoyloxy, N-ethylcarbamoyloxy, N-propylcarbamoyloxy, N-butylcarbamoyloxy and so on. The N-arylcarbamoyloxy group represented by $A^2$, $A^6$, $A^8$, $A^9$, $A^{10}$, $A^{12}$, $A^{14}$, $A^{15}$, $D^1$, $D^6$, $D^{10}$, $D^{12}$, $D^{13}$, $D^{14}$, $D^{15}$, $D^{16}$, $D^{17}$ or $D^{18}$ is exemplified by N-phenylcarbamoyloxy, N-tolylcarbamoyloxy, N-naphthylcarbamoyloxy and so on. The N,N-di(lower alkyl)carbamoyloxy group represented by $A^2$, $A^6$, $A^8$, $A^9$, $A^{10}$, $A^{12}$, $A^{14}$, $A^{15}$, $D^1$, $D^6$, $D^{12}$, $D^{13}$, $D^{14}$, $D^{15}$, $D^{16}$ or $D^{17}$ is exemplified by N,N-di(methyl)carbamoyloxy, N,N-di(ethyl)carbamoyloxy, N,N-di(propyl)carbamoyloxy, N-ethyl-N-methylcarbamoyloxy and so on. The tri-substituted silyloxy group represented by $A^2$, $A^6$, $A^8$, $A^9$, $A^{10}$, $A^{13}$, $A^{14}$, $A^{15}$, $D^1$, $D^{12}$, $D^{13}$, $D^{14}$, $D^{16}$, $D^{17}$ or $D^{18}$ is exemplified by trimethylsilyloxy, t-butyldimethylsilyloxy, t-butyldiphenylsilyloxy, tripropylsilyloxy and so on. The alkoxymethoxy group which may optionally be substituted, which is represented by $A^2$, $A^6$, $A^8$, $A^9$, $A^{10}$, $A^{13}$, $A^{14}$, $A^{15}$, $D^1$, $D^{12}$, $D^{13}$, $D^{14}$, $D^{16}$ or $D^{17}$, is exemplified by methoxymethoxy, ethoxymethoxy, propoxymethoxy, butoxymethoxy, methoxyethoxymethoxy, tetrahydropyranyloxy, tetrahydrofuranyloxy, methoxyisopropyloxy and so on. The lower alkoxy group represented by $X^1$, $X^2$, $X^3$ or $X^4$ is exemplified by methoxy, ethoxy, propoxy, butoxy and so on. The lower alkylenedioxy group represented jointly by $X^1$ and $X^2$ and the lower alkylenedioxy group represented jointly by $X^3$ and $X^4$ are exemplified by ethylenedioxy, methylethylenedioxy, 1,1-dimethylethylenedioxy, 1,2-dimethylethylenedioxy, trimethylenedioxy, 1-methyltrimethylenedioxy, 2-methyltrimethylenedioxy, 2,2-dimethyltrimethylenedioxy and so on.

The pregnane derivative of general formula (I) according to the invention can be produced by the following processes. The compounds of formula (I-1-1) and the compounds of general formula (I-1-2) [which will hereinafter be referred to sometimes as compound (I-1-1) and compound (I-1-2), respectively] fall within the category of pregnane derivative (I-1). The compounds of general formula (I-2-1) and the compounds of general formula (I-2-2) [which will hereinafter be referred to sometimes as compound (I-2-1) and compound (I-2-2), respectively] are subsumed in the category of pregnane derivative (I-2). The compounds of general formula (I-3-1), compounds of general formula (I-3-2) and compounds of general formula (I-3-3) [which will hereinafter be referred to sometimes as compound (I-3-1), compound (I-3-2) and compound (I-3-3), respectively] are subsumed in the category of pregnane derivative (I-3). The compounds of general formula (I-4-1), compounds of general formula (I-4-2), compounds of general formula (I-4-3) and compounds of general formula (I-4-4) [which will hereinafter be referred to sometimes as compound (I-4-1), compound (I-4-2), compound (I-4-3) and compound (I-4-4), respectively] are subsumed in the category of pregnane derivative (I-4). The compounds of general formula (I-5-1), compound of formula (I-5-2), compounds of general formula (I-5-3), compounds of general formula (I-5-4a), compounds of general formula (I-5-4b) and compounds of general formula (I-5-4c) [which will hereinafter be referred to sometimes as compound (I-5-1), compound (I-5-2), compound (I-5-3), compound (I-5-4a), compound (I-5-4b) and compound (I-5-4c), respectively] are subsumed in the category of pregnane derivative (I-5). The compounds of general formula (I-6-1) [which will hereinafter be referred to sometimes as compound (I-6-1)] are subsumed in the category of pregnane derivative (I-6). The compounds of general formula (I-7-1), compounds of general formula (I-7-2) and compounds of general formula (I-7-3) [which will hereinafter be referred to sometimes as compound (I-7-1), compound (I-7-2) and compound (I-7-3), respectively] are subsumed in the category of pregnane derivative (I-7). The compounds of general formula (I-8-1), compounds of general formula (I-8-2) and compounds of general formula (I-8-3) [which will hereinafter be referred to sometimes as compound (I-8-1), compound (I-8-2) and compound (I-8-3), respectively] are subsumed in the category of pregnane derivative (I-8). The compounds of general formula (I-9-1a), compounds of general formula (I-9-1b) and compounds of general formula (I-9-1c) [which will hereinafter be referred to sometimes as compound (I-9-1a), compound (I-9-1b) and compound (I-9-1c), respectively] are subsumed in the category of pregnane derivative (I-9).

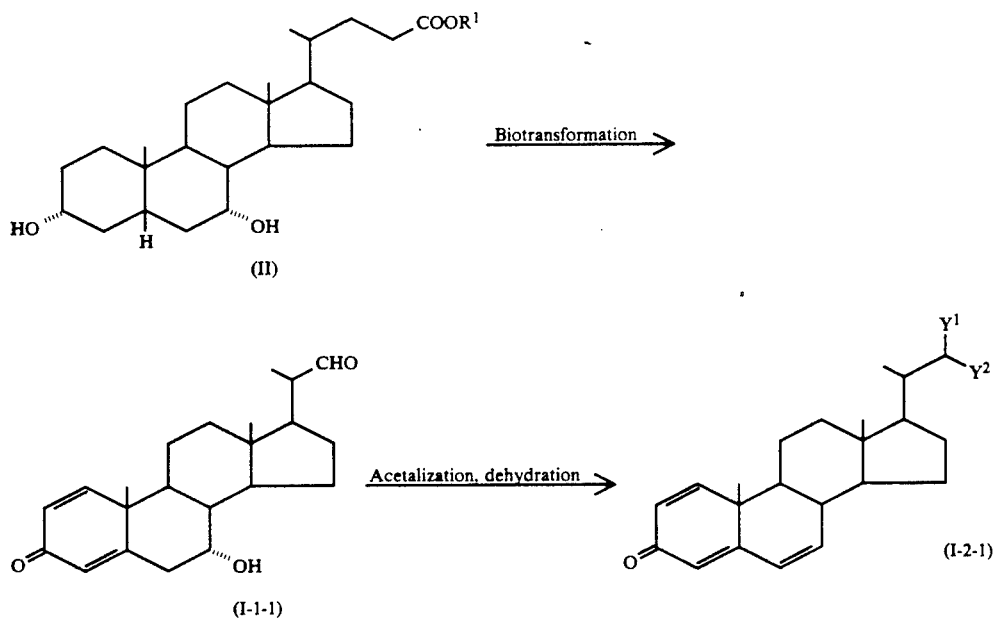

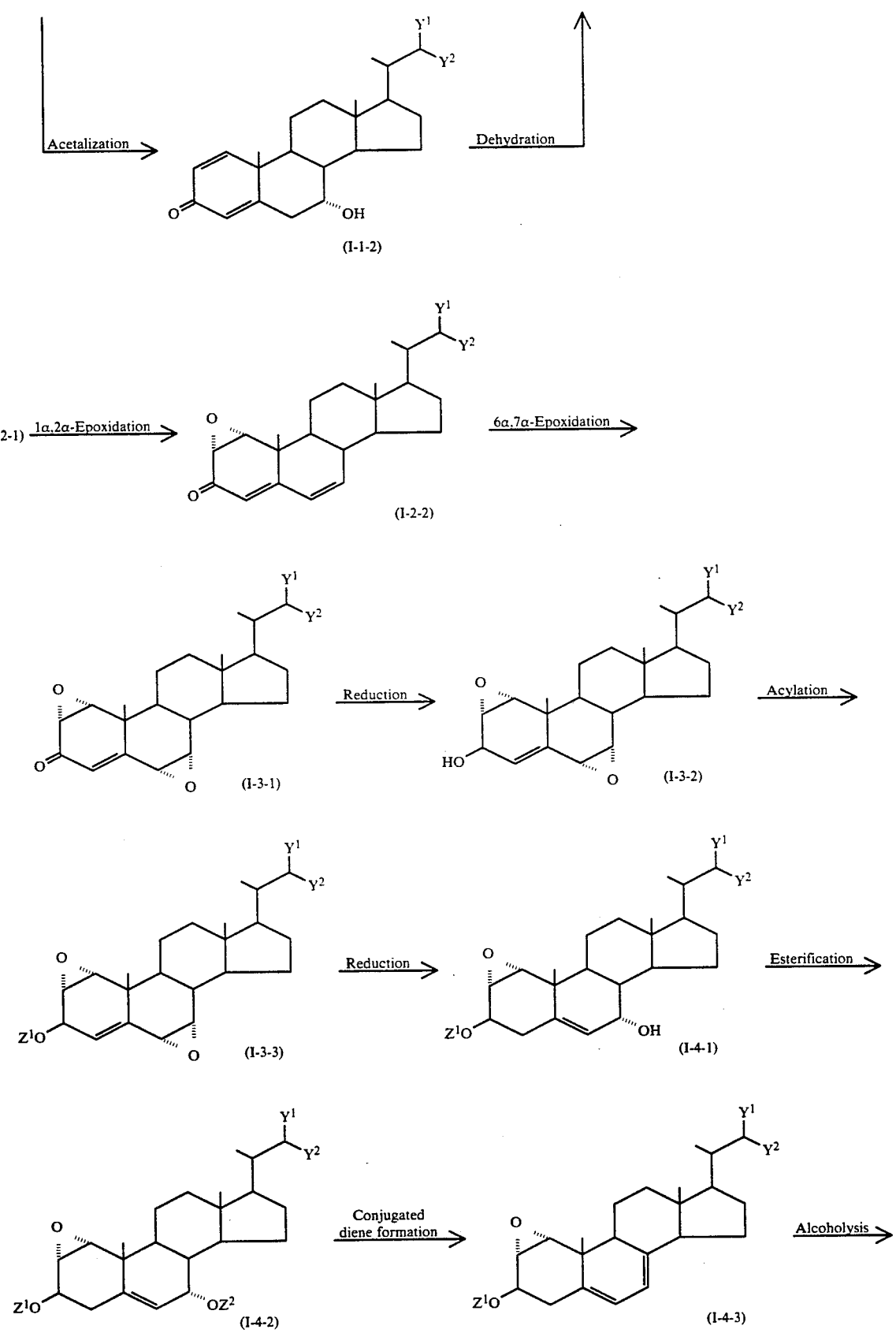

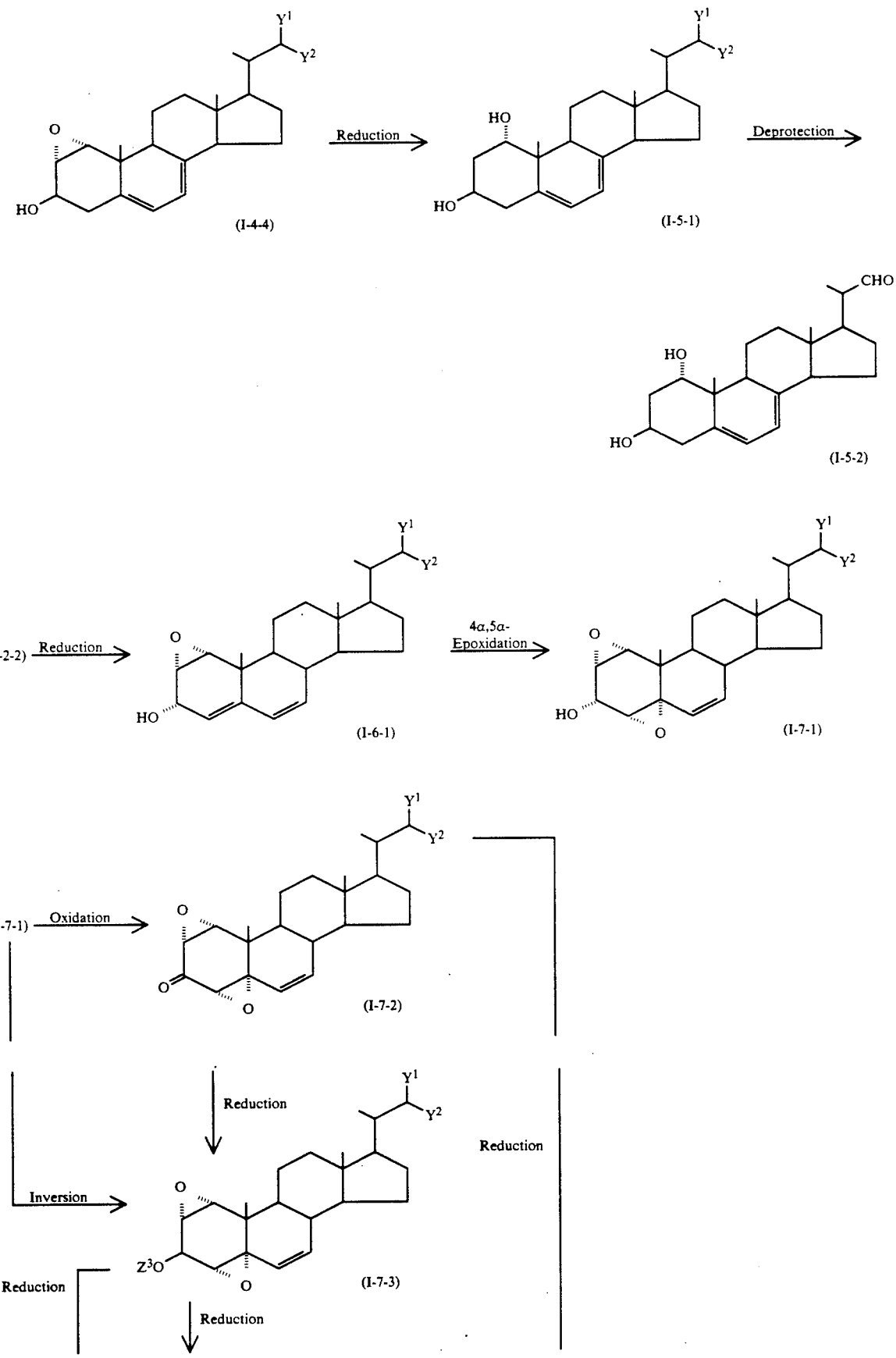

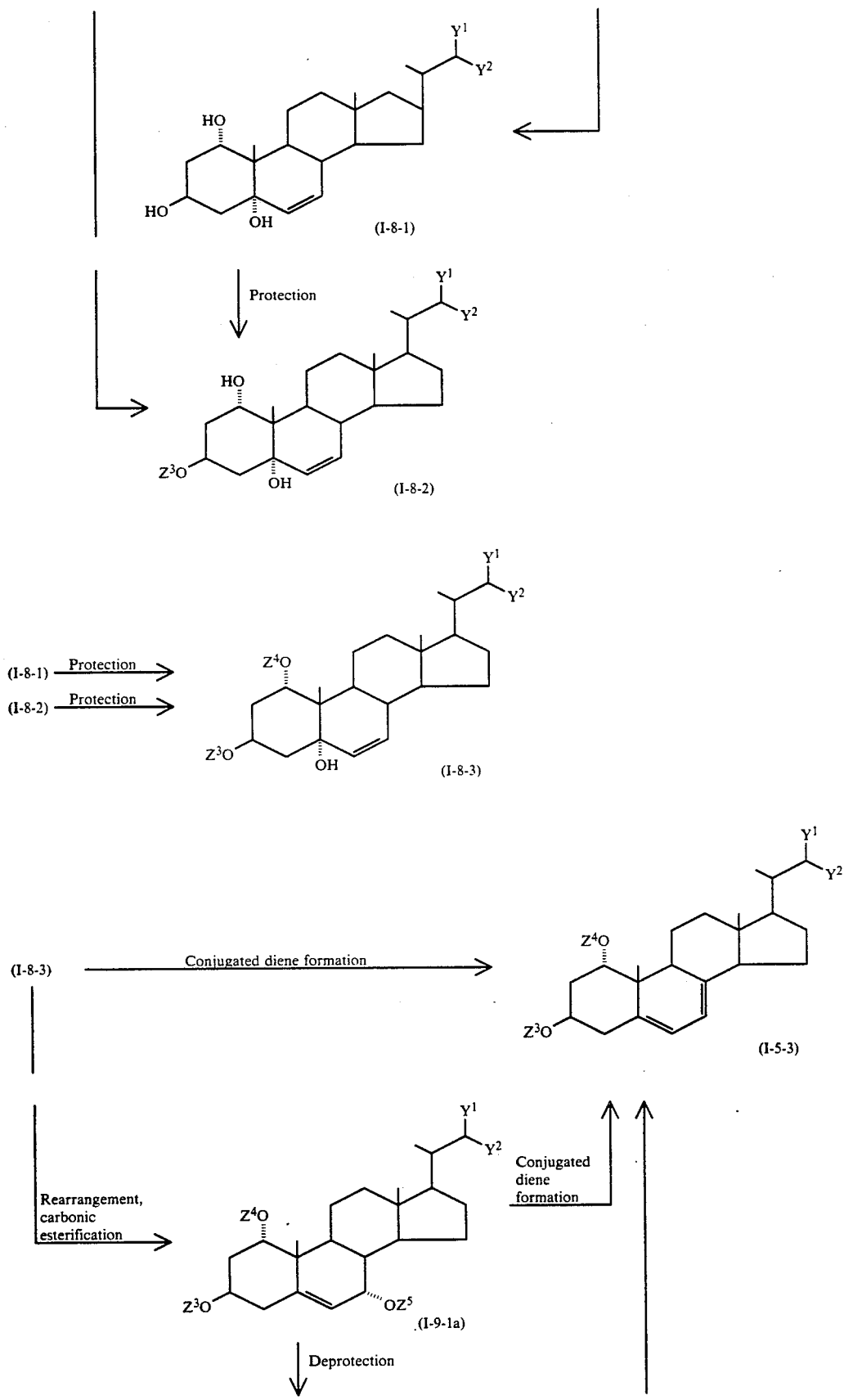

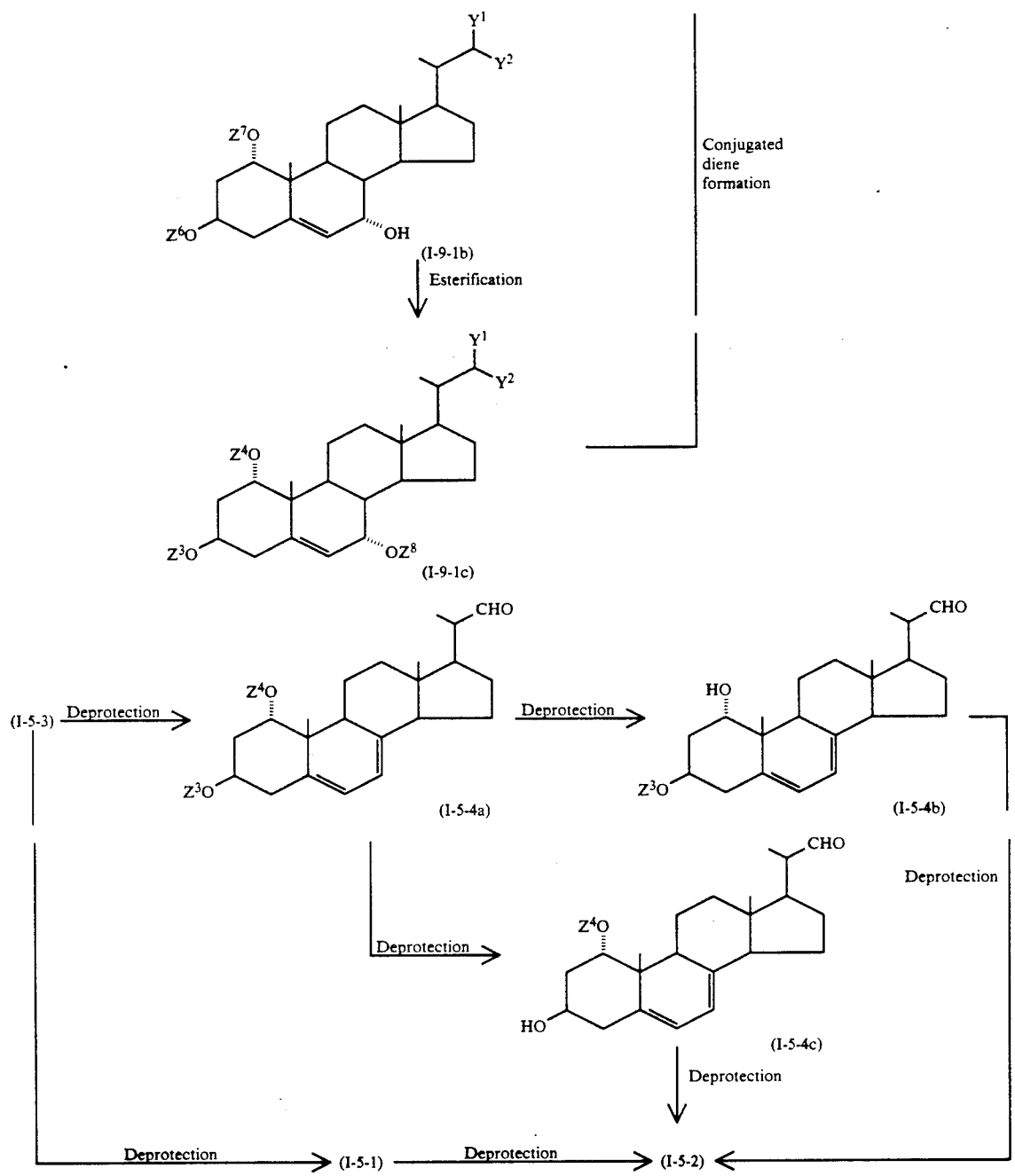

In the above formulas, $R^1$ is a hydrogen atom, an alkali metal atom or one-half of an alkaline earth metal atom; $Y^1$ and $Y^2$ each is a lower alkoxyl group or jointly represent a lower alkylenedioxy group; $Z^1$ is a lower alkanoyl group; $Z^2$ is a lower alkoxycarbonyl group, a lower alkanoyl group, an N-lower alkylcarbamoyl group, an N-arylcarbamoyl group or an N,N-di(lower alkyl)carbamoyl group; $Z^3$ and $Z^4$ each is an acyl group, a lower alkoxycarbonyl group, an N-lower alkylcarbamoyl group, an N-arylcarbamoyl group, an N,N-di(-lower alkyl)carbamoyl group, a tri-substituted silyl group or an alkoxymethyl group which may optionally be substituted; $Z^5$ is a lower alkoxycarbonyl group; $Z^6$ and $Z^7$ each is a hydrogen atom, an acyl group, a lower alkoxycarbonyl group, an N-lower alkylcarbamoyl group, an N-arylcarbamoyl group, an N,N-di(lower alkyl)carbamoyl group, a tri-substituted silyl group or an alkoxymethyl group which may optionally be substituted; and $Z^8$ is an acyl group, an N-lower alkylcarbamoyl group, an N-arylcarbamoyl group or an N,N-di(-lower alkyl)carbamoyl group.

The biotransformation (microbial transformation) of 3α,7α-dihydroxy-5β-cholanic acid (which will hereinafter be referred to as chenodeoxycholic acid) and/or a salt thereof, which is represented by the general formula (II), into 7α-hydroxypregna-1,4-dien-3-one-20-carbaldehyde of formula (I-1-1) is accomplished by cultivating a microbe of the genus Alcaligenes which is capable of producing 7α-hydroxypregna-1,4-dien-3-one-20-carbaldehyde by utilizing chenodeoxycholic acid and/or a salt thereof as a substrate, in a medium containing chenodeoxycholic acid and/or a salt thereof. As an example of said microbe of the genus Alcaligenes being capable of producing 7α-hydroxypregna-1,4-dien-3-one-20-carbaldehyde by utilizing chenodeoxycholic acid and/or a salt thereof as the substrate, there may be mentioned the strain *Alcaligenes faecalis* D4020-K15 [deposited at Fermentation Research Institute, the Agency of Industrial Science and Technology, the Ministry of International Trade and Industry at 1-3, Higashi 1 chome, Yatabe-machi, Tsukuba-gun, Ibaraki Prefecture, Japan (postal zone code 305) as of Nov. 1, 1982 (transferred from FERM P-6300 dated Jan. 4, 1982); deposit number FERM BP-204]. This strain is a mutant of the strain *Alcaligenes faecalis* D4020 [deposited at Fermentation Research Institute, the Agency of Industrial Science and Technology, the Ministry of International Trade and Industry at 1-3, Higashi 1 chome, Yatabe-machi, Tsukuba-gun, Ibaraki Prefecture, Japan (postal zone code 305) as of Sep. 11, 1982 (transferred from FERM P-6298 dated Jan. 4, 1982); deposit number FERM BP-182] as derived by subjecting the parent strain to mutagenic treatment. The bacteriological characteristics of these strains are described in Japanese Patent Application Laid-open Nos. 58-148900, 58-204000, 59-157100 and 59-205396. The aforesaid salt of chenodeoxycholic acid includes salts of chenodeoxycholic acid with alkali metals such as sodium, potassium, etc. or with alkaline earth metals such as calcium, magnesium and so on. The concentration of chenodeoxycholic acid and/or a salt thereof in the medium may generally range from about 1 to about 200 g/l. However, in view of the production yield of 7α-hydroxypregna-1,4-dien-3-one-20-carbaldehyde, conditions for cultivation and economic efficiency such as operability, workability and so on, the concentration range of about 10 to 100 g/l is preferred. While the cultural methods that can be employed are generally the same as those used for aerobic culture of ordinary microorganisms, shake culture or submerged culture with aeration and agitation, using a liquid medium is usually adopted. Incorporated in the medium are those nutrient sources which can be utilized by the microbe of the genus Alcaligenes being capable of producing 7α-hydroxypregna-1,4-dien-3-one-20-carbaldehyde by utilizing chenodeoxycholic acid and/or a salt thereof as a substrate. In regard to carbon sources, chenodeoxycholic acid and/or a salt thereof may be used as a sole carbon source or it may be used in combination with glucose, glycerin, peptone, meat extract, yeast extract and so on. As nitrogen sources, there may be employed various inorganic nitrogen sources such as ammonium sulfate, ammonium chloride, ammonium phosphate, ammonium nitrate, sodium nitrate, potassium nitrate, etc. and organic nitrogen sources such as polypeptone, peptone, meat extract and so on. In addition, inorganic salts such as potassium monohydrogen phosphate, potassium dihydrogen phosphate, magnesium sulfate, etc. are incorporated in the medium. No specific cultural conditions are required but generally shake culture or submerged culture with aeration and agitation is carried out at a temperature of about 25° to 30° C. for a period ranging from about 10 hours to about 7 days.

The 7α-hydroxypregna-1,4-dien-3-one-20-carbaldehyde accumulated in the culture broth is markedly less soluble in water than is the substrate chenodeoxycholic acid or salt thereof and, therefore, generally separates out as a precipitate in the broth. The harvest of the accumulated 7α-hydroxypregna-1,4-dien-3-one-20-carbaldehyde can be accomplished, for example, by the following procedures. The insoluble fraction separated by centrifugation or filtration of the culture broth is rinsed with water, if necessary, to remove the residual chenodeoxycholic acid and/or salt thereof and, then, extracted with an organic solvent capable of dissolving 7α-hydroxypregna-1,4-dien-3-one-20-carbaldehyde, such as a single solvent, e.g. ethyl acetate, chloroform, methanol, etc., or a mixed solvent, e.g. a mixture of ethyl acetate and methanol, whereby an extract containing 7α-hydroxypregna-1,4-dien-3-one-20-carbaldehyde is obtained. An alternative procedure comprises extracting the culture broth containing the precipitate and cells with an organic solvent which is capable of dissolving 7α-hydroxypregna-1,4-dien-3-one-20-carbaldehyde and is immiscible with water, such as a single solvent such as ethyl acetate, chloroform, etc. or a mixed solvent such as a mixture of ethyl acetate and methanol to give an extract containing 7α-hydroxypregna-1,4-dien-3-one-20-carbaldehyde. From the extract obtained in any of the above manners, the microbial cells and other insoluble impurity are removed by centrifugation or filtration as required and, then, the organic solvent is distilled off to recover the desired 7α-hydroxypregna-1,4-dien-3-one-20-carbaldehyde. The 7α-hydroxypregna-1,4-dien-3-one-20-carbaldehyde thus recovered contains substantially no residual substrate chenodeoxycholic acid or salt thereof or any byproduct, and, therefore, by subjecting it to recrystallization, for example from aqueous methanol, the object compound 7α-hydroxypregna-1,4-dien-3-one-20-carbaldehyde can be easily obtained in high purity.

The conversion of 7α-hydroxypregna-1,4-dien-3-one-20-carbaldehyde (I-1-1) to compound (I-2-1) can be accomplished by subjecting the 7α-hydroxypregna-1,4-dien-3-one-20-carbaldehyde to dehydrative acetalization reaction or by the steps of acetalizing the 7α-hydroxypregna-1,4-dien-3-one-20-carbaldehyde to give the corresponding compound (I-1-2) and subjecting this compound (I-1-2) to dehydration reaction. The first-mentioned dehydrative acetalization reaction is accomplished by reacting 7α-hydroxypregna-1,4-dien-3-one-20-carbaldehyde and an acetalizing agent under reflux in an aromatic hydrocarbon solvent such as benzene, toluene, etc. in the presence of an acid catalyst such as p-toluenesulfonic acid, pyridinium p-toluenesulfonate, camphorsulfonic acid, phosphorus tribromide, etc. under azeotropic dehydration conditions. The acetalizing agent is exemplified by lower alcohols such as methanol, ethanol, propanol, butanol, etc.; lower alkylene glycols including various ethylene glycols, e.g. ethylene glycol, 1,2-propanediol, 2-methyl-1,2-propanediol, 2,3-butanediol, etc. and trimethylene glycols, e.g. 1,3-propanediol, 1,3-butanediol, 2-methyl-1,3-propanediol, 3-methyl-1,3-butanediol, 2-methyl-1,3-butanediol, 2,2-dimethyl-1,3-propanediol, etc.; and lower alkylene acetals of ketones, such as 2-butanone ethylene acetal, 3-pentanone ethylene acetal, 2-butanone(2,2-dimethyltrimethylene) acetal and so on. The second-mentioned procedure of conducting acetalization and dehydration reactions independently is carried out in the following manner. Thus, 7α-hydroxypregna-1,4-dien-3-one-20-carbaldehyde and a lower alcohol, a trimethylene glycol or the like, which is among said acetalizing agents, are first reacted in a halogenated hydrocarbon solvent, such as methylene chloride, chloroform etc., in the presence of a dehydrating agent, such as molecular sieves, copper sulfate, etc., and an acid catalyst, such as p-toluenesulfonic acid, pyridinium p-toluenesulfonate, camphorsulfonic acid, etc., at a temperature of about 0° to 50° C. The dehydrating agent is then removed from the resulting reaction mixture and the solvent is distilled off. Then, the residue is subjected to a separation-purification procedure such as chromatography, recrystallization, etc. to recover compound (I-1-2). Then, this compound (I-1-2) is reacted under reflux in the same aromatic hydrocarbon solvent as mentioned above in the presence of an acid catalyst such as p-toluenesulfonic acid, camphorsulfonic acid, etc. under azeotropic dehydration conditions. In the dehydrative acetalization reaction and the acetalization reaction preceding the dehydration reaction, the acetalizing agent is generally used in a proportion of about 2 to 10 moles, preferably about 2.5 to 5 moles, per mole of 7α-hydroxypregna- 1,4-dien-3-one-20-carbaldehyde. The proportion of the solvent is generally about 10 to 200-fold by weight based on 7α-hydroxypregna- 1,4-dien-3-one-20-carbaldehyde and the proportion of the acid catalyst is generally about 0.001 to 0.3 mole, preferably about 0.005 to 0.1 mole, per mole of 7α-hydroxypregna- 1,4-dien-3-one-20-carbaldehyde. In the acetalization reaction preceding the dehydration reaction, the dehydrating agent is generally used in an amount capable of removing at least one mole, preferably about 2 to 10 moles, of water from the reaction system based on each mole of 7α-hydroxypregna-1,4-dien-3-one-20-carbaldehyde. In the dehydration reaction of compound (I-1-2), the solvent is generally used in an amount ranging from about 10 to 200-fold by weight based on compound (I-1-2) and the acid catalyst is generally used in a proportion of about 0.001 to 0.3 mole, preferably about 0.005 to 0.1 mole, per mole of compound (I-1-2).

The separation and purification of compound (I-2-1) from the reaction mixture obtained by the dehydrative acetalization or the sequential acetalization and dehydration reactions can be performed by the same procedures as those used commonly for the recovery of products of organic synthetic reactions from reaction mixtures. For example, the compound (I-2-1) can be isolated by mixing the reaction mixture with an aqueous solution of sodium hydrogen carbonate, extracting the resulting mixture with a solvent such as hexane, diethyl ether, benzene, ethyl acetate, methylene chloride, etc., then removing the solvent from the extract by distillation and subjecting the residue to a purification procedure such as chromatography, recrystallization and so on.

The conversion of compound (I-2-1) to compound (I-2-2) is accomplished by reacting compound (I-2-1) with hydrogen peroxide in a solvent mixture of a lower alcohol such as methanol, ethanol, etc. with water in the presence of a base such as an alkali metal hydroxide, e.g. sodium hydroxide, potassium hydroxide, etc., at a temperature within the range of about 0° to 30° C. The proportion of the base is generally about 0.2 to 0.5 mole per mole of compound (I-2-1). The proportion of hydrogen peroxide is generally about 2 to 20 moles, preferably about 3 to 10 moles, per mole of compound (I-2-1). This 1α,2α-epoxidation reaction can be expediently carried out by adding an about 30% aqueous solution of hydrogen peroxide, which is commercially available, and said base to a solution of compound (I-2-1) in about 10 to 100-fold by weight, relative to (I-2-1), of a lower alcohol and stirring the mixture at room temperature for about 12 to 24 hours.

From the reaction mixture thus obtained by the above 1α,2α-epoxidation, compound (I-2-2) can be separated and purified by the following and other procedures. Thus, the reaction mixture is first diluted with water and a portion of the solvent lower alcohol is distilled off under reduced pressure. The residue is extracted with a solvent such as diethyl ether, ethyl acetate, chloroform, methylene chloride and so on. The extract is then washed successively with aqueous potassium iodide solution and aqueous sodium chloride solution and the solvent is distilled off under reduced pressure. The residue is subjected to a separation-purification procedure such as chromatography, recrystallization, etc. to recover the desired compound (I-2-2).

The compound (I-2-1) and compound (I-2-2) can be respectively subjected to deprotection reaction to give the corresponding aldehydes.

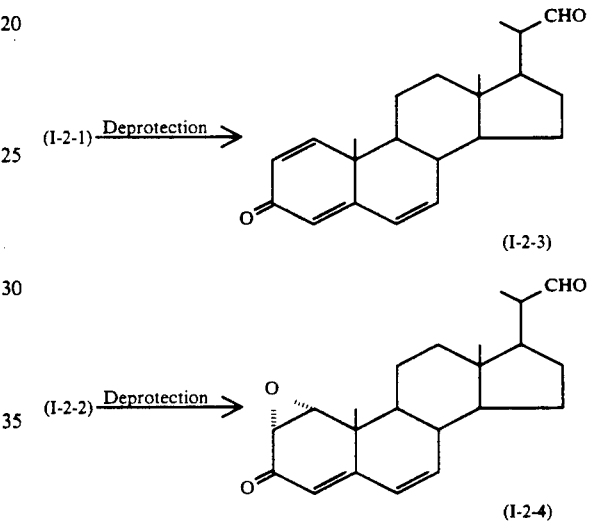

The conversion of compound (I-2-1) to pregna-1,4,6-trien-3-one-20-carbaldehyde of formula (I-2-3) [which will hereinafter be referred to sometimes as compound (I-2-3)] and the conversion of compound (I-2-2) to 1α,2α-epoxypregna-4,6-dien-3-one-20-carbaldehyde of formula (I-2-4) [which will hereinafter referred to sometimes as compound (I-2-4)] are accomplished by reacting compound (I-2-1) or compound (I-2-2) with a lower alkanone such as acetone, 2-butanone, 3-pentanone, etc. in the presence of about 0.001 to 0.1 mole, per mole of compound (I-2-1) or (I-2-2), of an acid such as p-toluenesulfonic acid, pyridinium p-toluenesulfonate, etc. at a temperature of about 20° to 80° C. or by reacting compound (I-2-1) or compound (I-2-2) with water or a lower alcohol, such as methanol, ethanol, etc., in the presence of about 0.01 to 1 mole, per mole of compound (I-2-1) or (I-2-2), of an acid, such as hydrochloric acid, p-toluenesulfonic acid, etc., at a temperature within the range of about −10° C. to about 60° C. The lower alkanone is generally used in a proportion of about 100 to 1000-fold by weight based on compound (I-2-1) or compound (I-2-2). The proportion of said water or lower alcohol is generally about 10 to 200-fold by weight based on compound (I-2-1) or compound (I-2-2). Where water is used, a water-miscible organic solvent such as tetrahydrofuran, 1,2-dimethoxyethane, etc. is preferably present in the reaction system. The preferred proportion of such organic solvent is about 20 to 100- fold by weight based on compound (I-2-1) or compound (I-2-2).

The separation and purification of compound (I-2-3) or compound (I-2-4) from the reaction mixture obtained by the above deprotection reaction can be carried out by the following and other procedures. After removal, if necessary, of the lower alkanone, lower alcohol or-/and organic solvent from the reaction mixture by distillation, the residue is diluted with water and extracted with methylene chloride. The extract is washed successively with water, aqueous sodium hydrogen carbonate solution and aqueous sodium chloride solution and the solvent is distilled off under reduced pressure. Finally the residue is purified by chromatography, recrystallization, etc. to give compound (I-2-3) or compound (I-2-4).

The compound (I-2-3) or compound (I-2-4) can be converted to a pregnane derivative of general formula (I-2) wherein $X^1$ and $X^2$ jointly represent a lower alkylenedioxy group, for example by reacting compound (I-2-3) or (I-2-4) with a lower alkylene acetal of a ketone such as 2-butanone(2,2-dimethyltrimethylene)acetal in the presence of an acid catalyst such as pyridinium p-toluenesulfonate, etc., in an aromatic hydrocarbon solvent such as benzene, toluene, etc. under refluxing.

The conversion of compound (I-2-2) to compound (I-3-1) is carried out by reacting compound (I-2-2) with an organic peracid such as peracetic acid, perbenzoic acid, m-chloroperbenzoic acid and so on. The organic peracid is generally used in a proportion of about 1 to 10 moles, preferably about 2 to 8 moles, per mole of compound (I-2-2). This reaction is generally conducted in a halogenated hydrocarbon solvent such as chloroform, methylene chloride, etc. at a temperature of about 0° to 30° C. This $6\alpha,7\alpha$-epoxidation reaction can be expediently carried out by adding said organic peracid or a solution thereof in about 50 to 200-fold by weight, based on said organic peracid, of a halogenated hydrocarbon to a solution of compound (I-2-2) in about 10 to 100-fold by weight, based on compound (I-2-2), of a halogenated hydrocarbon solvent and stirring the resulting mixture at room temperature for about 6 hours to about 3 days. For the purpose of neutralizing the organic acid liberated from said organic peracid, about 1 to 5 moles, based on each mole of compound (I-2-2), of a basic compound, such as sodium carbonate, potassium carbonate, sodium hydrogen carbonate, potassium hydrogen carbonate, etc., is preferably present in the reaction system.

The separation and purification of compound (I-3-1) from the $6\alpha,7\alpha$-epoxidation reaction mixture can be carried out by the following and other procedures. The reaction mixture is washed successively with aqueous potassium iodide solution and aqueous sodium chloride solution, the solvent is then distilled off under reduced pressure and the residue is subjected to a purification procedure such as chromatography, recrystallization, etc. to give compound (I-3-1).

The reduction reaction of compound (I-3-1) to compound (I-3-2) is carried out by contacting the compound (I-3-1) with a reducing agent such as sodium borohydride. The reducing agent is generally used in a proportion of about 0.5 to 2.0 moles, preferably about 0.8 to 1.2 moles, per mole of compound (I-3-1). This reaction is generally conducted in an alcohol solvent, such as methanol, ethanol, etc., or an ether solvent, such as tetrahydrofuran, 1,2-dimethoxyethane, etc., at a temperature within the range of about 0° to 25° C. The amount of the solvent is generally about 20 to 100-fold by weight based on compound (I-3-1). This reaction can be advantageously conducted by dissolving compound (I-3-1) in said solvent, adding the reducing agent gradually under stirring and cooling at about 0° C. and finally stirring the mixture at about 0° C. for a period ranging from about 10 minutes to about an hour.

The separation and purification of compound (I-3-2) from the reaction mixture obtained by the above reduction reaction can be carried out by the following and other procedures. The reaction mixture is diluted with water and, after addition of a small amount of cold hydrochloric acid, extracted with methylene chloride. The extract is washed with cold aqueous sodium hydrogen carbonate solution and aqueous sodium chloride solution in that order and the solvent is distilled off under reduced pressure. Finally, the residue is subjected to a purification procedure such as chromatography, recrystallization, etc. to give compound (I-3-2).

The conversion of compound (I-3-2) to compound (I-3-3) is accomplished by reacting the compound (I-3-2) with a lower alkanoic acid anhydride, such as acetic anhydride, propionic anhydride, butyric anhydride, valeric anhydride, etc., or a lower alkanoic acid halide, such as acetyl chloride, propionyl chloride, butyryl chloride, valeryl chloride, etc., in the presence of a basic compound, such as pyridine, triethylamine, etc., at a temperature within the range of about 0° to 25° C. The lower alkanoic acid anhydride or lower alkanoic acid halide is generally used in a proportion of about 1 to 10 moles per mole of compound (I-3-2). The amount of said basic compound may generally range from about 2 to 20 moles per mole of compound (I-3-2) but is preferably not less than about 2 moles per mole of said lower alkanoic acid anhydride or lower alkanoic acid halide. This acylation reaction may be conducted in an organic solvent such as methylene chloride, diethyl ether and so on. The amount of such organic solvent is generally not more than about 200-fold by weight based on compound (I-3-2). This reaction can be advantageously carried out by adding said lower alkanoic acid anhydride or lower alkanoic acid halide gradually to a mixture of said compound (I-3-2) and basic compound or a solution thereof in an organic solvent under cooling at about 0° C. and, then, stirring the mixture at room temperature for about 2 to 12 hours. This acylation reaction may be hastened by permitting an esterification catalyst such as 4-(dimethylamino)pyridine to be present in the reaction system in a proportion of about 0.01 to 0.1 mole per mole of compound (I-3-2).

From the reaction mixture thus obtained by the above acylation reaction, the product compound (I-3-3) can be separated and purified by the following and other procedures. To the reaction mixture is added a solvent such as diethyl ether or methylene chloride and the solution is washed with water. Where pyridine was used as said basic compound, this washing is preferably performed with an aqueous solution of copper sulfate. After washing, the organic layer is distilled under reduced pressure to remove the solvent and the residue is subjected to a purification procedure such as chromatography, recrystallization etc. to recover the desired compound (I-3-3).

The compounds (I-3-1), (I-3-2) and (I-3-3) can be respectively subjected to deprotection reaction to give the corresponding aldehydes.

(I-3-1) Deprotection →

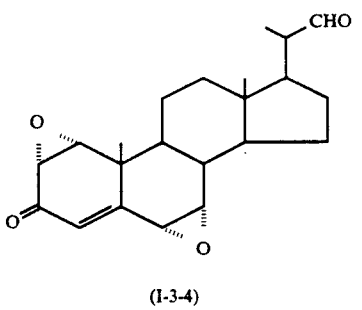

(I-3-4)

(I-3-2) Deprotection →

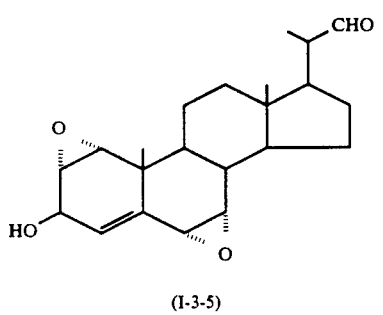

(I-3-5)

(I-3-2) Deprotection →

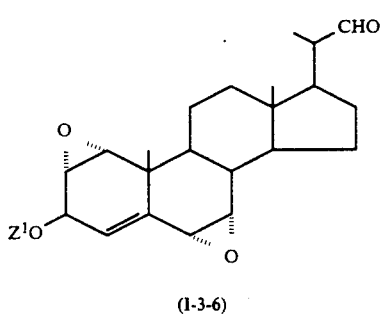

(I-3-6)

wherein $Z^1$ has the meaning defined hereinbefore.

1α,2α;6α,7α-Diepoxy-3-oxopregn-4-ene-20-carbaldehyde of formula (I-3-4) [which will hereinafter be referred to sometimes as compound (I-3-4)], 1α,2α;6α,7α-diepoxy-3β-hydroxypregn-4-ene-20-carbaldehyde of formula (I-3-5) which will hereinafter be referred to sometimes as compound (I-3-5)], and compounds of general formula (I-3-6) [which will hereinafter be referred to sometimes as compound (I-3-6)] can be produced by the same reaction and workup procedures as those described for the conversion of compound (I-2-1) or compound (I-2-2) to compound (I-2-3) or compound (I-2-4) except that, in lieu of compound (I-2-1) or (I-2-2), compound (I-3-1), compound (I-3-2) or compound (I-3-3) is subjected to deprotection.

The compound (I-3-4), compound (I-3-5) or compound (I-3-6) can be converted to the corresponding compound (I-3-1), compound (I-3-2) or compound (I-3-3), for example by reacting compound (I-3-4), (I-3-5) or (I-3-6) with a lower alkoxytrimethylsilane such as methoxytrimethylsilane, ethoxytrimethylsilane, etc. or a bis(trimethylsilyloxy) lower alkane such as 1,2-bis(trimethylsilyloxy)ethane, 2,2-dimethyl-1,3-bis(trimethylsilyloxy)propane, etc., in the presence of trimethylsilyl trifluoromethanesulfonate at a temperature within the range of about −100° C. to about −60° C. This conversion may be performed in a solvent such as methylene chloride, chloroform, and so on.

The reduction reaction of compound (I-3-3) to compound (I-4-1) is carried out by treating compound (I-3-3) with a reducing agent in the presence of a palladium compound and a tertiary phosphine. As the palladium compound, tris(dibenzylideneacetone)dipalladium(chloroform), palladium acetate, palladium nitrate, palladium chloride, bis(acetylacetonato)palladium, tetrakis(triphenylphosphine)palladium, etc. can be used. The proportion of the palladium compound is generally about 0.01 to 0.5 mole per mole of compound (I-3-3). As examples of said tertiary phosphine, there may be mentioned tributylphosphine, triethylphosphine, triphenylphosphine, tritolylphosphine, 1,2-bis(diphenylphosphino)ethane, and so on. The proportion of such tertiary phosphine is generally about 1 to 20 moles per mole of the palladium compound. As examples of the reducing agent that can be employed, there may be mentioned salts of formic acid such as ammonium formate, triethylammonium formate, trimethylammonium formate, etc. and metal hydride compounds such as sodium borohydride, lithium aluminum hydride, lithium triethylborohydride, diisobutylaluminum hydride, sodium cyanoborohydride, tributyltin hydride, polymethylhydrosiloxane and so on. The proportion of the reducing agent is generally about 2 to 10 moles per mole of compound (I-3-3). This reaction is preferably conducted in an ether solvent such as tetrahydrofuran, 1,2-dimethoxyethane, 1,4-dioxane, etc. at a temperature within the range of about 0° to 120° C. The proportion of said solvent is preferably about 30 to 100-fold by weight based on compound (I-3-3). This reaction is preferably conducted by adding said palladium compound and tertiary phosphine to an ether solvent in an inert atmosphere such as argon gas or nitrogen gas at room temperature, stirring the mixture for about 5 to 60 minutes, then adding said reducing agent to the resulting solution, stirring the mixture further for about 10 to 60 minutes, adding a solution of compound (I-3-3) in an ether solvent, and stirring the mixture under reflux for about 10 minutes to about 24 hours.

From the reaction mixture thus obtained by the above reduction reaction, the product compound (I-4-1) can be separated and purified by the following and other procedures. The reaction mixture is diluted with methylene chloride and washed successively with cold hydrochloric acid, aqueous sodium hydrogen carbonate solution and aqueous sodium chloride solution. From the organic layer separated, the solvent is distilled off under reduced pressure and the residue is subjected to a purification procedure such as chromatography, recrystallization and so on to recover the desired compound (I-4-1).

In the above reduction reaction, there are cases in which an 3β-alkanoyloxy-1α,2α-epoxypregn-4-en-7α-ol of the general formula

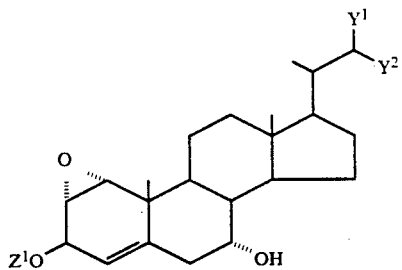

wherein $Y^1$, $Y^2$ and $Z^1$ have the meanings defined hereinbefore, [which will hereinafter be referred to sometimes as compound (III)] is by-produced but this compound (III) can be converted to compound (I-2-2), for example by the following process.

(III) $\xrightarrow{\text{Alcoholysis}}$

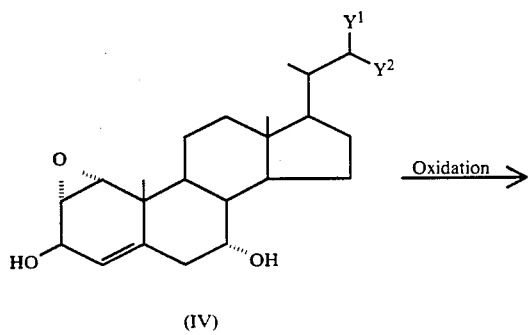

$\xrightarrow{\text{Oxidation}}$

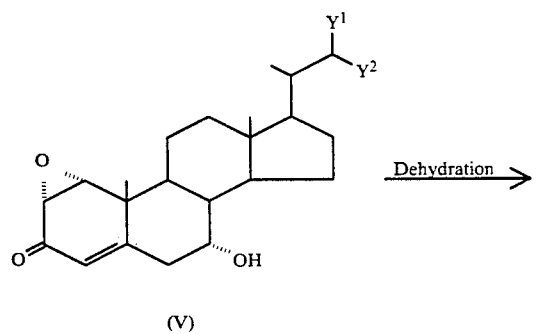

$\xrightarrow{\text{Dehydration}}$

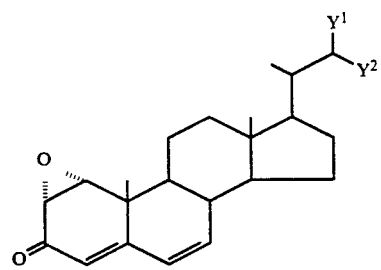

(I-2-2)

In the above formulas, $Y^1$ and $Y^2$ have the meanings defined hereinbefore.

Thus, alcoholysis of compound (III) with a lower alcohol, such as methanol, ethanol, etc., in the presence of a basic compound, such as anhydrous potassium carbonate, anhydrous sodium carbonate, etc., at a temperature of about 0° to 30° C. yields an 1α,2α-epoxy-pregn-4-ene-3β,7α-diol derivative of general formula (IV). This 1α,2α-epoxypregn-4-ene- 3α,7α-diol derivative (IV) is oxidized with manganese dioxide in a solvent, such as hexane, diethyl ether, methylene chloride, chloroform, etc., at room temperature to give an 1α,2α-epoxy-7a-hydroxypregn-4-en-3-one derivative of general formula (V) and finally this 1α,2α-epoxy-7α-hydroxypregn-4-en-3-one derivative is subjected to dehydration reaction in t-butyl alcohol in the presence of potassium t-butoxide at room temperature to give the compound (I-2-2). The compound (I-2-2) thus obtained can be subjected to said 6α,7α-epoxidation to compound (I-2-3) and to the reduction to compound (I-6-1) which will be described hereinafter.

The conversion of compound (I-4-1) to compound (I-4-2) is accomplished by reacting the compound (I-4-1) with an esterifying agent in the presence of a basic compound such as pyridine, triethylamine, etc. at a temperature within the range of about 0° to 100° C. The esterifying agent is exemplified by lower alkyl halocarbonates such as methyl chlorocarbonate, ethyl chlorocarbonate, propyl chlorocarbonate, isopropyl chlorocarbonate, butyl chlorocarbonate, methyl bromocarbonate, ethyl bromocarbonate, etc.; lower alkanoic acid anhydrides such as acetic anhydride, propionic anhydride, butyric anhydride, valeric anhydride, etc.; lower alkanoic acid halides such as acetyl chloride, propionyl chloride, butyryl chloride, valeryl chloride, etc.; N,N-di(lower alkyl)carbamoyl halides such as N,N-dimethylcarbamoyl chloride, N,N-diethylcarbamoyl chloride, N,N-dipropylcarbamoyl chloride, etc.; lower alkyl isocyanates such as methyl isocyanate, ethyl isocyanate, propyl isocyanate, etc.; and aryl isocyanates such as phenyl isocyanate, tolyl isocyanate and so on. Where a lower alkyl halocarbonate is used as the esterifying agent, there is produced a pregnane derivative of general formula (I-4-2) wherein $Z^2$ is a lower alkoxycarbonyl group, and where a lower alkanoic acid anhydride or a lower alkanoic acid halide is used, there is produced a pregnane derivative of general formula (I-4-2) wherein $Z^2$ is a lower alkanoyl group. Where an N,N-di(lower alkyl)carbamoyl halide is used as the esterifying agent, there is produced a pregnane derivative of general formula (I-4-2) wherein $Z^2$ is an N,N-di(-lower alkyl)carbamoyl group, while the use of a lower alkyl isocyante gives rise to a pregnane derivative of general formula (I-4-2) wherein $Z^2$ is an N-lower alkylcarbamoyl group. Where an N-aryl isocyanate is used, a pregnane derivative of general formula (I-4-2) wherein $Z^2$ is an N-arylcarbamoyl group is produced. The proportion of the esterifying agent is generally about 1.2 to 20 moles per mole of compound (I-4-1). When the esterifying agent is a lower alkyl halocarbonate, a lower alkanoic acid anhydride, a lower alkanoic acid halide or an N,N-di(lower alkyl)carbamoyl halide, said basic compound is preferably used in a proportion of about 2 to 40 moles per mole of compound (I-4-1) and in a proportion not less than about 2 moles per mole of the esterifying agent. Where a lower alkyl isocyanate or an aryl isocyanate is used as said esterifying agent, the basic compound is generally used in a proportion of about 0.0001 to 10 moles per mole of compound (I-4-1). This esterification reaction may be conducted in a solvent such as methylene chloride, diethyl ether, benzene, toluene, etc. and the proportion of such solvent is generally not more than about 200-fold by weight based on compound (I-4-1). This reaction can be advantageously carried out by adding the esterifying agent gradually to a mixture of said compound (I-4-1) and basic compound or a solution thereof in a solvent under cooling at about 0° C. and then stirring the mixture at a temperature within the range of about 0° to 100° C. for about 10 minutes to about 12 hours. Where the reaction is conducted using a lower alkyl halocarbonate, a lower alkanoic acid anhydride, a lower alkanolic acid halide or an N,N-di(lower alkyl)carbamoyl halide as the esterifying agent, the esterification reaction can be hastened by permitting an esterification catalyst such as 4-(dimethylamino)pyridine or the like to be present in the reaction system in a proportion of about 0.01 to 0.1 mole per mole of compound (I-4-1).

From the reaction mixture thus obtained from the above esterification reaction, the product compound (I-4-2) can be separated and purified by the following and other procedures. After addition of water, if necessary, the reaction mixture is added to methylene chloride and the solution is washed with water. From the organic layer separated, the solvent is distilled off under reduced pressure and the residue is subjected to a purification procedure such as chromatography, recrystallization and so on to recover the desired compound (I-4-2).

The conversion of compound (I-4-2) to compound (I-4-3) is accomplished by reacting the compound (I-4-2) in the presence of a palladium compound. The palladium compound is exemplified by tris(dibenzylideneacetone)dipalladium(chloroform), palladium acetate, palladium nitrate, palladium chloride, bis-(acetylacetonato)palladium, tetrakis(triphenylphosphine)palladium and so on. The proportion of the palladium compound is generally about 0.01 to 0.5 mole per mole of compound (I-4-2). The palladium atom derived from such palladium compound is preferably available as coordinated by a tertiary phosphine in the reaction system and, therefore, such a tertiary phosphine may be added to the reaction system as necessary. As examples of such tertiary phosphine, there may be mentioned tributylphosphine, triethylphosphine, triphenylphosphine, tritolylphosphine, 1,2-bis(diphenylphosphino)ethane and so on. The proportion of the tertiary phosphine is generally about 1 to 20 moles per mole of the palladium compound. The reaction temperature is generally in the range of about 20° to 150° C. This conjugated diene-forming reaction is preferably conducted in an ether solvent such as 1,4-dioxane, tetrahydrofuran, etc. and the proportion of such solvent is preferably about 5 to 500-fold by weight based on compound (I-4-2). This reaction can be advantageously carried out by adding the palladium compound, as well as the tertiary phosphine if desired, to said ether solvent in an inert atmosphere such as argon gas or nitrogen gas at room temperature, stirring the mixture for about 5 to 60 minutes, then adding a solution of compound (I-4-2) in the same ether solvent as mentioned above, and stirring the mixture under reflux for about 1 to 15 hours.

From the reaction mixture thus obtained by the above reconjugated diene-forming reaction, the product compound (I-4-3) can be separated and purified by the following and other procedures. The reaction mixture is filtered through a glass filter with the aid of Florisil and the filtrate is concentrated under reduced pressure. The concentrate is then subjected to a purification procedure such as chromatography, recrystallization and so on to recover the compound (I-4-3).

The conversion of compound (I-4-3) to compound (I-4-4) is carried out by reacting the compound (I-4-3) with a lower alcohol, such as methanol, ethanol, etc., in the presence of a basic compound, such as anhydrous potassium carbonate, anhydrous sodium carbonate and so on. The proportion of the basic compound is generally about 2 to 10 moles per mole of compound (I-4-3). The lower alcohol is generally used in a proportion of about 100 to 1,000-fold by weight based on compound (I-4-3). The reaction temperature is generally in the range of about 0° to 30° C. This alcoholysis reaction is preferably carried out by adding said basic compound to a solution of compound (I-4-3) in a lower alcohol and stirring the mixture at room temperature for about 0.5 to 12 hours.

From the reaction mixture thus obtained by the above alcoholysis reaction, the product compound (I-4-4) can be separated and purified by the following and other procedures. The reaction mixture is filtered through a glass filter with the aid of Celite and the filtrate is concentrated under reduced pressure. The concentrate is diluted with water and extracted with methylene chloride. From the resulting extract, the solvent is distilled off and the residue is subjected to a purification procedure such as chromatography, recrystallization and so on to recover the compound (I-4-4).

Among compounds of formula (I-4), compounds of the general formula

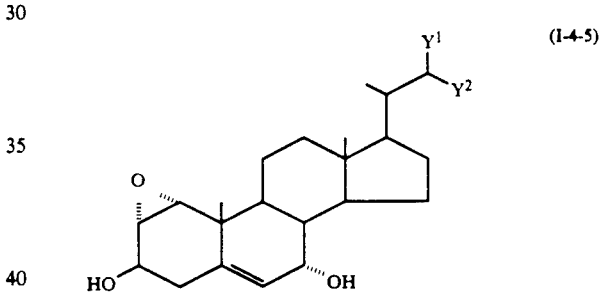

(I-4-5)

wherein Y¹ and Y² have the meanings defined hereinbefore, [which compounds will hereinafter be referred to sometimes as compound (I-4-5)] and compounds of the general formula

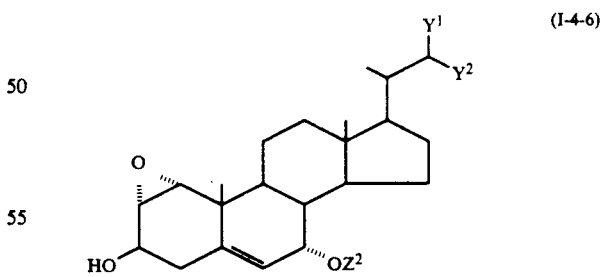

(I-4-6)

wherein Y¹, Y² and Z² have the meanings defined hereinbefore, [which compounds will hereinafter be referred to sometimes as compound (I-4-6)] can be obtained by the same reaction and workup procedures as those described hereinbefore for the conversion of compound (I-4-3) to compound (I-4-4) except that, in lieu of compound (I-4-3), compound (I-4-1) or (I-4-2) is subjected to alcoholysis.

Among compounds (I-4), aldehydes of the general formula

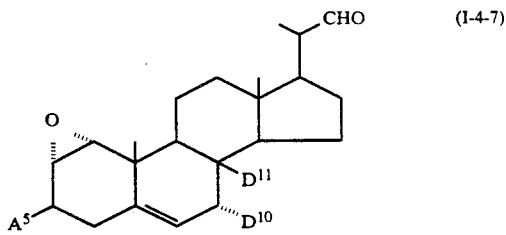
(I-4-7)

wherein $A^5$, $D^{10}$ and $D^{11}$ have the meanings defined hereinbefore, [which aldehydes will hereinafter be referred to sometimes as compound (I-4-7)] are derived from acetals of the general formula

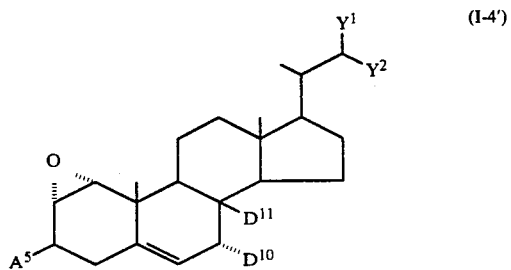
(I-4')

wherein $A^5$, $D^{10}$, $D^{11}$, $Y^1$ and $Y^2$ have the meanings defined hereinbefore, [which acetals will hereinafter be referred to sometimes as compound (I-4')] such as compound (I-4-1), compound (I-4-2), compound (I-4-3), compound (I-4-4), compound (I-4-5) and compound (I-4-6). The compound (I-4-7) can be obtained by the same reaction and workup procedures as those described hereinbefore for the conversion of compound (I-2-1) or compound (I-2-2) to compound (I-2-3) or compound (I-2-4) except that, in lieu of compound (I-2-1) or (I-2-2), compound (I-4') are subjected to deprotection.

The compound (I-4-5) or compound (I-4-6) can be acylated in the same manner as for the conversion of compound (I-3-2) to compound (I-3-3) to thereby give a compound (I-4-1) or compound (I-4-2). Moreover, compound (I-4-7) can be acetalized, for example in the same manner as for the conversion of compound (I-2-3) or (I-2-4) to a pregnane derivative of general formula (I-2) wherein $X^1$ and $X^2$ jointly represent a lower alkylenedioxy group, to give a compound of general formula (I-4') wherein $Y^1$ and $Y^2$ jointly represent a lower alkylenedioxy group.

The conversion of compound (I-4-4) to compound (I-5-1) is accomplished by reacting the compound (I-4-4) with a reducing agent such as lithium aluminum hydride, zinc borohydride or the like. The amount of the reducing agent is generally about 0.5 to 20 moles per mole of compound (I-4-4). This reduction reaction is preferably conducted in an ether solvent, such as tetrahydrofuran, 1,2-dimethoxyethane, diethyl ether, etc., at a temperature of about 25° to 120° C., and the preferred proportion of such ether solvent is about 20 to 2,000-fold by weight based on compound (I-4-4). This reaction can be advantageously conducted by adding a solution of compound (I-4-4) in an ether solvent gradually to a mixture of said reducing agent and ether solvent at room temperature and refluxing the mixture for a period ranging from about 10 minutes to about 2 hours.

From the reaction mixture thus obtained by the above reduction reaction, the product compound (I-5-1) can be separated and purified by the following and other procedures. Thus, water is gradually added to the reaction mixture to decompose the excess reducing agent and, then, the ether solvent is distilled off under reduced pressure. To the residue is added cold hydrochloric acid, followed by extraction with methylene chloride or chloroform. The extract is washed with aqueous sodium chloride solution and the solvent is distilled off under reduced pressure. Finally the residue is subjected to a purification procedure such as chromatography, recrystallization, etc. to recover the compound (I-5-1).

$1\alpha,3\beta$-Dihydroxypregna-5,7-diene-20-carbaldehyde of formula (I-5-2) can be produced by the same reaction and workup procedures as those described hereinbefore for the conversion of compound (I-2-1) or compound (I-2-2) to compound (I-2-3) or compound (I-2-4) except that, in lieu of compound (I-2-1), compound (I-5-1) is subjected to deprotection reaction.

The conversion of compound (I-2-2) to compound (I-6-1) can be achieved by contacting the compound (I-2-2) with a reducing agent such as sodium borohydride, zinc borohydride or the like. The amount of the reducing agent is generally about 0.25 to 2.0 moles and preferably about 0.8 to 1.2 moles per mole of compound (I-2-2). This reduction reaction is generally conducted in an alcohol solvent, such as methanol, ethanol, etc., an ether solvent, such as tetrahydrofuran, 1,2-dimethoxyethane, etc., or a mixture of such solvents at a temperature within the range of about 0° to 40° C. The proportion of the solvent is generally about 10 to 100-fold by weight based on compound (I-2-2). This reaction can be advantageously conducted by dissolving compound (I-2-2) in a solvent, adding the reducing agent gradually to the solution with stirring and cooling at about 0° C., and stirring the mixture further at a temperature of about 0° C. for a period ranging from about 10 minutes to about 5 hours.

From the reaction mixture thus obtained by the above reduction reaction, the product compound (I-6-1) can be separated and purified by the following and other procedures. To the reaction mixture are added water and a small amount of cold diluted hydrochloric acid in succession, followed by extraction with methylene chloride. The extract is washed successively with aqueous sodium hydrogen carbonate solution and aqueous sodium chloride solution and the solvent is distilled off under reduced pressure. The residue is finally purified, for example by chromatography, recrystallization, etc., to recover the compound (I-6-1).

The conversion of compound (I-6-1) to compound (I-7-1) can be accomplished by reacting the compound (I-6-1) with a peracid such as m-chloroperbenzoic acid, perbenzoic acid or the like. The proportion of the peracid is generally about 1 to 2 moles per mole of compound (I-6-1). This $4\alpha,5\alpha$-epoxidation reaction is generally conducted in an inert solvent, such as methylene chloride, chloroform, etc., in the presence or absence of a saturated aqueous solution of sodium hydrogen carbonate. The proportion of the solvent is generally about 10 to 200-fold by weight based on compound (I-6-1) and the proportion of the aqueous sodium hydrogen carbonate is generally not more than about 200-fold by weight based on compound (I-6-1). This reaction is preferably carried out by dissolving or suspending compound (I-6-1) in an organic solvent, adding said peracid gradually at a temperature ranging from 0° to 40° C., preferably from 15° to 30° C., preferably in the presence of a saturated aqueous solution of sodium hydrogen carbonate, the proportion of which is about 10 to 20-fold by weight based on compound(I-6-1), and then stirring the mixture at room temperature for a period ranging from about 1 to 12 hours.

From the reaction mixture thus obtained by the above epoxidation reaction, the product compound (I-7-1) can be separated and purified by the following and other procedures. The reaction mixture is subjected to phase separation and the aqueous layer is extracted with an organic solvent such as diethyl ether, ethyl acetate, methylene chloride, and so on. The organic layer is combined with this extract and the mixture is washed successively with water, aqueous potassium iodide solution, aqueous sodium thiosulfate solution, water, aqueous sodium hydrogen carbonate solution, and aqueous sodium chloride solution to remove the excess peracid and byproduct acid such as m-chlorobenzoic acid, benzoic acid and so on. Then, the solvent is distilled off under reduced pressure to recover the compound (I-7-1) as a crude product. This crude product is recrystallized to give a pure product of compound (I-7-1). The crude product of compound (I-7-1) can be directly submitted, without purification, to the conversion reaction for the synthesis of compound (I-7-2) or compound (I-7-3).

The conversion of compound (I-7-1) to compound (I-8-1) can be accomplished by reacting the compound (I-7-1) with Collins reagent. The Collins reagent can be prepared by dissolving about 1 to 20-fold by weight, based on chromium oxide, of pyridine in not more than about 20-fold by weight, based on chromium oxide, of an inert solvent such as methylene chloride, chloroform or the like, and adding chromium oxide gradually thereto under ice-cooling and stirring. The proportion of Collins reagent is about 1 to 50 moles, preferably 2 to 20 moles, per mole of compound (I-7-1). This oxidation reaction is generally conducted in an inert solvent such as methylene chloride, chloroform, etc. and the proportion of such solvent is about 10 to 200-fold by weight based on compound (I-7-1). This reaction is preferably conducted by dissolving the compound (I-7-1) in a solvent, adding the resulting solution to a suspension of Collins reagent with stirring at a temperature within the range of −20° C. to 40° C., preferably −10° C. to 20° C., and then stirring the mixture for about 0.5 to 12 hours, preferably for 0.5 to 3 hours. It is expedient, for all practical purposes, to prepare Collins reagent in the solvent and subsequently carry out the reaction with compound (I-7-1) in the resulting solution.

From the reaction mixture thus obtained by the above oxidation reaction, the product compound (I-7-2) can be separated and purified by the following and other procedures. The reaction mixture is diluted with ethyl acetate and filtered with the aid of Celite. The filtrate is then washed with water, aqueous copper sulfate solution, water, aqueous sodium hydrogen carbonate solution and aqueous sodium chloride solution in that order. The resulting solution is concentrated and the concentrate is purified by recrystallization to recover compound (I-7-2). The crude product of compound (I-7-2) may be directly subjected, without purification, to the reaction for conversion to compound (I-7-3) or (I-8-1).

The conversion of compound (I-7-2) to compound (I-8-1) can be accomplished by contacting the compound (I-7-2) with a reducing agent such as lithium aluminum hydride, sodium bis(methoxyethoxy)aluminum hydride, lithium borohydride and so on. The proportion of the reducing agent is generally about 0.75 to 5 moles and preferably about 0.8 to 2.5 moles per mole of compound (I-7-2). This reduction reaction is generally conducted in an inert solvent which may be an ether solvent such as tetrahydrofuran, diethyl ether and so on. The proportion of this solvent is about 10 to 200-fold by weight based on compound (I-7-2). This reaction is preferably carried out by dissolving compound (I-7-2) in a solvent, adding the resulting solution gradually to a solution of the reducing agent under stirring at a temperature within the range of −20° to 80° C., preferably −10° to 40° C., and stirring the mixture at a temperature within the range of 10° to 40° C. for 0.5 to 12 hours.

From the reaction mixture thus obtained by the above reduction reaction, the product compound (I-8-1) can be separated and purified by the following and other procedures. The reaction mixture is diluted with ether and the excess reducing agent is decomposed with a saturated aqueous solution of sodium sulfate, followed by filtration with the aid of Celite. The filtrate thus obtained is concentrated and the concentrate is recrystallized from ethyl acetate to give the desired compound (I-8-1).

The compound (I-7-3) can be produced by subjecting compound (I-7-1) to Mitsunobu reaction to cause a steric inversion of the 3-hydroxyl group and, if necessary, further to hydrolysis and protective group exchange reaction.

The conversion of compound (I-7-1) to a compound of general formula (I-7-3) wherein $Z^3$ is an acyl group [which will hereinafter be referred to sometimes as compound (I-7-3a)] is accomplished by reacting compound (I-7-1) with a carboxylic acid having the corresponding acyl group in the presence of a tertiary phosphine, such as triphenylphosphine etc., and an azodicarboxylic acid lower alkyl ester, such as diethyl azodicarboxylate or the like. The proportion of said tertiary phosphine is about 1 to 3 moles, preferably about 1.5 to 2 moles, per mole of compound (I-7-1). The proportion of said carboxylic acid is about 1 to 3 moles, preferably about 0.9 to 1.2 moles, per mole of compound (I-7-1). The proportion of said azodicarboxylic acid lower alkyl ester is about 1 to 3 moles, preferably about 1.5 to 2 moles, per mole of compound (I-7-1). This reaction is generally conducted in an inert solvent which may be an aromatic hydrocarbon such as toluene, benzene, etc. or an ether solvent such as tetrahydrofuran, diethyl ether and so on. The proportion of such solvent is about 10 to 200-fold by weight based on compound (I-7-1). The reaction can be advantageously carried out by adding said azodicarboxylic acid lower alkyl ester gradually to a solution or suspension of compound (I-7-1), tertiary phosphine and carboxylic acid at a temperature of −10° to 80° C., preferably 0° to 30° C., and stirring the mixture for 0.5 to 12 hours.

From the reaction mixture thus obtained, the product compound (I-7-3a) can be separated and purified by the following and other procedures. The reaction mixture is diluted with water and extracted with a solvent such as diethyl ether, ethyl acetate, etc. and the extract is washed with aqueous sodium chloride solution and so on. The solvent is then distilled off from the solution under reduced pressure and the residue is purified, for example by chromatography, recrystallization, etc., to recover the compound (I-7-3a).

The compound (I-7-3a) can be reacted with a basic substance, such as potassium carbonate, sodium carbonate, sodium hydroxide, potassium hydroxide, etc., in an alcohol solvent, such as ethanol, methanol, etc., to give a compound of general formula (I-7-3) wherein $Z^3$ is a hydrogen atom [which compound will hereinafter be referred to sometimes as compound (I-7-3b)]. The amount of said basic compound is generally 0.05 to 3 moles and preferably 0.1 to 1.5 moles per mole of compound (I-7-3a). This deprotection reaction is generally carried out at a temperature within the range of 0° to 40° C.

From the reaction mixture thus obtained, the compound (I-7-3b) can be recovered by the following and other procedures. The reaction mixture is diluted with water and extracted with a solvent such as diethyl ether, ethyl acetate, etc. and the extract is washed successively with water, aqueous sodium hydrogen carbonate solution and aqueous sodium chloride solution. The solvent is then distilled off under reduced pressure and the residue is purified, for example by recrystallization, to recover the compound (I-7-3b).

The compound (I-7-3b) can also be produced by reducing the compound (I-7-2). For example, this reduction can be carried out by contacting compound (I-7-2) with a reducing agent such as sodium borohydride. The proportion of the reducing agent is generally about 0.25 to 2.0 moles, preferably about 0.8 to 1.2 moles, per mole of compound (I-7-2). This reduction reaction is generally conducted in an alcohol solvent such as ethanol, methanol, etc., and the proportion of such solvent is generally about 10 to 100-fold by weight based on compound (I-7-2). The reaction temperature is generally in the range of about 0° to 40° C. This reaction can be advantageously carried out by dissolving compound (I-7-2) in a solvent, adding said reducing agent gradually thereto under stirring and cooling at about 0° C., and stirring the mixture at a temperature of about 0° C. for a period ranging from about 10 minutes to about 5 hours.

From the reaction mixture thus obtained by the above reduction reaction, the compound (I-7-3b) can be separated and purified by the following and other procedures. To the reaction mixture is added diluted hydrochloric acid under ice-cooling to decompose the excess reducing agent, followed by dilution with water. The resulting dilution is then extracted with an organic solvent such as ether, ethyl acetate, methylene chloride, etc. and the extract is washed with cold aqueous sodium hydrogen carbonate solution and aqueous sodium chloride solution in that order. The solvent is then distilled off under reduced pressure and the residue is purified by recrystallization to recover the compound (I-7-3b). The crude compound (I-7-3b) may be directly subjected, without prior purification, to the next reaction.

The 3β-hydroxyl group of compound (I-7-3b) can be protected to give a compound of general formula (I-7-3) wherein $Z^3$ is a lower alkoxycarbonyl group, an N-lower alkylcarbamoyl group, an N-arylcarbamoyl group or an N,N-di(lower alkyl)carbamoyl group [which compound will hereinafter be referred to sometimes as compound (I-7-3c)] and a compound of general formula (I-7-3) wherein $Z^3$ is a tri-substituted silyl group or an alkoxymethoxy group which may optionally substituted [which compound will hereinafter be referred to sometimes as compound (I-7-3c)]. Protection of the 3β-hydroxyl group can be accomplished by the conventional procedure known for protection of hydroxyl groups.

The conversion of each of compound (I-7-3a), compound (I-7-3b) and compound (I-7-3c) [which will hereinafter be collectively referred to sometimes as compound (I-7-3a-c)] to compound (I-8-1) can be accomplished by contacting compound (I-7-3a-c) with a reducing agent such as lithium aluminum hydride, sodium bis(methoxyethoxy)aluminum hydride, lithium tri-sec-butylborohydride, lithium borohydride and so on. The proportion of the reducing agent is generally about 0.75 to 5 moles and preferably about 0.8 to 2.5 moles per mole of compound (I-7-3a-c). This reduction reaction is generally conducted in an inert solvent which may be an ether solvent such as tetrahydrofuran, diethyl ether and so on. The proportion of this solvent is about 10 to 200-fold by weight based on compound (I-7-3a-c). This reaction can be advantageously carried out by dissolving compound (I-7-3a-c) in a solvent, adding the resulting solution gradually to a solution or suspension of the reducing agent with stirring at a temperature of $-20°$ to 80° C., preferably $-10°$ to 40° C., and stirring the resulting mixture further at a temperature in the range of 10° to 40° C. for 0.5 to 12 hours.

From the reaction mixture thus obtained by the above reduction reaction, the compound (I-8-1) can be separated and purified by the following and other procedures. The reaction mixture is diluted with ether and the excess reducing agent is decomposed with a saturated aqueous solution of sodium sulfate, followed by filtration with the aid of Celite. The filtrate is concentrated and the concentrate is recrystallized from ethyl acetate to recover the desired compound (I-8-1).

The conversion of compound (I-8-1) to a compound of general formula (I-8-2) wherein $Z^3$ is an acyl group, a lower alkoxycarbonyl group, an N-lower alkylcarbamoyl group, an N-arylcarbamoyl group or an N,N-di(lower alkyl)carbamoyl group [which compound will hereinafter be referred to sometimes as compound (I-8-2a)] can be accomplished by reacting compound (I-8-1) with an esterifying agent in the presence of a basic compound such as pyridine, triethylamine and so on. The esterifying agent is exemplified by lower alkyl halocarbonates such as methyl chlorocarbonate, ethyl chlorocarbonate, propyl chlorocarbonate, butyl chlorocarbonate, methyl bromocarbonate, ethyl bromocarbonate, etc.; carboxylic acid anhydrides including lower alkanoic acid anhydrides such as acetic anhydride, propionic anhydride, butyric anhydride, valeric anhydride, etc. and aromatic carboxylic acid anhydrides such as benzoic anhydride etc.; carboxylic acid halides including lower alkanoic acid halides such as acetyl chloride, propionyl chloride, butyryl chloride, valeryl chloride, etc. and aromatic carboxylic acid halides such as benzoyl chloride, p-methylbenzoyl chloride, naphthoyl chloride, etc.; N,N-di(lower alkyl)carbamoyl halides such as N,N-dimethylcarbamoyl chloride, N,N-diethylcarbamoyl chloride, N,N-dipropylcarbamoyl chloride, etc.; lower alkyl isocyanates such as methyl isocyanate, ethyl isocyanate, propyl isocyanate, etc.; and aryl isocyanates such as phenyl isocyanate, tolyl isocyanate and so on. Where an alkyl halocarbonate is used as the esterifying agent, there is produced a compound of general formula (I-8-2) wherein $Z^3$ is a lower alkoxycarbonyl group Where a carboxylic acid anhydride or a carboxylic acid halide is used as the esterifying agent, there is produced a compound of general formula (I-8-2) wherein $Z^3$ is an acyl group. Where the esterifying agent is an N,N-di(lower alkyl)-carbamoyl halide, there is produced a compound of formula (I-8-2) in which $Z^3$ is an N,N-di(lower alkyl)-carbamoyl group. Where a lower alkyl isocyanate is used as the esterifying agent, there is produced a compound of general formula (I-8-2) wherein $Z^3$ is an N-lower alkylcarbamoyl group. The use of an aryl isocyanate as the esterifying agent gives rise to a compound of general formula (I-8-2) wherein $Z^3$ is an N-arylcarbamoyl group. The amount of the esterifying agent is generally about 1.0 to 5 moles per mole of compound (I-8-1). Where the esterifying agent is an alkyl halocarbonate, a carboxylic acid anhydride, a carboxylic acid halide or an N,N-di(lower alkyl)carbamoyl halide, the basic compound is generally used in a proportion of about 2 to 40 moles per mole of compound (I-8-1) and preferably in a proportion of not less than about 2 moles per mole of the esterifying agent. It is preferable that a catalyst such as 4-(N,N-dimethylamino)pyridine, 4-pyrrolidinopyridine or the like be present in the reaction system in an amount ranging from about 0.001 to 0.1 mole per mole of compound (I-8-1). Where the esterifying agent is a lower alkyl isocyanate or an aryl isocyanate, the basic compound is generally used in a proportion of about 0.0001 to 10 moles per mole of compound (I-8-1). These esterification reactions are generally conducted at a temperature of about 0° to 100° C. This esterification reaction may be conducted in a solvent such as methylene chloride, chloroform, diethyl ether, benzene, toluene and so on, and the amount of such solvent is generally not more than about 200-fold by weight based on compound (I-8-1). The reaction can be advantageously carried out by adding said esterifying agent gradually to a mixture of said compound (I-8-1) and basic compound, if desired plus said catalyst, or a solution thereof in said solvent, under cooling at about 0° C. and, then, stirring the mixture at a temperature of about 0° to 100° C. for a period of about 10 minutes to about 12 hours.

From the reaction mixture thus obtained by the above esterification reaction, the product compound (I-8-2a) can be separated and purified by the following and other procedures. The reaction mixture is poured in cold diluted hydrochloric acid, followed by extraction with methylene chloride. The extract is washed with aqueous sodium hydrogen carbonate solution and aqueous sodium chloride solution in that order and the solvent is then distilled off. If necessary, the residue is further purified by recrystallization or column chromatography to recover the desired compound (I-8-2a).

The conversion of compound (I-8-1) to a compound of general formula (I-8-2) wherein $Z^3$ is a tri-substituted silyl group or an alkoxymethyl group which may optionally be substituted [which compound will hereinafter be referred to sometimes as compound (I-8-2b)] is accomplished by reacting compound (I-8-1) with a tri-substituted silyl halide, such as trimethylsilyl chloride, t-butyldimethylsilyl chloride, t-butyldiphenylsilyl chloride, tribenzylsilyl chloride, triisopropylsilyl chloride, etc., or an alkoxymethyl chloride, such as methoxymethyl chloride, methoxyethoxymethyl chloride, etc., in the presence of a basic substance or alternatively with a vinyl ether compound, such as ethyl vinyl ether, 3,4-dihydropyran, methyl isopropenyl ether, etc., in the presence of an acid catalyst.

In the above protection reaction using a tri-substituted silyl halide or an alkoxymethyl chloride, the proportion of the tri-substituted silyl halide is 0.9 to 10 moles and preferably 1.0 to 2.5 moles per mole of compound (I-8-1), and the proportion of the alkoxymethyl chloride is also in the range of 0.9 to 10 moles and preferably 1.0 to 2.5 moles per mole of compound (I-8-1). As examples of said basic substance, there may be mentioned various organic bases such as pyridine, triethylamine, etc., metal hydrides such as sodium hydride, potassium hydride, etc., and organometallic compounds such as methyllithium, butyllithium, phenyllithium and so on. The proportion of said basic substance is generally 0.9 to 50 moles and preferably 1.0 to 20 moles per mole of compound (I-8-1). This protection reaction may be conducted in the presence of a solvent. The solvent mentioned just above is a solvent which does not interfere with the reaction and includes tetrahydrofuran, diethyl ether, N,N-dimethylformamide, dimethyl sulfoxide, methylene chloride and so on. The amount of the solvent is about 10 to 200-fold by weight based on compound (I-8-1). This reaction can be advantageously carried out by adding a tri-substituted silyl halide or an alkoxymethyl chloride to a mixture of said compound (I-8-1), basic substance and solvent and, then, stirring the resulting mixture at 0° to 80° C. for 1 to 12 hours. However, it is preferable that said mixture of compound (I-8-1), basic substance
and solvent be stirred at −20° C. to 80° C., where a metal hydride is used as the basic substance, or at −100° to 0° C., where an organometallic compound is used, for 0.5 to hours before proceeding with the reaction with the tri-substituted silyl halide or alkoxymethyl chloride. From the reaction mixture thus obtained, the product compound (I-8-2b) can be separated and purified by the following and other procedures. The reaction mixture is first poured in water, followed by extraction with ether or the like. The resulting extract is washed successively with cold diluted hydrochloric acid, water, aqueous sodium hydrogen carbonate solution and aqueous sodium chloride solution and the solvent is distilled off. If necessary, the residue is purified, for example by recrystallization, column chromatography, etc., to recover the desired compound (I-8-2b).

In the protection reaction of compound (I-8-1) with a vinyl ether compound, the proportion of the vinyl ether compound is generally 0.8 to 50 moles and preferably 1.1 to 20 moles per mole of compound (I-8-1). The aforementioned acid catalyst is exemplified by sulfonic acids such as p-toluenesulfonic acid, etc.; salts of sulfonic acids such as pyridinium p-toluenesulfonate, etc.; inorganic acids such as hydrochloric acid, etc.; phosphorus oxychloride; and so on. The proportion of said acid catalyst is generally 0.01 to 2 moles and preferably 0.05 to 0.2 mole per mole of compound (I-8-1). This reaction may be conducted in a solvent, which should be a solvent that does not interfere with the reaction and may for example be methylene chloride, chloroform or benzene. The proportion of the solvent is generally 10 to 1,000-fold by weight based on compound (I-8-1). This reaction is carried out by mixing the compound (I-8-1) with the vinyl ether compound, adding the solvent if desired, further adding the acid catalyst at a temperature within the range of −10° to 30° C., and finally stirring the mixture at −10° to 60° C. for 5 minutes to 24 hours. From the reaction mixture thus obtained, the product compound (I-8-2b) can be separated and purified by the following and other procedures. The reaction mixture is diluted with ether and washed with aqueous sodium hydrogen carbonate solution and aqueous sodium chloride solution. The solvent is then distilled off and, if necessary, the residue is purified, for example by recrystallization, chromatography, etc. to recover the desired compound (I-8-2b).

The compound (I-8-2b) can also be obtained by reduction of compound (I-7-3c). The conversion of compound (I-7-3c) to compound (I-8-2b) can be accomplished by the same reaction and workup procedures as those described for the conversion of compound (I-7-3a-c) to compound (I-8-1) except that compound (I-7-3d) in lieu of compound (I-7-3a-c) is subjected to reduction.

The conversion of compound (I-8-2) to a compound of general formula (I-8-3) wherein $Z^4$ is an acyl group, a lower alkoxycarbonyl group, an N-lower alkylcarbamoyl group, an N-arylcarbamoyl group or an N,N-di(lower alkyl)carbamoyl group [which compound will hereinafter be referred to sometimes as compound (I-8-3a)] can be accomplished by the same reaction and workup procedures as those described for the conversion of compound (I-8-1) to compound (I-8-2a) except that compound (I-8-2) in lieu of compound (I-8-1) is subjected to esterification.

The conversion of compound (I-8-2) to a compound of general formula (I-8-3) wherein $Z^4$ is a tri-substituted silyl group or an alkoxymethyl group which may optionally be substituted [which compound will hereinafter be referred to sometimes as compound (I-8-3b)] can be accomplished by the same reaction and workup procedures as those described for the conversion of compound (I-8-1) to compound (I-8-2b) except that compound (I-8-2) in lieu of compound (I-8-1) is protected.

The compound (I-8-3) can be produced from compound (I-8-1) without isolation of the intermediate compound (I-8-2).

The conversion of compound (I-8-3) to compound (I-5-3) is accomplished by subjecting compound (I-8-3) to dehydration reaction in the presence of an acid catalyst. This dehydration reaction can be carried out, for example by contacting compound (I-8-3) with an acid such as an inorganic acid, e.g. sulfuric acid, hydrochloric acid, etc., an organic acid, e.g. formic acid, acetic acid, propionic acid, monochloroacetic acid, dichloroacetic acid, etc., a sulfonic acid, e.g. p-toluenesulfonic acid, camphorsulfonic acid, etc. or a sulfonic acid salt, e.g. pyridinium p-toluenesulfonate, etc., in an organic solvent such as dimethyl carbonate, diethyl carbonate, tetrahydrofuran, dioxane, toluene, benzene, ethyl acetate, butyl acetate, etc. at a temperature which may range from about 0° to 150° C. The amount of such acid is dependent on its species but is generally about 0.01 to 50 moles per mole of compound (I-8-3). The amount of the solvent is generally about 10 to 100-fold by weight based on compound (I-8-3). This reaction can be carried out by dissolving compound (I-8-3) in said solvent, adding said acid and stirring the mixture at a temperature of about 0° to 150° C. for 5 minutes to 24 hours.

From the reaction mixture thus obtained by the above dehydration reaction, the product compound (I-5-3) can be separated and purified by the following and other procedures. The reaction mixture is poured in ice-water and extracted with ether. The extract is neutralized with aqueous sodium hydroxide solution, aqueous sodium hydrogen carbonate solution of the like and washed with aqueous sodium chloride solution. The solvent is then distilled off and, if necessary, the residue is purified by recrystallization, column chromatography, etc., to recover the desired compound (I-5-3).

The conversion of compound (I-8-3) to compound (I-9-1a) is accomplished by reacting compound (I-8-3) with a carbonic acid di-lower alkyl ester in the presence of an organic acid such as formic acid, acetic acid, propionic acid, monochloroacetic acid and so on. The carbonic acid di-lower alkyl ester may for example be dimethyl carbonate, diethyl carbonate, dipropyl carbonate or the like and its proportion is generally about 10 to 200-fold by weight based on compound (I-8-3). The proportion of said organic acid is generally about 0.1 to 10-fold by weight based on compound (I-8-3). The reaction temperature is preferably in the range of about 50° to 150° C. This rearrangement-carbonic esterification reaction can be carried out by dissolving compound (I-8-3) in said carbonic acid di-lower alkyl ester, adding said organic acid thereto, and heating the mixture at about 50° to 150° C. for 1 to 48 hours.

From the reaction mixture thus obtained, the product compound (I-9-1a) can be separated and purified by the following and other procedures. The reaction mixture is poured in cold water and extracted with diethyl ether. The extract is washed successively with cold aqueous sodium hydroxide solution, aqueous sodium hydrogen carbonate solution and aqueous sodium chloride solution, and the solvent is distilled off. The residue is purified by recrystallization or column chromatography to recover the desired compound (I-9-1a).

The conversion of compound (I-9-1a) to compound (I-9-1b) can be accomplished by the same reaction and workup procedures as those described for the conversion of compound (I-7-3a) to compound (I-7-3b) except that compound (I-9-1a) in lieu of compound (I-7-3a) is subjected to deprotection.

The conversion of compound (I-9-1b) to compound (I-9-1c) can be accomplished by the same reaction and workup procedures as those described for the conversion of compound (I-8-1) to compound (I-8-2a) except that compound (I-9-1b) in lieu of compound (I-8-1) is subjected to esterification.

The compound (I-5-3) can be produced by reacting compound (I-9-1a) or compound (I-9-1c) in the presence of a palladium compound. Examples of the palladium compound include tris(dibenzylideneacetone)-dipalladium(chloroform), palladium acetate, palladium nitrate, palladium chloride, bis(acetylacetonato)palladium, tetrakis(triphenylphosphine)palladium, and so on. The proportion of the palladium compound is generally about 0.01 to 0.5 mole per mole of compound (I-9-1a) or (I-9-1c). The palladium atom derived from this palladium compound is preferably present as coordinated by a tertiary phosphine in the reaction system and, therefore, a tertiary phosphine may be added to the reaction system as necessary. The tertiary phosphine may for example be tributylphosphine, triethylphosphine, triphenylphosphine, tritolylphosphine, 1,2-bis(diphenylphosphino)ethane or the like and its proportion is generally about 1 to 20 moles per mole of the palladium compound. The reaction temperature is generally in the range of about 20° to 150° C. Preferred examples of the solvent are ether solvents such as 1,4-dioxane, tetrahydrofuran and so on. The amount of the solvent is preferably about 5 to 500-fold by weight based on compound (I-9-1a) or (I-9-1c). The reaction can be advantageously conducted by stirring a solution of the palladium compound and, if used, the tertiary phosphine in said ether solvent for about 5 to 60 minutes at room temperature in an inert atmosphere such as argon gas or nitrogen gas, then adding a solution of compound (I-9-1a) or (I-9-1c) in the same ether solvent as above, and stirring the mixture under reflux for about 1 to 24 hours.

From the reaction mixture thus obtained, the product compound (I-5-3) can be separated and purified by the following and other procedures. The reaction mixture is filtered with the aid of Florisil, the filtrate is concentrated under reduced pressure, and the concentrate is purified by chromatography, recrystallization or the like to recover the desired compound (I-5-3).

The conversion of compound (I-5-3) to compound (I-5-4a) can be accomplished by reacting compound (I-5-3) with a lower alkanone, such as acetone, 2-butanone, 3-pentanone, etc., in the presence of about 0.001 to 0.1 mole, based on mole of compound (I-5-3), of an acid, such as p-toluenesulfonic acid, pyridinium p-toluenesulfonate, sulfuric acid, hydrochloric acid, copper sulfate, etc., at a temperature of about 20° to 80° C. or by subjecting compound (I-5-3) to hydrolysis in the presence of about 0.01 to 5 moles, based on each mole of compound (I-5-3), of an acid, such as hydrochloric acid, acetic acid, p-toluenesulfonic acid, copper sulfate, etc., at a temperature of about $-10°$ to 60° C. The amount of said lower alkanone is generally about 10 to 1,000-fold by weight based on compound (I-5-3). In the case of hydrolysis reaction, water is generally used in a proportion of about 10 to 200-fold by weight based on compound (I-5-3). In the latter case, it is preferable that a water-miscible organic solvent such as tetrahydrofuran, 1,2-dimethoxyethane, methanol, ethanol, etc. be concomitantly present in the reaction system. The preferred amount of such organic solvent is about 20 to 100-fold by weight based on compound (I-5-3).

From the deprotection reaction mixture thus obtained, the product compound (I-5-4a) can be separated and purified by the following and other procedures. The lower alkanone, organic solvent, etc. used for the reaction are first distilled off and the residue is diluted with water and extracted with an organic solvent such as methylene chloride, diethyl ether or the like. The extract is washed successively with water, aqueous sodium hydrogen carbonate solution and aqueous sodium chloride solution and the solvent is distilled off under reduced pressure. The residue is then purified by chromatography, recrystallization or the like to recover the desired compound (I-5-4a).

The compound (I-5-4a) can be subjected to deprotection reaction to give a pregnane derivative of general formula (I-5-4b), general formula (I-5-4c) or formula (I-5-2). Moreover, compound (I-5-3) can be subjected to deprotection reaction to give compound (I-5-1). These deprotection reactions can be carried out by the conventional procedure for converting an organic compound having a protected hydroxyl group to an organic compound having a free hydroxy group.

The pregnane derivative (I-5) having a free hydroxyl group in the 1α-position and/or in the 3β-position, such as compound (I-5-1), compound (I-5-2), compound (I-5-4a), compound (I-5-4b) and compound (I-5-4c), can be subjected to protection reaction, for example in the same manner as for the conversion of compound (I-8-1) to compound (I-8-2) or (I-8-3), to thereby protect the free hydroxy group or groups.

The pregnane derivative of general formula (I-6), (I-7), (I-8) or (I-9) wherein $X^1$ and $X^2$ each is a lower alkoxyl group or jointly represent a lower alkylenedioxy group, such a compound (I-6-1), compound (I-7-1), compound (I-7-2), compound (I-7-3), compound (I-8-1), compound (I-8-2), compound (I-8-3), compound (I-9-1a), compound (I-9-1b) and compound (I-9-1c), can be subjected to deprotection reaction to give a pregnane derivative of general formula (I-6), (I-7), (I-8) or (I-9) wherein $X^1$ and $X^2$ jointly represent an oxo group. For example, a pregnane derivative of general formula (I-6), (I-7), (I-8) or (I-9) wherein $X^1$ and $X^2$ each is a lower alkoxyl group or jointly represent a lower alkylenedioxy group can be converted to the corresponding aldehyde by the same reaction and workup procedures described for the conversion of compound (I-5-3) to compound (I-5-4a) except that said derivative in lieu of compound (I-5-3) is subjected to deprotection.

The pregnane derivative of general formula (I-6), (I-7), (I-8) or (I-9) wherein $X^1$ and $X^2$ jointly represent an oxo group can be converted to a pregnane derivative of general formula (I-6), (I-7), (I-8) or (I-9) wherein $X^1$ and $X^2$ jointly represent a lower alkylenedioxy group by reacting the starting pregnane derivative with a lower alkylene acetal of a ketone, such as 2-butanone (2,2-dimethyltrimethylene) acetal, in an organic solvent, such as benzene, toluene, etc., in the presence of an acid catalyst, such as pyridinium p-toluenesulfonate, etc., under reflux conditions.

The pregnane derivative of general formula (I-5) wherein $A^6$ is in the β-configuration and represents an acyloxy group, a lower alkoxycarbonyloxy group, an N-lower alkylcarbamoyloxy group, an N-arylcarbamoyloxy group, an N,N-di(lower alkyl)carbamoyloxy group, a tri-substituted silyloxy group or an alkoxymethoxy group which may optionally be substituted; $D^{12}$ is in the α-configuration and represents an acyloxy group, a lower alkoxycarbonyloxy group, an N-lower alkylcarbamoyloxy group, an N-arylcarbamoyloxy group, an N,N-di(lower alkyl)carbamoyloxy group, a tri-substituted silyloxy group or an alkoxymethoxy group which may optionally be substituted; and $X^1$ and $X^2$ jointly represent an oxo group [which derivative will hereinafter be referred to sometimes as compound (I-5')] can also be derived from a pregnane derivative of general formula (I-8) wherein $A^9$ means the same group as $A^6$ in general formula (I-5) representing the compound (I-5'); $D^{13}$ means the same group as $D^{12}$ in general formula (I-5) representing the compound (I-5') and $X^1$ and $X^2$ jointly represent an oxo group [which derivative will hereinafter be referred to sometimes as compound (I-8')] or a pregnane derivative of general formula (I-9) wherein $A^{10}$ means the same group as $A^6$ in the general formula (I-5) representing compound (I-5'); $D^{14}$ means the same group as $D^{12}$ in general formula (I-5) representing compound (I-5'), $D^{15}$ is in the α-configuration and represents an acyloxy group, a lower alkoxycarbonyloxy group, an N-lower alkylcarbamoyloxy group, an N-arylcarbamoyloxy group or an N,N-di(lower alkyl)carbamoyloxy group; and $X^1$ and $X^2$ jointly represent an oxo group [which derivative will hereinafter be referred to sometimes as compound (I-9')]. Thus, the compound (I-5') can be produced by the same reaction and workup procedures as described for the conversion of compound (I-8-3) to compound (I-5-3) except that compound (I-8') in lieu of compound (I-8-3) is subjected to dehydration reaction, or by the same reaction and workup procedures described for the conversion of compound (I-9-1a) or (I-9-1c) to compound (I-5-3) except that compound (I-9') in lieu of compound (I-9-1a) or (I-9-1c) is subjected to conjugated diene-forming reaction.

1α,3β-Dihydroxypregna-5,7-diene-20-carbaldehyde of formula (I-5-2) can be converted to 1α-hydroxyvitamin $D_3$ by the following and other processes.

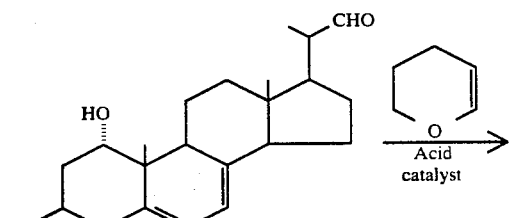
(I-5-2)
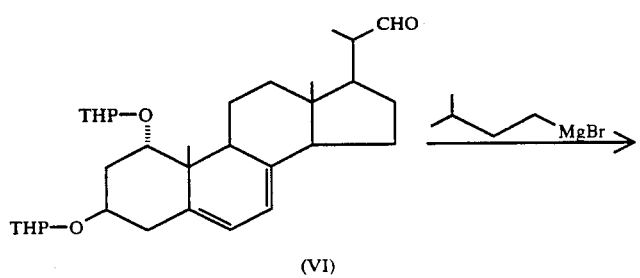
(VI)
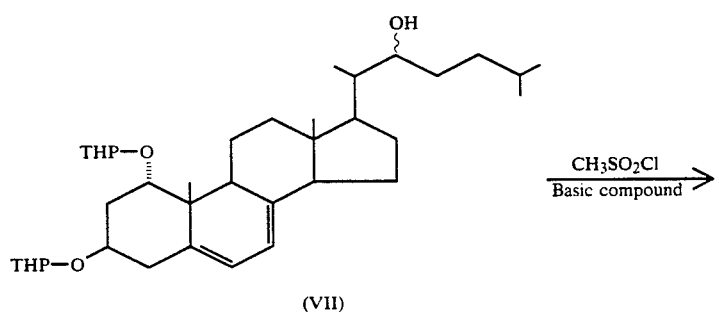
(VII)
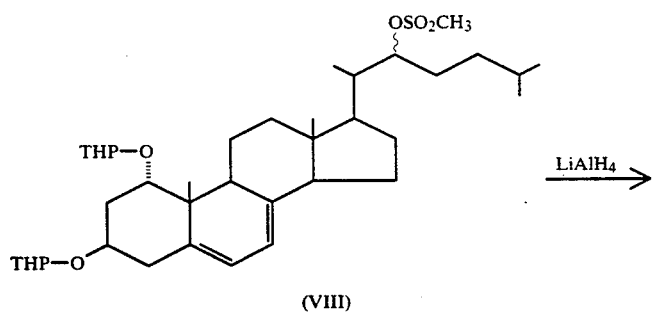
(VIII)
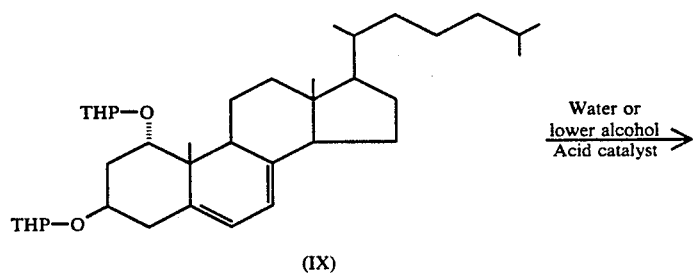
(IX)

-continued

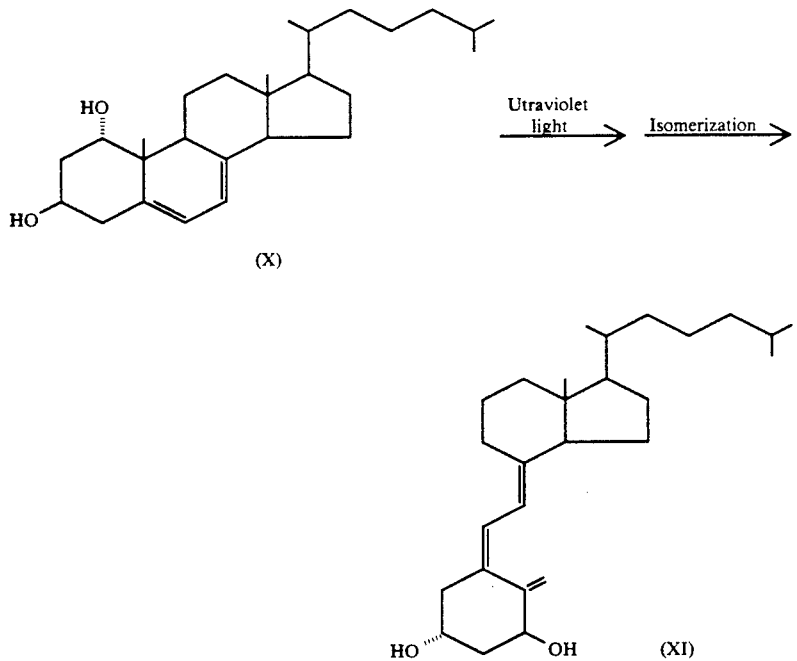

In the above formula, THP, dotted line ( ... ), solid line (—) and wavy line (~) have the meanings defined hereinbefore.

1α,3β-Dihydroxypregna-5,7-diene-20-carbaldehyde of formula (I-5-2) can be converted to the compound of formula (VI) by reacting the aldehyde with 3,4-dihydro-2H-pyran in a solvent such as methylene chloride or the like in the presence of an acid catalyst such as pyridinium p-toluenesulfonate or the like at a temperature ranging from about 0° to 20° C. The compound of formula (VI) is then reacted with isoamylmagnesium bromide in an ether solvent such as diethyl ether, tetrahydrofuran or the like at a temperature of about −10° C. to 70° C. to give a compound of formula (VII). This compound of formula (VII) is reacted with methanesulfonyl chloride in the presence of a basic compound such as pyridine, triethylamine or the like at a temperature of about 0° to 20° C. to give a compound of formula (VIII). This reaction may be conducted in a solvent such as methylene chloride. The compound of formula (VIII) is then reacted with lithium aluminum hydride in an ether solvent such as tetrahydrofuran, 1,2-dimethoxyethane or the like at a temperature ranging from about 20° to 70° C. to give a compound of formula (IX). The compound of formula (IX) is reacted with water or a lower alcohol such as methanol, ethanol or the like in the presence of an acid catalyst such as hydrochloric acid, pyridinium p-toluenesulfonate or the like at a temperature of about 10° to 60° C. to give a compound of formula (X). Then, this compound of formula (X) may for example be irradiated with ultraviolet light in the known manner described in Japanese Patent Application Laid-open No. 52-108964 (1977) and the resulting compound may be isomerized to give 1α-hydroxyvitamin D₃ of formula (XI).

BEST MODE FOR CARRYING OUT THE INVENTION

The examples given hereinafter are further illustrative of the invention. It should be understood that the invention is by no means limited to these specific examples.

EXAMPLE 1

The strain Alcaligenes faecalis D4020-K15 (FERM BP-204) was cultivated in the following manner. Thus, 2.0 g of chenodeoxycholic acid, 0.05 g of glucose, 0.2 g of ammonium nitrate, 0.1 g of potassium dihydrogen phosphate, 0.6 g of potassium monohydrogen phosphate, 0.05 g of magnesium sulfate heptahydrate, 0.05 g of yeast extract, 0.05 g of peptone and 0.2 g of sodium hydroxide were mixed and made up with tap water to make 100 ml (pH 7.5) for use as a culture medium. This medium was put in a 500-ml Sakaguchi flask and sterilized by autoclaving at 120° C. for 15 minutes. A seed culture (5 ml) of the above strain as prepared by overnight cultivation in the same medium as above on a test tube shaker was added into the above 500 ml Sakaguchi flask and shake culture was carried out at 30° C. for 2 days. The resulting culture broth was adjusted to pH 9.0 with 1N-aqueous sodium hydroxide solution and centrifuged to separate the precipitate and microbial cells from the supernatant. The recovered precipitate and cells are mixed with 500 ml of ethyl acetate, followed by centrifugation to separate the ethyl acetate layer from the cells. The ethyl acetate layer was dried over anhydrous sodium sulfate and the ethyl acetate was distilled off under reduced pressure. The procedure gave 1.4 g of 7α-hydroxypregna-1,4-dien-3-one-20-carbaldehyde.

A portion of this 7α-hydroxypregna-1,4-dien-3-one-20-carbaldehyde was taken and dissolved in methanol to give a 1% solution and 25 μl of this solution was injected into a high performance liquid chromatograph equipped with a μ-Bondapak C-18 column (Waters Associates, Inc., U.S., HLC-GPC-244). As the mobile phase, a 25/75 (v/v) mixture of water and methanol preadjusted to pH 4.0 was passed at a flow rate of 1 ml/min. Differential refractometry was used as the detection method. The HPLC peak area was calculated with an integrator (Shimadzu Corporation, Shimadzu Chromatopak C-R3A). The purity of the above 7α-hydroxypregna-1,4-dien-3-one-20-carbaldehyde based on the area ratio was 96.6%.

The identification of 7α-hydroxypregna-1,4-dien-3-one-20-carbaldehyde was made as follows.

Mass spectrum (m/e): 342 [M]+, 324 [M-H$_2$O]+.

$^1$H-NMR spectrum (90 MHz) $\delta_{TMS}^{CDCl_3}$: 0.74 (s, 3 H), 1.06 (d, 3 H), 1.18 (s, 3 H), 3.97 (br, 1 H), 6.08 (d, 1 H), 6.17 (d, 1 H), 7.00 (d, 1 H), 9.55 (d, 1 H).

EXAMPLE 2

The cultivation procedure of Example 1 was repeated except that chenodeoxycholic acid was used in an amount of 1.0 g instead of 2.0 g, that sodium hydroxide was used in an amount of 0.1 g instead of 0.2 g and that the cultivation time was 1 day instead of 2 days. The resulting culture broth was adjusted to pH 9.0 with 1N-aqueous sodium hydroxide solution and centrifuged to separate the cells and the precipitate formed in the course of culture from the supernatant. The precipitate and cells were mixed with 50 ml of water and the mixture was centrifuged to separate the aqueous layer from the insoluble fraction. The insoluble fraction was mixed with 200 ml of methanol and the mixture was centrifuged to separate the cells from the methanol layer. The methanol layer was diluted with 10 ml of water and the methanol was distilled off under reduced pressure. The resulting precipitate was recovered by filtration and dried to give 0.77 g of 7α-hydroxypregna-1,4-dien-3-one-20-carbaldehyde. Determined by high performance liquid chromatography, this product had a purity of 95.1%.

To the 7α-hydroxypregna-1,4-dien-3-one-20carbaldehyde obtained as above was added 10 ml of methanol and the mixture was warmed to obtain a homogenous solution. This solution was diluted with 7 ml of warm water and, then, allowed to cool to room temperature. This procedure yielded 0.62 g pure crystals showing a purity of 98%.

EXAMPLE 3

In 200 ml of benzene were dissolved 5.00 g (14.6 mmoles) of 7α-hydroxypregna-1,4-dien-3-one-20-carbaldehyde and 4.56 g (43.8 mmoles) of 2,2-dimethyl-1,3-propanediol, followed by addition of 100 mg of p-toluenesulfonic acid. The mixture was refluxed for 5 hours, with the byproduct water being constantly removed from the reaction system by means of a Dean-Stark trap. The reaction mixture was cooled to room temperature and washed with aqueous sodium hydrogen carbonate solution. The aqueous layer was extracted with ether-hexane (70:30, v/v) and the extract was combined with the organic layer. This mixture was washed with aqueous sodium chloride solution and dried over magnesium sulfate and the solvent was distilled off under reduced pressure. Finally the residue was purified by silica gel chromatography (eleuent: ethyl acetate-hexane=1:10, v/v) to recover 5.53 g of 20-(5,5-dimethyl-1,3-dioxan-2-yl)pregna-1,4,6-trien-3-one (yield: 92%).

$^1$H-NMR spectrum (90 MHz) $\delta_{TMS}^{CDCl_3}$: 0.70 (s, 3 H), 0.78 (s, 3 H), 1.07 (d, J=6 Hz, 3 H), 1.17 (s, 3 H), 1.19 (s, 3 H), 3.2–3 7 (m, 4 H), 4.38 (d, J=1.5 Hz, 1 H), 5.9–6.2 (m, 3 H), 6.24 (dd, J=10, 1.5 Hz, 1 H), 7.06 (d, J=10 Hz, 1 H).

IR spectrum (KBr): 2940, 2860, 1655, 1605, 1100 cm$^{-1}$.

EXAMPLE 4

In 200 ml of methylene chloride were dissolved 5.00 g (14.6 mmoles) of 7α-hydroxypregna-1,4-dien-3-one-20-carbaldehyde and 4.56 g (43.8 mmoles) of 2,2-dimethyl-1,3-propanediol, followed by addition of 100 mg of p-toluenesulfonic acid and 20 g of molecular sieve 4A 1/16. The mixture was stirred gently at room temperature for 12 hours. From the reaction mixture thus obtained, the molecular sieve was filtered off and the solvent in the filtrate was distilled off under reduced pressure. Finally the residue was purified by silica gel chromatography (eluent: ethyl acetate-hexane =1:10, v/v) to give 3.14 g of 20-(5,5-dimethyl-1,3-dioxan-2-yl)-7α-hydroxypregna-1,4-dien-3-one (yield: 50%).

$^1$H-NMR spectrum (90 MHz) $\delta_{TMS}^{CDCl_3}$: 0.80 (s, 3 H), 0.83 (s, 3 H), 1.07 (d, J=6 Hz, 3 H), 1.17 (s, 3 H), 1.22 (s, 3 H), 3.2–3.7 (m, 5 H), 4.53 (d, J=1.5 Hz, 1 H), 6.10 (m, 1 H), 6.22 (dd, J=10, 1.5 Hz, 1 H), 7.21 (d, J=10 Hz, 1 H).

EXAMPLE 5

To a solution of 3.00 g (6.98 mmoles) of 20-(5,5-dimethyl-1,3-dioxan-2-yl)-7α-hydroxypregna-1,4-dien-3-one in 200 ml of benzene was added 50 mg of p-toluenesulfonic acid and the mixture was refluxed for 5 hours, with the byproduct water being constantly removed from the reaction system by means of a Dean-Stark trap. The reaction mixture thus obtained was cooled to room temperature and washed with aqueous sodium hydrogen carbonate solution. The aqueous layer was extracted with ether and the extract was combined with the organic layer. This mixture was washed with aqueous sodium chloride solution and dried over magnesium sulfate, and the solvent was distilled off under reduced pressure. Finally the residue was purified by silica gel chromatography (eluent: ethyl acetate-hexane =1:10, v/v) to recover 2.58 g of 20-(5,5-dimethyl-1,3-dioxan-2-yl)pregna-1,4,6-trien-3-one (yield: 90%). The $^1$H-NMR spectrum of this product was in agreement with that of the 20-(5,5-dimethyl-1,3-dioxan-2-yl)pregna-1,4,6-trien-3-one obtained in Example 3.

EXAMPLE 6

A 10 weight % solution of sodium hydroxide in methanol (1.16 ml) and 6.36 ml of a 30 weight % solution of hydrogen peroxide in water (containing 62.3 mmoles of hydrogen peroxide) were added to a solution of 4.66 g (11.3 mmoles) of 20-(5,5-dimethyl-1,3-dioxan-2-yl)pregna-1,4,6-trien-3-one in 150 ml of methanol and the mixture was stirred at room temperature for 16 hours. The reaction mixture thus obtained was diluted with water and after the methanol was partially distilled off under reduced pressure at room temperature, the residue was extracted with ether. The extract was washed successively with aqueous potassium iodide solution and aqueous sodium chloride solution and the organic layer was dried over magnesium sulfate. The solvent was then distilled off under reduced pressure and the residue was purified by silica gel chromatography (eluent: ethyl acetate/hexane=1:10, v/v) to recover 3.72 g of 20-(5,5-dimethyl-1,3-dioxan-2-yl)-1α,2α-epoxypregna-4,6-dien-3-one (yield: 77%).

$^1$H-NMR spectrum (90 MHz) $\delta_{TMS}^{CDCl_3}$: 0.71 (s, 3 H), 0.77 (s, 3 H), 1.08 (d, J=6 Hz, 3 H), 1.18 (s, 6 H), 3.2–3.7 (m, 6 H), 4.40 (d, J=1.5 Hz, 1 H), 5.65 (s, 1 H), 6.07 (s, 2 H).

IR spectrum (KBr): 2940, 2860, 1670, 1615, 1105 cm$^{-1}$.

EXAMPLE 7

A solution of 0.664 g (3.85 mmoles) of m-chloroperbenzoic acid in 50 ml of chloroform was mixed with a solution of 0.328 g (0.769 mmole) of 20-(5,5-dimethyl-1,3-dioxan-2-yl)-1α,2α-epoxypregna-4,6-dien-3-one in 10 ml of chloroform and the resulting mixture was stirred at room temperature for 3 days. The reaction mixture was filtered and the precipitate was washed with chloroform. The filtrate and the washings were combined, diluted with chloroform and washed successively with aqueous potassium iodide solution and aqueous sodium chloride solution. Finally the organic layer was dried over magnesium sulfate and the solvent was then distilled off under reduced pressure. The residue was purified by silica gel chromatography (eluent: ethyl acetate-hexane: 1:10, v/v) to recover 0.258 g of 20-(5,5-dimethyl-1,3-dioxan-2-yl)-1α,2α;6α,7α-diepoxypregn-4-en-3-one (yield: 76%).

$^1$H-NMR spectrum (90 MHz) $\delta_{TMS}^{CDCl_3}$: 0.71 (s, 3 H), 0.75 (s, 3 H), 1.07 (d, J=6 Hz, 3 H), 1.13 (s, 3 H), 1.17 (s, 3 H), 3.2–3.7 (m, 8 H), 4.40 (d, J=1.5 Hz, 1 H), 6.10 (d, J=1.5 Hz, 1 H).

IR spectrum (KBr): 2900, 1680, 1150, 1105, 870 cm$^{-1}$.

EXAMPLE 8

To a solution of 0.43 g (1.0 mmole) of 20-(5,5-dimethyl-1,3-dioxan-2-yl)-1α,2α-epoxypregna-4,6-dien-3-one in 10 ml of methylene chloride was added 3 ml of 0.5M-aqueous sodium hydrogen carbonate solution under stirring and cooling in an ice-water bath, followed by gradual addition of 0.34 g (2.0 mmoles) of m-chloroperbenzoic acid. The mixture was stirred at room temperature for 2 days. The reaction mixture thus obtained was subjected to phase separation and the aqueous layer was extracted twice with 10 ml portions of methylene chloride. The extract was combined with the organic layer obtained above and the mixture was washed successively with aqueous potassium iodide solution and aqueous sodium chloride solution, and dried over magnesium sulfate. The solvent was then distilled off under reduced pressure and the residue was purified by silica gel chromatography (eluent: ethyl acetate-hexane=1:10, v/v) to recover 0.35 g of 20-(5,5-dimethyl-1,3-dioxan-2-yl)-1α,2α;6α,7α-diepoxypregn-4-en-3-one (yield: 79%). The $^1$H-MNR and IR spectra of this product were in agreement with those of the 20-(5,5-dimethyl-1,3-dioxan-2-yl)-1α,2α;6α,7α-diepoxypregn-4-en-3-one obtained in Example 7.

EXAMPLE 9

To a solution of 0.105 g (0.237 mmole) of 20-(5,5-dimethyl-1,3-dioxan-2-yl)-1α,2α;6α,7α-diepoxypregn-4-en-3one and 6 ml of ethanol was added 9 mg (0.237 mmole) of sodium borohydride at a temperature of 0° C. and the mixture was stirred at 0° C. for 30 minutes. To the reaction mixture were added water and 1N-hydrochloric acid in the order mentioned and the mixture was extracted with methylene chloride. The aqueous layer was further extracted with methylene chloride and the extract was pooled with the previous methylene chloride extract. The mixture was washed successively with cold saturated sodium hydrogen carbonate solution and aqueous sodium chloride solution and the organic layer was dried over magnesium sulfate. The solvent was then distilled off under reduced pressure and the residue was purified by silica gel chromatography (eluent: ethyl acetate-hexane=1:10, v/v) to recover 0.084 g of 20-(5,5-dimethyl-1,3-dioxan-2-yl)-1α,2α;6α,7α-diepoxypregn-4-en-3β-ol (yield: 80%).

$^1$H-NMR spectrum (90 MHz) $\delta_{TMS}^{CDCl_3}$: 0.70 (s, 3 H), 0.73 (s, 3 H), 0.95 (s, 3 H), 1.06 (d, J=6 Hz, 3 H), 1.17 (s, 3 H), 3.2–3.7 (m, 8 H), 4.40 (d, J=1.5 Hz, 1 H), 4.3–4.5 (br, 1 H), 5.70 (dd, J=2.2, 1.9 Hz, 1 H).

IR spectrum (CHCl$_3$): 3400, 2940, 1105 cm$^{-1}$.

EXAMPLE 10

To a mixture of 0.084 g (0.189 mmole) of 20-(5,5-dimethyl-1,3-dioxan-2-yl)-1α,2α;6α,7α-diepoxypregn-4-en-3β-ol, 0.5 ml (6.18 mmoles) of dry pyridine and 5 ml of methylene chloride was gradually added 0.1 ml (1.06 mmoles) of acetic anhydride dropwise at a temperature of 0° C. and the solution was stirred at room temperature for 8 hours. The reaction mixture thus obtained was diluted with methylene chloride and washed with saturated aqueous copper (II) sulfate solution. The aqueous layer (washings) was extracted with methylene chloride and the extract was combined with the organic layer. The resulting mixture was washed with water and aqueous sodium chloride solution in that order and dired over magnesium sulfate. The solvent was then distilled off under reduced pressure and the residue was purified by silica gel chromatography (eluent: ethyl acetate-hexane: 1:10, v/v) to recover 0.083 g of 20-(5,5-dimethyl-1,3-dioxan-2-yl)-1α,2α;6α,7α-diepoxypregn-4-en-3β-yl acetate (yield: 90%).

$^1$H-NMR spectrum (90 MHz) $\delta_{TMS}^{CDCl_3}$: 0.70 (s, 3 H), 0.73 (s, 3 H), 0.98 (s, 3 H), 1.06 (d, J=6 Hz, 3 H), 1.17 (s, 3 H), 2.15 (s, 3 H), 3.1–3.7 (m, 8 H), 4.40 (d, J=1.5 Hz, 1 H), 5.5–5.7 (m, 2 H).

EXAMPLE 11

A mixture of 11.6 mg (0.0112 mmole) of tris(dibenzylideneacetone)dipalladium(chloroform), 22.4 μl (0.0898 mmole) of tributylphosphine and 2 ml of dry tetrahydrofuran was stirred in an atmosphere of argon gas at room temperature for 10 minutes. To this mixture was added 14.2 mg (0.224 mmole) of ammonium formate, followed by stirring for 30 minutes. To the resulting mixture was further added a solution of 27.3 mg (0.0561 mmole) of 20-(5,5-dimethyl-1,3-dioxan-2-yl)-1α,2α;6α,7α-diepoxypregn-4-en-3β-yl acetate in 2 ml of dry tetrahydrofuran and the mixture was refluxed for 10 minutes. The reaction mixture was cooled to room temperature, diluted with methylene chloride and washed with cold 1N-hydrochloric acid. The aqueous layer (washings) was extracted with methylene chloride and the extract was combined with the organic layer. The resulting mixture was washed successively with cold saturated aqueous sodium hydrogen carbonate solution and aqueous sodium chloride solution and dried over magnesium sulfate. The solvent was then distilled off under reduced pressure Purification of the residue by silica gel chromatography (eluent: ethyl acetate-hexane=1:5, v/v) gave 11.0 mg of 20-(5,5-dimethyl-methyl-1,3-dioxan-2-yl)-1α,2α-epoxy-7α-hydroxypregn-5-en-3β-yl acetate (yield: 40%). In addition, 11.8 mg of 20-(5,5-dimethyl-1,3-dioxan-2-yl)-1α,2α-epoxy-7α-hydroxypregn-4-en-3β-yl acetate was recovered as a byproduct (yield: 43%).

Analytical data on
20-(5,5-dimethyl-1,3-dioxan-2-yl)-1α,2α-epoxy-7α-hydroxypregn-5-en-3β-yl acetate $^1$H-NMR spectrum (90 MHz) $\delta_{TMS}^{CDCl_3}$: 0.70 (s, 6 H), 1.04 (s, 3 H), 1.17 (s, 3 H), 1.18 (d, J=6 Hz, 3 H), 2.09 (s, 3 H), 3.1–3.7 (m, 6 H), 3.7–3.9 (m, 1 H), 4.37 (br. s, 1 H), 5.1–5.3 (m, 1 H), 5.71 (d, J=5.5 Hz, 1 H).

Analytical data on
20-(5,5-dimethyl-1,3-dioxan-2-yl)-1α,2α-epoxy-7α-hydroxypregn-4-en-3β-yl acetate $^1$H-NMR spectrum (90 MHz) $\delta_{TMS}^{CDCl_3}$: 0.70 (s, 6 H), 1.06 (d, J=5.5 Hz, 3 H), 1.09 (s, 3 H), 1.17 (s, 3 H), 2.14 (s, 3 H), 3.2–3.8 (m, 7 H), 4.37 (br. s, 1 H), 5.14 (d, J=2 Hz, 1 H), 5.57 (dd, J=3, 5.5 Hz, 1 H).

IR spectrum (CHCl$_3$): 2940, 1730, 1240, 1105 cm$^{-1}$.

EXAMPLE 12

To a mixture of 49.0 mg (0.1 mmole) of 20-(5,5-dimethyl-1,3-dioxan-2-yl)-1α,2α-epoxy-7αhydroxy-pregn-5-en-3β-yl acetate, 0.24 ml (3 mmoles) of pyridine and 10 ml of dry methylene chloride was added 0.1 ml (1.3 mmoles) of methyl chlorocarbonate dropwise at a temperature of 0° C. and the mixture was stirred at room temperature for 8 hours. The reaction mixture was washed with cold 1N-hydrochloric acid and the aqueous layer (washings) was extracted with methylene chloride. The extract was combined with the organic layer and the resulting mixture was washed successively with water, aqueous sodium hydrogen carbonate solution and aqueous sodium chloride solution and dried over magnesium sulfate. The solvent was then distilled off under reduced pressure and the residue was purified by silica gel chromatography (eluent: ethyl acetate-hexane=1:10, v/v) to recover 43.7 mg of 20-(5,5-dimethyl-1,3-dioxan-2-yl)-1α,2α-epoxy-7α-methoxycarbonyloxy-pregn-5-en-3β-yl acetate (yield: 80%).

$^1$H-NMR spectrum (90 MHz) $\delta_{TMS}^{CDCl_3}$: 0.70 (s, 6 H), 1.04 (s, 3 H), 1.17 (s, 3 H), 1.18 (d, J=6 Hz, 3 H), 2.09 (s, 3 H), 3.1– 3.7 (m, 6 H), 3.75 (s, 3 H), 4.37 (br. s, 1 H), 4.7–4.9 (m, 1 H), 5.1–5.3 (m, 1 H), 5.71 (d, J=5.5 Hz, 1 H).

EXAMPLE 13

To a mixture of 49.0 mg (0.1 mmole) of 20-(5,5-dimethyl-1,3-dioxan-2-yl)-1α,2α-epoxy-7α-hydroxy-pregn-5-en-3β-yl acetate, 0.24 m; (3 mmoles) of pyridine, 0.5 mg (0.004 mmole) of 4-(dimethylamino)pyridine and 10 ml of dry methylene chloride was added 0.12 ml (1.3 mmoles) of acetic anhydride dropwise at a temperature of 0° C. and the solution was stirred at room temperature for 10 hours. The reaction mixture was diluted with 20 ml of methylene chloride and washed with cold 1N-hydrochloric acid. The aqueous layer (washings) was extracted with methylene chloride and the extract was combined with the organic layer. The resulting mixture was washed successively with water, aqueous sodium hydrogen carbonate solution and aqueous sodium chloride solution and dried over magnesium sulfate. The solvent was distilled off under reduced pressure and the residue was purified by silica gel chromatography (eluent: ethyl acetate-hexane=1:10, v/v) to recover 45 mg of 7α-acetoxy-20-(5,5-dimethyl-1,3-dioxan-2-yl)-1α,2α-epoxypregn-5-en-3β-yl acetate (yield: 85%).

$^1$H-NMR spectrum (90 MHz) $\delta_{TMS}^{CDCl_3}$: 0.70 (s, 6 H), 1.04 (s, 3 H), 1.17 (s, 3 H), 1.18 (d, J=6 Hz, 3 H), 2.05 (s, 3 H), 2.09 (s, 3 H), 3.1–3.7 (m, 6 H), 4.36 (br. s, 1 H), 4.8–5.0 (m, 1 H), 5.1–5.3 (m, 1 H), 5.64 (d, J=5.5 Hz, 1 H).

EXAMPLE 14

A mixture of 49.0 mg (0.1 mmole) of 20-(5,5-dimethyl-1,3-dioxan-2-yl)-1α,2α-epoxy-7α-hydroxypregn-5-en-3β-yl acetate, 0.24 ml (3 mmoles) of pyridine, 0.5 mg (0.004 mmole) of 4-(dimethylamino)pyridine, 0.12 ml (1.3 mmoles) of N,N-dimethylcarbamoyl chloride and 10 ml of dry toluene was stirred at a temperature of 60° C. for 10 hours. The reaction mixture thus obtained was cooled to room temperature, diluted with 50 ml of methylene chloride, washed with water 3 times and finally washed with aqueous sodium chloride solution. The organic layer was dried over magnesium sulfate and the solvent was distilled off under reduced pressure. Finally the residue was purified by silica gel chromatography (eluent: ethyl acetate-hexane=1:10, v/v) to recover 37 mg of 7α-(N,N-dimethylcarbamoyloxy)-20-(5,5-dimethyl-1,3-dioxan-2-yl)-1α,2α-epoxypregn-5-en-3β-yl acetate (yield: 70%).

$^1$H-NMR spectrum (90 MHz) $\delta_{TMS}^{CDCl_3}$: 0.70 (s, 6 H), 1.05 (s, 3 H), 1.17 (s, 3 H), 1.18 (d, J=6 Hz, 3 H), 2.09 (s, 3 H), 2.79 (s, 3 H), 2.82 (s, 3 H), 3.2–3.8 (m, 6 H), 4.38 (br. s, 1 H), 4.7–4.9 (m, 1 H), 5.1–5.3 (m, 1 H), 5.72 (d, J=5 Hz, 1 H).

EXAMPLE 15

In 5 ml of toluene was dissolved 49.0 mg (0.1 mmole) of 20-(5,5-dimethyl-1,3-dioxan-2-yl)-1α,2α-epoxy-7α-hydroxypregn-5-en-3β-yl acetate, followed by addition of one drop of pyridine. Then, 0.1 ml (1.7 mmoles) of methyl isocyanate was added at a temperature of 0° C. and the mixture was stirred at a temperature of 60° C. for 30 minutes. The reaction mixture thus obtained was cooled to room temperature, poured in ice-water, and extracted 3 times with 20 ml portions of methylene chloride. The extracts are pooled, washed successively with water and aqueous sodium chloride solution, and dried over magnesium sulfate. The solvent was then distilled off under reduced pressure. Finally the residue was purified by silica gel chromatography (eluent: ethyl acetate-hexane=1:10, v/v) to recover 35 mg of 20-(5,5-dimethyl-1,3-dioxan-2-yl)-1α,2α-epoxy-7α-(N-methyl-carbamoyloxy)pregn-5-en-3β-yl acetate (yield: 65%).

$^1$H-NMR spectrum (90 MHz) $\delta_{TMS}^{CDCl_3}$: 0.70 (s, 6 H), 1.05 (s, 3 H), 1.17 (s, 3 H), 1.20 (d, J=6 Hz, 3 H), 2.09 (s, 3 H), 2.8 (d, J=6 Hz, 3 H), 3.2–3.8 (m, 6 H), 4.40 (br. s, 1 H), 4.7–4.9 (m, 1 H), 5.1–5.3 (m, 2 H), 5.70 (d, J=5 Hz, 1 H).

EXAMPLE 16

The procedure of Example 15 was repeated except that 0.14 ml (1.3 mmoles) of phenyl isocyanate was used in lieu of 0.1 ml of methyl isocyanate to give 43 mg of 20-(5,5-dimethyl-1,3-dioxan-2-yl)-1α,2α-epoxy-7α-(N-phenylcarbamoyloxy)pregn-5-en-3β-yl acetate (yield:

$^1$H-NMR spectrum (90 MHz $\delta_{TMS}^{CDCl_3}$: 0.71 (s, 6 H), 1.06 (s, 3 H), 1.18 (s, 3 H), 1.20 (d, J=6 Hz, 3 H), 2.10 (s, 3 H), 3.2–3.8 (m, 6 H), 4.39 (br. s, 1 H), 4.7–4.9 (m, 1 H), 5.1–5.3 (m, 1 H), 5.70 (d, J=5 Hz, 1 H), 6.92 (br. s, 1 H), 7.1–7.7 (m, 5 H).

EXAMPLE 17

A mixture of 10.3 mg (0.00997 mmole) of tris(dibenzylideneacetone)dipalladium(chloroform), 19.9 μl (0.0798 mmole) of tributylphosphine and 5 ml of dry 1,4-dioxane was stirred in an atmosphere of argon gas at room temperature for 10 minutes. To this mixture was added a solution of 43.6 mg (0.0798 mmole) of 20-(5,5-dimethyl-1,3-dioxan-2-yl)-1α,2α-epoxy-7α-methoxycarbonyloxypregn-5-en-3μ-yl acetate in 2 ml of dry 1,4-dioxane, and the mixture was refluxed for 8 hours. The reaction mixture was cooled to room temperature and filtered through a glass filter with the aid of Florisil. The filtrate was concentrated under reduced pressure and the concentrate was purified by silica gel chromatography (eluent: ether-hexane=1:10, v/v) to give 17.4 mg of 20-(5,5-dimethyl-1,3-dioxan-2-yl)-1α,2α-epoxypregna-5,7-dien-3β-yl acetate. In addition, 15.3 mg of the starting compound 20-(5,5-dimethyl-1,3-dioxan-2-yl)-1α,2α-epoxy-7α-methoxycarbonyloxypregn-5-en-3β-yl acetate was recovered. The yield of 20-(5,5-dimethyl-1,3-dioxan-2-yl)-1α,2α-epoxypregna-5,7-dien-3β-yl acetate was 71% based on consumed 20-(5,5-dimethyl-1,3-dioxan-2-yl)-1α,2α-epoxy-7α-methoxycarbonyloxypregn-5-en-3β-yl acetate.

$^1$H-NMR spectrum (90 MHz) $\delta_{TMS}^{CDCl_3}$: 0.62 (s, 3 H), 0.71 (s, 3 H), 1.00 (s, 3 H), 1.10 (d, J=6 Hz, 3 H), 1.17 (s, 3 H), 2.10 (s, 3 H), 2.3–2.6 (m, 2 H), 3.16 (d, J=4 Hz, 1 H), 3.2–3.7 (m, 5 H), 4.40 (br. s, 1 H), 5.0–5.7 (m, 3 H).

EXAMPLE 18

The procedure of Example 17 was repeated except that 42.3 mg (0.0798 mmole) of 7α-acetoxy-20-(5,5-dimethyl-1,3-dioxan-2-yl)-1α,2α-epoxypregn-5-en-3β-yl acetate was used in lieu of 43.6 mg of 20-(5,5-dimethyl-1,3-dioxan-2-yl)-1α,2α-epoxy-7α-methoxycarbonyloxypregn-5-en-3β-yl acetate to give 17.6 mg of 20-(5,5-dimethyl-1,3-dioxan-2-yl)-1α,2α-epoxypregna-5,7-dien-3β-yl acetate. In addition, 14.0 mg of 7α-acetoxy-20-(5,5-dimethyl-1,3-dioxan-2-yl)-1α,2α-epoxypregn-5-en-38-yl acetate was recovered. The yield of 20-(5,5-dimethyl-1,3-dioxan-2-yl)-1α,2α-epoxypregna-5,7-dien-3β-yl acetate was 70% based on consumed 7α-acetoxy-20-(5,5-dimethyl-1,3-dioxan-2-yl)-1α,2α-epoxypregn-5-en-3β-yl acetate. The $^1$H-NMR spectrum of the product 20-(5,5-dimethyl-1,3-dioxan-2-yl)-1α,2α-epoxypregna-5,7-dien-3β-yl acetate was in agreement with that of the 20-(5,5-dimethyl-1,3-dioxan-2-yl)-1α,2α-epoxypregna-5,7-dien-3β-yl acetate obtained in Example 17.

EXAMPLE 19

The procedure of Example 17 was repeated except that 44.6 mg (0.0798 mmole) of 7α-(N,N-dimethylcarbamoyloxy)-20-(5,5-dimethyl-1,3-dioxan-2-yl)-1α,2α-epoxypregn-5-en-3β-yl acetate was used in lieu of 43.6 mg of 20-(5,5-dimethyl-1,3-dioxan-2-yl)-1α,2α-epoxy-7α-methoxycarbonyloxypregn-5-en-3β-yl acetate to give 16.6 mg of 20-(5,5-dimethyl-1,3-dioxan-2-yl)-1α,2α-epoxypregna-5,7-dien-3β-yl acetate. In addition, 16.0 mg of 7α-(N,N-dimethylcarbamolyoxy)-20-(5,5-dimethyl-1,3-dioxan-2-yl)-1α,2α-epoxypregn-5-en-3β-yl acetate was recovered. The yield of 20-(5,5-dimethyl-1,3-dioxan-2-yl)-1α,2α-epoxypregna-5,7-dien-3β-yl acetate was 69% based on consumed 7α-(N,N-dimethylcarbamoyloxy)-20-(5,5-dimethyl-1,3-dioxan-2-yl)-1α,2α-epoxypregn-5-en-3β-yl acetate. The $^1$H-NMR spectrum of the product 20-(5,5-dimethyl-1,3-dioxan-2-yl)-1α,2α-epoxypregna-5,7-dien-3β-yl acetate was in agreement with that of the 20-(5,5-dimethyl-1,3-dioxan-2-yl)-1α,2α-epoxypregna-5,7-dien-3β-yl acetate obtained in Example 17.

EXAMPLE 20

The procedure of Example 17 was repeated except that 43.5 mg (0.0798 mmole) of 20-(5,5-dimethyl-1,3-dioxan-2-yl)-1α,2α-epoxy-7α-(N-methylcarbamoyloxy)-pregn-5-en-3β-yl acetate was used in lieu of 43.6 mg of 20-(5,5-dimethyl-1,3-dioxan-2-yl)-1α,2α-epoxy-7α-methoxy-carbonyloxypregn-5-en-3β-yl acetate to give 16.6 mg of 20-(5,5-dimethyl-1,3-dioxan-2-yl)-1α,2α-epoxypregna-5,7-dien-3β-yl acetate. In addition, 15.2 mg of 20-(5,5-dimethyl-1,3-dioxan-2-yl)-1α,2α-epoxy-7α-(N-methylcarbamoyloxy)pregn-5-en-3β-yl acetate was recovered. The yield of 20-(5,5-dimethyl-1,3-dioxan-2-yl)-1α,2α-epoxy-pregna-5,7-dien-3β-yl acetate was 68% based on consumed 20-(5,5-dimethyl-1,3-dioxan-2-yl)-1α,2α-epoxy-7α-(N-methylcarbamoyloxy)pregn-5-en-3β-yl acetate. The $^1$H-NMR spectrum of the product 20-(5,5-dimethyl-1,3-dioxan-2-yl)-1α,2α-epoxypregna-5,7-dien-3β-yl acetate was in agreement with that of the 20-(5,5-dimethyl-1,3-dioxanyl)-1α,2α-epoxypregna-5,7-dien-3β-yl acetate obtained in Example 17.

EXAMPLE 21

The procedure of Example 17 was repeated except that 48.4 mg (0.0798 mmole) of 20-(5,5-dimethyl-1,3-dioxan-2-yl)-1α,2α-epoxy-7α-(N-phenylcarbamoyloxy)pregn-5-en-3β-yl acetate was used in lieu of 43.6 mg of 20-(5,5-dimethyl-1,3-dioxan-2-yl)-1α,2α-epoxy-7α-methoxycarbonyloxypregn-5-en-3β-yl acetate to give 16.3 mg of 20-(5,5-dimethyl-1,3-dioxan-2-yl)-1α,2α-epoxypregna-5, 7-dien-3β-yl acetate. In addition, 17.4 mg of 20-(5,5-dimethyl-1,3-dioxan-2-yl)-1α,2α-epoxy-7α-(N-phenylcarbamoyloxy)pregn-5-en-3β-yl acetate was recovered. The yield of 20-(5,5-dimethyl-1,3-dioxan-2-yl)-1α,2α-epoxypregna-5,7-dien-3β-yl acetate was 68% based on consumed 20-(5,5-dimethyl-1,3-dioxan-2-yl)-1α,2α-epoxy-7α-(N-phenylcarbamoyloxy)pregn-5-en-3β-yl acetate. The $^1$H-NMR spectrum of the product 20-(5,5-dimethyl-1,3-dioxan-2-yl)-1α,2α-epoxypregna-5,7-dien-3β-yl acetate was in agreement with that of the 20-(5,5-dimethyl-1,3-dioxan-2-yl)-1α,2α-epoxypregna-5,7-dien-3β-yl acetate obtained in Example 17.

EXAMPLE 22

To a mixture of 49.0 mg (0.1 mmole) of 20-(5,5-dimethyl-1,3-dioxan-2-yl)-1α,2α-epoxy-7α-hydroxypregn-5-en-3β-yl acetate, 0.24 ml (3 mmoles) of pyridine, 0.5 mg (0.004 mmole) of 4-(dimethylamino)pyridine and 10 ml of methylene chloride was added 0.10 ml (1.3 mmoles) of methanesulfonyl chloride dropwise at a temperature of 0° C. and the mixture was stirred at room temperature for 12 hours. The reaction mixture was diluted with 20 ml of methylene chloride, then washed successively with cold 1N-hydrochloric acid, water, aqueous sodium hydrogen carbonate solution and aqueous sodium chloride solution, and dried over magnesium sulfate. The solvent was then distilled off under reduced pressure. Finally the residue was purified by silica gel chromatography (eluent: ethyl acetate-hexane=1:10, v/v) to give 25.5 mg of 20-(5,5-dimethyl-1,3-dioxan-2-yl)-1α,2α-epoxypregna-5,7-dien-3β-yl acetate (yield: 54%). The $^1$H-NMR spectrum of this product was in agreement with that of the 20-(5,5-dimethyl-1,3-dioxan-2-yl)-1α,2α-epoxypregna-5,7-dien-3β-yl acetate obtained in Example 17.

EXAMPLE 23

To a solution of 5 mg (0.0106 mmole) of 20-(5,5-dimethyl-1,3-dioxan-2-yl)-1α,2α-epoxypregna-5,7-dien-3β-yl acetate in 2 ml of dry methanol was added 7.3 mg (0.0528 mmole) of anhydrous potassium carbonate and the mixture was stirred at room temperature for 2 hours. The reaction mixture was filtered through a glass filter with the aid of Celite and the filtrate was concentrated under reduced pressure. Finally the concentrate was purified by silica gel chromatography (eluent: ethyl acetate-hexane = 1:5, v/v) to give 4 mg of 20-(5,5-dimethyl-1,3-dioxan-2-yl)-1α,2α-epoxypregna-5,7-dien-3β-ol (yield: ca. 90%).

$^1$H-NMR spectrum (90 MHz) $\delta_{TMS}^{CDCl_3}$: 0.64 (s, 3 H), 0.71 (s, 3 H), 1.01 (s, 3 H), 1.10 (d, J=6 Hz, 3 H), 1.18 (s, 3 H), 3.16 (d, J=4 Hz, 1 H), 3.2–3.7(m, 5 H), 4.0–4.3 (m, 1 H), 4.41 (br. s, 1 H), 5.3–5.5 (m, 1 H), 5.6–5.8 (m, 1 H).

UV spectrum (ethanol) $\lambda_{max}$: 278 nm (ε:5847)

EXAMPLE 24

To a suspension of 4 mg (0.1 mmole) of lithium aluminum hydride in 4 ml of dry tetrahydrofuran was added a solution of 3.8 mg (0.00887 mmole) of 20-(5,5-dimethyl-1,3-dioxan-2-yl)-1α,2α-epoxypregna-5,7-dien-3β-ol in 2 ml of dry tetrahydrofuran at a temperature of 60° C. and the mixture was stirred at 60° C. for 30 minutes. To the reaction mixture was added water to decompose the excess lithium aluminum hydride and the tetrahydrofuran was distilled off under reduced pressure at a temperature not exceeding 60° C. To the residue was added cold 1N-hydrochloric acid and the mixture was extracted with chloroform. The extract was washed with aqueous sodium chloride solution and dried over magnesium sulfate. The solvent was then distilled off under reduced pressure and the residue was purified by silica gel chromatography (eluent: ethyl acetate-hexane = 1:5, v/v) to give 3 mg of 20-(5,5-dimethyl-1,3-dioxan-2-yl)pregna-5,7-diene-1α,3β-diol (yield: ca. 80%).

$^1$H-NMR spectrum (90 MHz $\delta_{TMS}^{CDCl_3}$: 0.63 (s, 3 H), 0.71 (s, 3 H), 0.91 (s, 3 H), 1 10 (d, J=6 Hz, 3 H), 1.18 (s, 3 H), 3.2–3.7 (m, 5 H), 4.0–4.3 (m, 1 H), 4.41 (br. s, 1 H), 5.3–5.5 (m, 1 H), 5.6–5.8 (m, 1 H).

UV spectrum (ethanol) $\lambda_{max}$: 271, 282 (ε:5847), 293 nm.

EXAMPLE 25

In 10 ml of acetone was dissolved 4.3 mg (0.010 mmole) of 20-(5,5-dimethyl-1,3-dioxan-2-yl)pregna-5,7-diene-1α,3β-diol, followed by addition of 1 ml of a 1 mmole/l solution of p-toluenesulfonic acid in acetone (containing 0.001 mmole of p-toluenesulfonic acid). The mixture was refluxed for 2 hours. The reaction mixture thus obtained was cooled to room temperature and the solvent was distilled off under reduced pressure. The residue was dissolved in 40 ml of methylene chloride and this methylene chloride solution was washed with saturated aqueous sodium hydrogen carbonate solution and saturated aqueous sodium chloride solution in that order and dried over magnesium sulfate. The solvent was distilled off under reduced pressure and the residue was purified by silica gel chromatography (eluent: ethyl acetate-hexane = 1:5, v/v) to give 2.8 mg of 1α,3β-dihydroxypregna-5,7-diene-20-carbaldehyde (yield: 82%).

$^1$H-NMR spectrum (90 MHz) $\delta_{TMS}^{CDCl_3}$: 0.71 (s, 3 H), 0.92 (s, 3 H), 1.06 (d, J=6 Hz, 3 H), 3.2–3.8 (m, 1 H), 4.0–4.3 (m, 1 H), 5.3–5.5 (m, 1 H), 5.6–5.8 (m, 1 H), 9.54 (d, 1 H).

EXAMPLE 26

In 100 ml of acetone was dissolved 0.410 g (1.0 mmole) of 20-(5,5-dimethyl-1,3-dioxan-2-yl)pregna-1,4,6-trien-3-one, followed by addition of 10 mg (0.05 mmole) of p-toluenesulfonic acid. The mixture was stirred at room temperature for 12 hours. From the reaction mixture thus obtained, the solvent was distilled off under reduced pressure and the residue was diluted with methylene chloride. The methylene chloride solution was washed successively with saturated aqueous sodium hydrogen carbonate solution and saturated aqueous sodium chloride solution and dried over magnesium sulfate. The solvent was then distilled off under reduced pressure and the residue was purified by silica gel chromatography (eluent: ethyl acetate-hexane = 1:5, v/v) to recover 0.243 g of 3-oxopregna-1,4,6-triene-20-carbaldehyde (yield: 75%).

$^1$H-NMR spectrum (90 MHz) $\delta_{TMS}^{CDCl_3}$: 0.76 (s, 3 H), 1.08 (d, J=6 Hz, 3 H), 1.20 (s, 3 H), 5.9–6.2 (m, 3 H), 6.19 (dd, J=10, 1.5 Hz, 1 H), 7.02 (d, J=10 Hz, 1 H), 9.57 (d, J=3 Hz, 1 H).

EXAMPLE 27

The procedure of Example 26 was repeated except that 0.426 g (1.0 mmole) of 20-(5,5-dimethyl-1,3-dioxan-2-yl)-1α,2α-epoxypregna-4,6-dien-3-one was used in lieu of 0.410 g of 20-(5,5-dimethyl-1,3-dioxan-2-yl)pregna-1,4,6-trien-3-one to give 0.205 g of 1α, 2α-epoxy-3-oxopregna-4,6-diene-20-carbaldehyde (yield: 60%).

$^1$H-NMR spectrum (90 MHz) $\delta_{TMS}^{CDCl_3}$: 0.77 (s, 3 H), 1.09 (d, J=6 Hz, 3 H), 1.20 (s, 3 H), 3.2–3.7 (m, 2 H), 5.67 (s, 1 H), 6.09 (s, 2 H), 9.55 (d, J=3 Hz, 1 H).

EXAMPLE 28

In 10 ml of acetone was dissolved 44.2 mg (0.1 mmole) of 20-(5,5-dimethyl-1,3-dioxan-2-yl)-1α,2α;6α,7α-diepoxypregn-4-en-3-one, followed by addition of 5 mg (0.02 mmole) of pyridinium p-toluenesulfonate. The mixture was refluxed for 2 hours. The reaction mixture thus obtained was cooled to room temperature and the solvent was distilled off under reduced pressure. The residue was diluted with methylene chloride and this methylene chloride solution was washed successively with saturated aqueous sodium hydrogen carbonate solution and saturated aqueous sodium chloride solution and dried over magnesium sulfate. The solvent was then distilled off under reduced pressure and the residue was purified by silica gel chromatography (eluent: ethyl acetate-hexane = 1:5, v/v) to recover 19.6 mg of 1α,2α;6α,7α-diepoxy-3-oxopregn-4-ene-20-carbaldehyde (yield: 55%).

$^1$H-NMR spectrum (90 MHz) $\delta_{TMS}^{CDCl_3}$: 0.76 (s, 3 H), 1.08 (d, J=6 Hz, 3 H), 1.15 (s, 3 H), 3.2–3.7 (m, 4 H), 6.11 (d, J=1.5 Hz, 1 H), 9.54 (d, J=3 Hz, 1 H).

EXAMPLE 29

The procedure of Example 28 was repeated except that 44.4 mg (0.1 mmole) of 20-(5,5-dimethyl-1,3-dioxan-2-yl)-1α,2α;6α,760 -diepoxypregn-4-en-3β-ol was used in lieu of 44.2 mg of 20-(5,5-dimethyl-1,3-dioxan-2-yl)-1α,2α;6α,7α-diepoxygregn-4-en-3-one to give 19.0 mg of 1α,2α;6α,7α-diepoxy-3β-hydroxypregn-4-ene-20-carbaldehyde (yield: 53%).

¹H-NMR spectrum (90 MHz) $\delta_{TMS}^{CDCl_3}$: 0.73 (s, 3 H), 0.96 (s, 3 H), 1.06 (d, J=6 Hz, 3 H), 3.2-3.7 (m, 4 H), 4.3-4.5 (br, 1 H), 5.71 (m, 1 H), 9.52 (d, J=3 Hz, 1 H).

EXAMPLE 30

In 5 ml of acetone was dissolved 24.3 mg (0.05 mmole) of 20-(5,5-dimethyl-1,3-dioxan-2-yl)-1α,2α;6α,-7α- diepoxypregn-4-en-3β-yl acetate, followed by addition of 2.5 mg (0.01 mmole) of pyridinium p-toluenesulfonate. The mixture was refluxed for 2 hours. The reaction mixture thus obtained was cooled to room temperature and the solvent was distilled off under reduced pressure. To the residue was added methylene chloride and the mixture was washed successively with saturated aqueous sodium hydrogen carbonate solution and saturated aqueous sodium chloride solution and dried over magnesium sulfate. The solvent was then distilled off under reduced pressure and the residue was purified by silica gel chromatography (eluent: ethyl acetate-hexane=1:5, v/v) to recover 9.6 mg of 3β-acetoxy-1α,2α;-6α,7α-diepoxypregn-4-ene-20-carbaldehyde (yield: 48%).

¹H-NMR spectrum (90 MHz) $\delta_{TMS}^{CDCl_3}$: 0.74 (s, 3 H), 0.99 (s, 3 H), 1.07 (d, J=6 Hz, 3 H), 2.15 (s, 3 H), 3.1-3.7 (m, 4 H), 5.5-5.7 (m, 2 H), 9.54 (d, J=3 Hz, 1 H).

EXAMPLE 31

The procedure of Example 23 was repeated except that 4.9 mg (0.01 mmole) of 20-(5,5-dimethyl-1,3-dioxan-2-yl)-1α,2α-epoxy-7α-hydroxypregn-5-en-3β-yl acetate was used in lieu of 5 mg of 20-(5,5-dimethyl-1,3-dioxan-2-yl)-1α,2α-epoxypregna-5,7-dien-3β-yl acetate to give 3.7 mg of 20-(5,5-dimethyl-1,3-dioxan-2-yl)-1α,2α-epoxypregn-5-ene-3β,7α-diol (yield: 83%).

¹H-NMR spectrum (90 MHz $\delta_{TMS}^{CDCl_3}$: 0.70 (s, 6 H), 1.04 (s, 3 H), 1.18 (s, 3 H), 1.19 (d, J=6 Hz, 3 H), 3.1-3.7 (m, 6 H), 3.7-3.9 (m, 1 H), 4.1-4.3 (m, 1 H), 4.38 (br. s, 1 H), 5.70 (d, J=5 Hz, 1 H).

EXAMPLE 32

The procedure of Example 23 was repeated except that 5.5 mg (0.01 mmole) of 20-(5,5-dimethyl-1,3-dioxan-2-yl)-1α,2α--epoxy-7α-methoxycarbonyloxypregn-5-en-3β-yl acetate was used in lieu of 5 mg of 20-(5,5-dimethyl-1,3-dioxan-2-yl)-1α,2α-epoxypregna-5,7-dien-3β-yl acetate to give 2.9 mg of 20-(5,5-dimethyl-1,3-dioxan-2-yl)-1α,2α--epoxy-7α-methoxycarbonyloxypregn-5-en-3β-ol (yield: 58%).

¹H-NMR spectrum (90 MHz) $\delta_{TMS}^{CDCl_3}$: 0.70 (s, 6 H), 1.04 (s, 3 H), 1.17 (s, 3 H), 1.18 (d, J=6 Hz, 3 H), 3.1-3.7 (m, 6 H), 3.76(s, 3 H), 4.1-4.3 (m, 1 H), 4.38 (br. s, 1 H), 4.7-4.9 (m, 1 H), 5.70 (d, J=5 Hz, 1 H).

EXAMPLE 33

The procedure of Example 23 was repeated except that 5.6 mg (0.01 mmole) of 20-(5,5-dimethyl-1,3-dioxan-2-yl)-7α-(N,N-dimethylcarbamolyoxy)-1α,2α-epoxypregn-5-en-3β-yl acetate was used in lieu of 5 mg of 20-(5,5-dimethyl-1,3-dioxan-2-yl)-1α,2α-epoxypregna-5,7-dien-3β-yl acetate to give 3.7 mg of 20-(5,5-dimethyl-1,3-dioxan-2--(N,N-dimethylcarbamoyloxy)-1α,2α-epoxypregn-5-en-3β-ol (yield: 72%).

¹H-NMR spectrum (90 MHz) $\delta_{TMS}^{CDCl_3}$: 0.70 (s, 6 H), 1.05 (s, 3 H), 1.18 (s, 3 H), 1.18 (d, J=6 Hz, 3 H), 2.79 (s, 3 H), 2.83 (s, 3 H), 3.2-3.8 (6 H), 4.1-4.3 (m, 1 H), 4.40 (br. s, 1 H), 4.7-4.9 (m, 1 H), 5.1-5.3 (m, 1 H), 5.5-5.8 ( 1 H).

EXAMPLE 34

The procedure of Example 23 was repeated except that 6.1 mg (0.01 mmole) of 20-(5,5-dimethyl-1,3-dioxan-2-yl)-1α,2α-epoxy-7α-(N-phenylcarbamolyoxy)-pregn-5-en-3β-yl acetate was used in lieu of 5 mg of 20-(5,5-dimethyl-1,3-dioxan-2-yl)-1α,2α-epoxypregna-5,7-dien-3μ-yl acetate to give 4.2 mg of 20-(5,5-dimethyl-1,3-dioxan-2-yl)-1α,2α-epoxy-7α-(N-phenylcarbamoyloxy)pregn-5-en-3β-ol (yield: 74%).

¹H-NMR spectrum (90 MHz) $\delta_{TMS}^{CDCl_3}$: 0.71 (s, 6 H), 1.05 (s, 3 H), 1.18 (s, 3 H), 1.19 (d, J=6 Hz, 3 H), 3.1-3.9 (m, 7 H), 4.1-4.3 (m, 1 H), 4.39 (br. s, 1 H), 5.70 (d, J=5 Hz, 1 H), 6.90 (br. s, 1 H), 7.1-7.7 (m, 5 H).

EXAMPLE 35

The procedure of Example 23 was repeated except that 5.5 mg (0.01 mmole) of 20-(5,5-dimethyl-1,3-dioxan-2-yl)-1α,2α-epoxy-7α-(N-methylcarbamoyloxy)-pregn-5-en-3β-yl acetate was used in lieu of 5 mg of 20-(5,5-dimethyl-1,3-dioxan-2-yl)-1α,2α-epoxypregna-5,7-dien-3β-yl acetate to give 3.8 mg of 20-(5,5-dimethyl-1,3-dioxan-2-yl)-1α,2α-epoxy-7α-(N-methylcarbamoyloxy)pregn-5-en3β-ol (yield: 76%).

¹H-NMR spectrum (90 MHz) $\delta_{TMS}^{CDCl_3}$: 0.70 (s, 6 H), 1.05 (s, 3 H), 1.17 (s, 3 H), 1.20 (d, J=6 Hz, 3 H), 2.80 (d, J=6 Hz, 3 H), 3.2-3.8 (m, 6 H), 4.1-4.3 (m, 1 H), 4.40 (br. s, 1 H), 4.7-4.9 (m, 1 H), 5.1-5.3 (m, 2 H), 5.70 (d, J=5 Hz, 1 H).

EXAMPLE 36

In 2.5 ml of acetone was dissolved 2.2 mg (0.005 mmole) of 20-(5,5-dimethyl-1,3-dioxan-2-yl)-1α,2α-epoxy- pregn-5-ene-3β,7α-diol, followed by addition of 0.5 ml of a 1 mmol/l solution of p-toluenesulfonic acid in acetone (containing 0.0005 mmole of p-toluenesulfonic acid). The mixture was stirred at room temperature for 12 hours. From the reaction mixture thus obtained, the solvent was distilled off under reduced pressure and methylene chloride was added to the residue. This methylene chloride solution was washed successively with saturated aqueous sodium hydrogen carbonate and saturated aqueous sodium chloride solution and dried over magnesium sulfate. The solvent was then distilled off under reduced pressure and the residue was purified by silica gel chromatography (eluent: ethyl acetate-hexane =1:5, v/v) to recover 1.2 mg of 1α,2α-epoxy-3β,7α-dihydroxypregn-5-ene-20-carbaldehyde (yield: 67%).

¹H-NMR spectrum (90 MHz) $\delta_{TMS}^{CDCl_3}$: 0.73 (s, 3 H), 1.06 (s, 3 H), 1.20 (d, J=6 Hz, 3 H), 3.1-3.7 (m, 2 H), 3.7-3.9 (m, 1 H), 4.1-4.3 (m, 1 H), 5.71 (d, J=5 Hz, 1 H), 9.55 (d, J=3 Hz, 1 H).

EXAMPLE 37

The procedure of Example 36 was repeated except that 2.5 mg (0.005 mmole) of 20-(5,5-dimethyl-1,3-dioxan-2-yl)-1α,2α-epoxy-7α-methoxycarbonyloxypregn-5-en-3β-ol was used in lieu of 2.2 mg of 20-(5,5-dimethyl-1,3-dioxan-2-yl)-1α,2α-epoxypregn-5-ene-3β,7α-diol to give 1.3 mg of 1α,2α-epoxy-3β-hydroxy-7α-methoxycarbonyloxypregn-5-ene-20-carbaldehyde (yield: 62%).

$^1$H-NMR spectrum (90 MHz) $\delta_{TMS}^{CDCl_3}$: 0.73 (s, 3 H), 1.06 (s, 3 H), 1.18 (d, J=6 Hz, 3 H), 3.1-3.7 (m, 2 H), 3.75 (s, 3 H), 4.1-4.3 (m, 1 H), 4.7-4.9 (m, 1 H), 5.71 (d, J=5 Hz, 1 H), 9.53 (d, J=3 Hz, 1 H).

EXAMPLE 38

The procedure of Example 36 was repeated except that 2.5 mg (0.005 mmole) of 20-(5,5-dimethyl-1,3-dioxan-2-yl)-7α-(N,N-dimethylcarbamoyloxy)-1α,2α-epoxypregn-5-en-3β-ol was used in lieu of 2.2 mg of 20-(5,5-dimethyl-1,3-dioxan-2-yl)-1α,2α-epoxypregn-5-ene-3β,7α-diol to give 1.5 mg of 7α-(N,N-dimethylcarbamoyloxy)-1α,2α-epoxy-3β-hydroxypregn-5-ene-20-carbaldehyde (yield: 70%).

$^1$H-NMR spectrum (90 MHz) $\delta_{TMS}^{CDCl_3}$: 0.72 (s, 3 H), 1.05 (s, 3 H), 1.16 (d, J=6 Hz, 3 H), 2.78 (s, 3 H), 2.82 (s, 3 H), 3.1-3.7 (m, 2 H), 4.1-4.3 (m, 1 H), 4.7-4.9 (m, 1 H), 5.71 (d, J=5 Hz, 1 H), 9.55 (d, J=3 Hz, 1 H).

EXAMPLE 39

The procedure of Example 36 was repeated except that 2.8 mg (0.005 mmole) of 20-(5,5-dimethyl-1,3-dioxan-2-yl)-1α,2α-epoxy-7α-(N-phenylcarbamoyloxy)-pregn-5-en-3β-ol was used in lieu of 2.2 mg of 20-(5,5-dimethyl-1,3-dioxan-2-yl)-1α,2α-epoxypregn-5-ene-3β,7α-diol to give 1.5 mg of 1α,2α-epoxy-3β-hydroxy-7α-(N-phenylcarbamoyloxy)pregn-5-ene-20-carbaldehyde (yield: 63%).

$^1$H-NMR spectrum (90 MHz) $\delta_{TMS}^{CDCl_3}$: 0.71 (s, 3 H), 1.05 (s, 3 H), 1.17 (d, J=6 Hz, 3 H), 3.1-3.8 (m, 2 H), 4.1-4.3 (m, 1 H), 4.7-4.9 (m, 1 H), 5.70 (d, J=5 Hz, 1 H), 6.92 (br. s, 1 H), 7.1-7.7 (m, 5 H), 9.54 (d, J=3 Hz, 1 H).

EXAMPLE 40

The procedure of Example 36 was repeated except that 2.5 mg (0.005 mmole) of 20-(5,5-dimethyl-1,3-dioxan-2-yl)-1α,2α-epoxy-7α-(N-methylcarbamoyloxy)-pregn-5-en-3β-ol was used in lieu of 2.2 mg of 20-(5,5-dimethyl-1,3-dioxan-2-yl)-1α,2α-epoxypregn-5-ene-3β,7α-diol to give 1.3 mg of 1α,2α-epoxy-3β-hydroxy-7α-(N-methylcarbamoyloxy)pregn-5-ene-20-carbaldehyde (yield: 62%).

$^1$H-NMR spectrum (90 MHz) $\delta_{TMS}^{CDCl_3}$: 0.70 (s, 3 H), 1.05 (s, 3 H), 1.16 (s, 3 H), 1.19 (d, J=6 Hz, 3 H), 2.82 (d, J=6 Hz, 3 H), 3.2-3.8 (m, 2 H), 4.1-4.3 (m, 1 H), 4.7-4.9 (m, 1 H), 5.1-5.3 (m, 1 H), 5.69 (d, J=5 Hz, 1 H), 9.54 (d, J=3 Hz, 1 H).

EXAMPLE 41

In 4 ml of acetone was dissolved 4.9 mg (0.01 mmole) of 20-(5,5-dimethyl-1,3-dioxan-2-yl)-1α,2α-epoxy-7α-hydroxypregn-5-en-3β-yl acetate, followed by addition of 1 ml of a 1 mmol/l solution of p-toluenesulfonic acid in acetone (containing 0.001 mmole of p-toluenesulfonic acid). The mixture was stirred at room temperature for 12 hours. From the reaction mixture thus obtained, the solvent was distilled off under reduced pressure and the residue was diluted with methylene chloride. This methylene chloride solution was washed successively with saturated aqueous sodium hydrogen carbonate solution and saturated aqueous sodium chloride solution and dried over magnesium sulfate. The solvent was then distilled off under reduced pressure and the residue was purified by silica gel chromatography (eluent: ethyl acetate-hexane =1:5, v/v) to recover 2.7 mg of 3β-acetoxy-1α,2α-epoxy-7α-hydroxypregn-5-ene-20-carbaldehyde (yield: 67%).

$^1$H-NMR spectrum (90 MHz) $\delta_{TMS}^{CDCl_3}$: 0.70 (s, 3 H), 1.04 (s, 3 H), 1.19 (d, J=6 Hz, 3 H), 2.10 (s, 3 H), 3.1-3.7 (m, 2 H), 3.7-3.9 (m, 1 H), 5.1-5.3 (m, 1 H), 5.72 (d, J=5 Hz, 1 H), 9.55 (d, J=3 Hz, 1 H).

EXAMPLE 42

The procedure of Example 41 was repeated except that 5.5 mg (0.01 mmole) of 20-(5,5-dimethyl-1,3-dioxan-2yl)-1α,2α-epoxy-7α-methoxycarbonyloxypregn-5-en-3β-yl acetate was used in lieu of 4.9 mg of 20-(5,5-dimethyl-1,3-dioxan-2-yl)-1α,2α-epoxy-7α-hydroxypregn-5-en-3β-yl acetate to give 3.4 mg of 3β-acetoxy-1α,2α-epoxy-7α-methoxycarbonyloxypregn-5-ene-20-carbaldehyde (yield: 74%).

$^1$H-NMR spectrum (90 MHz) $\delta_{TMS}^{CDCl_3}$: 0.73 (s, 3 H), 1.06 (s, 3 H), 1.19 (d, J=6 Hz, 3 H), 2.10 (s, 3 H), 3.1-3.7 (m, 2 H), 3.76 (s, 3 H), 4.7-4.9 (m, 1 H), 5.1-5.3 (m, 1 H), 5.70 (d, J=5 Hz, 1 H), 9.56 (d, J=3 Hz, 1 H).

EXAMPLE 43

The procedure of Example 41 was repeated except that 4.7 mg (0.01 mmole) of 20-(5,5-dimethyl-1,3-dioxan-2yl)-1α,2α-epoxypregna-5,7-dien-3β-yl acetate was used in lieu of 4.9 mg of 20-(5,5-dimethyl-1,3-dioxan-2-yl)-1α,2α-epoxy-7α-hydroxypregn-5-en-3β-yl acetate to give 2.6 mg of 3β-acetoxy-1α,2α-epoxypregna-5,7-diene-20-carbaldehyde (yield: 68%).

$^1$H-NMR spectrum (90 MHz) $\delta_{TMS}^{CDCl_3}$: 0.63 (s, 3 H), 1.01 (s, 3 H), 1.11 (d, J=6 Hz, 3 H), 2.10 (s, 3 H), 3.1-3.7 (m, 2 H), 5.0-5.7 (m, 3 H), 9.53 (d, J=3 Hz, 1 H).

EXAMPLE 44

The procedure of Example 36 was repeated except that 2.2 mg (0.005 mmole) of 20-(5,5-dimethyl-1,3-dioxan-2-yl)-1α,2α-epoxypregna-5,7-dien-3β-ol was used in lieu of 2.2 mg of 20-(5,5-dimethyl-1,3-dioxan-2-yl)-1α,2α-epoxypregn-5-ene-3β,7α-diol to give 1.0 mg of 1α,2α-epoxy-3β-hydroxypregna-5,7-diene-20-carbaldehyde (yield: 58%).

$^1$H-NMR spectrum (90 MHz) $\delta_{TMS}^{CDCl_3}$: 0.64 (s, 3 H), 1.02 (s, 3 H), 1.12 (d, J=6 Hz, 3 H), 3.1-3.7 (m, 2 H), 4.0-4.3 (m, 1 H), 5.3-5.5 (m, 1 H), 5.6-5.8 (m, 1 H), 9.55 (d, J=3 Hz, 1 H).

EXAMPLE 45

The procedure of Example 3 was repeated except that 2.72 g (43.8 mmoles) of ethylene glycol was used in lieu of 4.56 g of 2,2-dimethyl-1,3-propanediol to give 4.56 g of 20-(1,3-dioxolan-2-yl)pregna-1,4,6-trien-3-one (yield: 85%).

$^1$H-NMR spectrum (90 MHz) $\delta_{TMS}^{CDCl_3}$: 0.79 (s, 3 H), 1.08 (d, J=6 Hz, 3 H), 1.20 (s, 3 H), 3.7-4.0 (br, 4 H), 4.80 (br. s, 1 H, 5.9-6.3 (m, 3 H), 6.28 (dd, J=10, 1.5 Hz, 1 H), 7.10 (d, J=10 Hz, 1 H).

EXAMPLE 46

The procedure of Example 6 was repeated except that 4.16 g (11.3 mmoles) of 20-(1,3-dioxolan-2-yl)pregna-1,4,6-trien-3-one was used in lieu of 4.66 g of 20-(5,5-dimethyl-1,3-dioxan-2-yl)pregna-1,4,6-trien-3-one to give 3.25 g of 20-(1,3-dioxolan-2-yl)-1α,2α-epoxypregna-4,6-dien-3-one (yield: 75%).

$^1$H-NMR spectrum (90 MHz) $\delta_{TMS}^{CDCl_3}$: 0.78 (s, 3 H), 1.09 (d, J=6 Hz, 3 H), 1.19 (s, 3 H), 3.7-4.0 (br, 4 H), 4.80 (br. s, 1 H), 5.67 (s, 1 H), 6.09 (s, 2 H).

EXAMPLE 47

The procedure of Example 7 was repeated except that 0.295 g (0.769 mmole) of 20-(1,3-dioxolan-2-yl)-1α,-2α-epoxypregna-4,6-dien-3-one was used in lieu of 0.328 g of 20-(5,5-dimethyl-1,3-dioxan-2-yl)-1α,2α-epoxypregna-4,6-dien-3-one to give 0.231 g of 20-(1,3-dioxolan-2-yl)-1α,2α;6α,7βα -diepoxypregn-4-en-3-one (yield: 75%).

$^1$H-NMR spectrum (90 MHz) $\delta_{TMS}^{CDCl_3}$: 0.74 (s, 3 H), 1.06 (d, J=6 Hz, 3 H), 1.12 (s, 3 H), 3.2–3.7 (m, 4 H), 3.7–4.0 (br, 4 H), 4.79 (br. s, 1 H), 6.09 (d, 1 H).

EXAMPLE 48

The procedure of Example 9 was repeated except that 0.095 g (0.237 mmole) of 20-(1,3-dioxolan-2-yl)-1α,-2α;6α,7α-diepoxypregn-4-en-3-one was used in lieu of 0.105 g of 20-(5,5-dimethyl-1,3-dioxan-2-yl)-1α,2α;6α,-7α- diepoxypregn-4-en-3-one to give 0.074 g of 20-(1,3-dioxolan-2-yl)-1α,2α;6α,7α-diepoxypregn-4-en-3β-ol (yield: 78%).

$^1$H-NMR spectrum (90 MHz) $\delta_{TMS}^{CDCl_3}$: 0.72 (s, 3 H), 0.94 (s, 3 H), 1.05 (d, J=6 Hz, 3 H), 3.2–3.7 (m, 4 H), 3.7–4.0 (br, 4 H), 4.3–4.5 (br, 1 H), 4.79 (br. s, 1 H), 5.68 (dd, J=2.2, 1.9 Hz, 1 H).

EXAMPLE 49

The procedure of Example 10 was repeated except that 0.076 g (0.189 mmole) of 20-(1,3-dioxolan-2-yl)-1α,-2α;6α,7α-diepoxypregn-4-en-3β-ol was used in lieu of 0.084 g of 20-(5,5-dimethyl-1,3-dioxan-2-yl)-1α,2α;6α,-7α-diepoxypregn-4-en-3β-ol to give 0.074 g of 20-(1,3-dioxolan-2-yl)-1α,2α;6α,7α-diepoxypregn-4-en-3β-yl acetate (yield: 88%).

$^1$H-NMR spectrum (90 MHz) $\delta_{TMS}^{CDCl_3}$: 0.72 (s, 3 H), 0.97 (s, 3 H), 1.05 (d, J=6 Hz, 3 H), 2.13 (s, 3 H), 3.1–3.7 (m, 4 H), 3.7–4.0 (br, 4 H), 4.80 (br. s, 1 H), 5.5–5.7 (m, 2 H).

EXAMPLE 50

The procedure of Example 11 was repeated except that 24.9 mg (0.0561 mmole) of 20-(1,3-dioxolan-2-yl)-1α,2α;6α,7α-diepoxypregn-4-en-3β-yl acetate was used in lieu of 27.3 mg of 20-(5,5-dimethyl-1,3-dioxan-2-yl)-1α,2α;6α,7α-diepoxypregn-4-en-3β-yl acetate to give 9.5 mg of 20-(1,3-dioxolan-2-yl)-1α,2α-epoxy-7α-hydroxypregn-5-en-3β-yl acetate (yield: 38%) and, as a byproduct, 10.3 mg of 20-(1,3-dioxolan-2-yl)-1α,2α-epoxy-7α-hydroxypregn-4-en-3β-yl acetate (yield: 41%).

Analytical data on 20-(1,3-dioxolan-2-yl)-1α,2α-epoxy-7α-hydroxypregn-5-en-3β-yl acetate $^1$H-NMR spectrum (90 MHz) $\delta_{TMS}^{CDCl_3}$: 0.71 (s, 3 H), 1.05 (s, 3 H), 1.19 (d, J=13 Hz, 3 H), 2.10 (s, 3 H), 3.1–3.7 (m, 2 H), 3.7–4.0 (5 H), 4.81 (br. s, 1 H), 5.1–5.3 (m, 1 H), 5.72 (d, J=5 Hz, 1 H).

Analytical data on 20-(1,3-dioxolan-2-yl)-1α,2α-epoxy-7α-hydroxypregn-4-en-3β-yl acetate $^1$H-NMR spectrum (90 MHz) $\delta_{TMS}^{CDCl_3}$: 0.71 (s, 3 H), 1.07 (d, J=6 Hz, 3 H), 1.10 (s, 3 H), 2.15 (s, 3 H), 3.2–4.0 (7 H), 4.81 (br. s, 1 H), 5.15 (d, J=2 Hz, 1 H), 5.58 (dd, J=5.5, 3 Hz, 1 H).

EXAMPLE 51

The procedure of Example 12 was repeated except that 44.6 mg (0.1 mmole) of 20-(1,3-dioxolan-2-yl)-1α,2 -epoxy-7α-hydroxypregn-5-en-3β-yl acetate was used in lieu of 49.0 mg of 20-(5,5-dimethyl-1,3-dioxan-2-yl)-1α,2α-epoxy-7α-hydroxypregn-5-en-3β-yl acetate to give 37.8 mg of 20-(1,3-dioxolan-2-yl)-1α,2α-epoxy-7α-methoxycarbonyloxypregn-5-en-3β-yl acetate (yield: 75%)

$^1$H-NMR spectrum (90 MHz) $\delta_{TMS}^{CDCl_3}$: 0.71 (s, 3 H), 1.05 (s, 3 H), 1.19 (d, J=13 Hz, 3 H), 2.10 (s, 3 H), 3.1–4.0 (9 H), 4.81 (br. s, 1 H), 4.7–4.9 (br. s, 1 H), 5.1–5.3 (m, 1 H), 5.72 (d, J=5 Hz, 1 H).

EXAMPLE 52

The procedure of Example 17 was repeated except that 40.2 mg (0.0798 mmole) of 20-(1,3-dioxolan-2-yl)-1α,2α-epoxy-7α-methoxycarbonyloxypregn-5-en-3β-yl acetate was used in lieu of 43.6 mg of 20-(5,5-dimethyl-1,3-dioxan-2-yl)-1α,2α-epoxy-7α-methoxycarbonyloxypregn-5-en-3β-yl acetate to give 15.5 mg of 20-(1,3-dioxolan-2-yl)-1α,2α-epoxypregna-5,7-dien-3β-yl acetate. In addition, 14.2 mg of the starting compound 20-(1,3-dioxolan-2-yl)-1α,2α-epoxy-7α-methoxycarbonyloxypregn-5-en-3β-yl acetate was recovered. The yield of 20-(1,3-dioxolan-2-yl)-1α,2α-epoxypregna-5,7-dien-3β-yl acetate was 70% based on consumed 20-(1,3-dioxolan-2-yl)-1α,2α-epoxy-7α-methoxycarbonyloxypregn-5-en-3β-yl acetate.

$^1$H-NMR spectrum (90 MHz) $\delta_{TMS}^{CDCl_3}$: 0.63 (s, 3 H), 1.01 (s, 3 H), 1.11 (d, J=6 Hz, 3 H), 2.11 (s, 3 H), 2.3–2.6 (m, 2 H), 3.17 (d, J=4 Hz, 1 H), 3.2–4.0 (5 H), 4.81 (br. s, 1 H), 5.0–5.7 (m, 3 H).

EXAMPLE 53

The procedure of Example 23 was repeated except that 4.5 mg (0.0106 mmole) of 20-(1,3-dioxolan-2-yl)--epoxypregna-5,7-dien-3β-yl acetate was used in lieu of 5 mg of 20-(5,5-dimethyl-1,3-dioxan-2-yl)-1α,2α-epoxypregna-5,7-dien-3β-yl acetate to give 3.7 mg of 20-(1,3-dioxolan-2-yl)-1α,2α-epoxypregna-5,7-dien-3β-ol (yield: 90%).

$^1$H-NMR spectrum (90 MHz) $\delta_{TMS}^{CDCl_3}$: 0.63 (s, 3 H), 1.01 (s, 3 H), 1.11 (d, J=6 Hz, 3 H), 3.15 (d, J=4 Hz, 1 H), 3.2–4.0 (5 H), 4.0–4.3 (m, 1 H), 4.80 (br. s, 1 H), 5.3–5.5 (m, 1 H), 5.6–5.8 (m, 1 H).

EXAMPLE 54

The procedure of Example 24 was repeated except that 3.4 mg (0.00887 mmole) of 20-(1,3-dioxolan-2-yl)-1α,2α-epoxypregna-5,7-dien-3β-ol was used in lieu of 3.8 mg of 20-(5,5-dimethyl-1,3-dioxan-2-yl)-1α,2α-epoxypregna-5,7-dien-3β-ol to give 2.7 mg of 20-(1,3-dioxolan-2-yl)pregna-5,7-diene-1α,3β-diol (yield: 78%).

$^1$H-NMR spectrum (90 MHz) $\delta_{TMS}^{CDCl_3}$: 0.65 (s, 3 H), 0.93 (s, 3 H), 1.12 (d, J=6 Hz, 3 H), 3.2–4.0 (5 H), 4.0–4.3 (m, 1 H), 4.82 (br. s, 1 H), 5.3–5.5 (m, 1 H), 5.6–5.8 (m, 1 H).

EXAMPLE 55

The procedure of Example 25 was repeated except that 3.9 mg (0.010 mmole) of 20-(1,3-dioxolan-2-yl)-pregna-5,7-diene-1α,3β-diol was used in lieu of 4.3 mg of 20-(5,5-dimethyl-1,3-dioxan-2-yl)pregna-5,7-diene-1α,3β-diol to give 2.7 mg of 1α,3β-dihydroxypregna-5,7-diene-20-carbaldehyde (yield: 78%).

EXAMPLE 56

The procedure of Example 4 was repeated except that 3.2 g (100 mmoles) of methanol was used in lieu of 4.56 g of 2,2-dimethyl-1,3-propanediol to give 2.55 g of 7α-hydroxy-21,21-dimethoxy-20-methylpregna-1,4-dien-3-one (yield: 45%).

$^1$H-NMR spectrum (90 MHz) $\delta_{TMS}^{CDCl_3}$: 0.75 (s, 3 H), 1.06 (d, J=6 Hz, 3 H), 1.18 (s, 3 H), 3.38 (s, 3 H), 3.41 (s, 3 H), 3.97 (1 H), 4.40 (br. s, 1 H), 6.09 (1 H), 6.18 (dd, J=10, 1.5 Hz, 1 H), 7.02 (d, J=10 Hz, 1 H).

EXAMPLE 57

The procedure of Example 5 was repeated except that 2.50 g (6.44 mmoles) of 7α-hydroxy-21,21-dimethoxy-20-methylpregna-1,4-dien-3-one was used in lieu of 3.00 g of 20-(5,5-dimethyl-1,3-dioxan-2-yl)-7α-hydroxypregna-1,4-dien-3-one to give 2.00 g of 21,21-dimethoxy-20-methylpregna-1,4,6-trien-3-one (yield: 84%).

$^1$H-NMR spectrum (90 MHz) $\delta_{TMS}^{CDCl_3}$: 0.77 (s, 3 H), 1.07 (d, J=6 Hz, 3 H), 1.18 (s, 3 H), 3.38 (s, 3 H), 3.41 (s, 3 H), 4.39 (br. s, 1 H), 5.9–6.2 (m, 3 H), 6.22 (dd, J=10, 1.5 Hz, 1 H), 7.04 (d, J=10 Hz, 1 H).

EXAMPLE 58

To a solution of 2.00 g (5.4 mmoles) of 21,21-dimethoxy-20-methylpregna-1,4,6-trien-3-one in 70 ml of methanol were added a 10 wt % solution of sodium hydroxide in methanol (0.55 ml) and 3.04 ml of a 30 wt. % aqueous solution of hydrogen peroxide (containing 29.8 mmoles of hydrogen peroxide) and the mixture was stirred at room temperature for 14 hours. The reaction mixture was worked up in the same manner as Example 6 to recover 1.56 g of 1α,2α-epoxy-21,21-dimethoxy-20-methylpregna-4,6-dien-3-one (yield: 75%).

$^1$H-NMR spectrum (90 MHz) $\delta_{TMS}^{CDCl_3}$: 0.76 (s, 3 H), 1.06 (d, J=6 Hz, 3 H), 1.16 (s, 3 H), 3.2–3.7 (8 H), 4.38 (br. s, 1 H), 5.63 (s, 1 H), 6.05 (s, 2 H).

EXAMPLE 59

A mixture of 0.836 g (0.5 mmole) of m-chloroperbenzoic acid and 70 ml of chloroform was added to a mixture of 0.772 g (2.0 mmoles) of 1α,2α-epoxy-21,21-dimethoxy-20-methylpregna-4,6-dien-3-one and 20 ml of chloroform and the whole mixture was stirred at room temperature for 1 day. The reaction mixture thus obtained was worked up in the same manner as Example 7 to recover 0.498 g of 1α,2α;6α,7α-diepoxy-21,21-dimethoxy-20-methylpregn-4-en-3-one (yield: 62%).

$^1$H-NMR spectrum (90 MHz) $\delta_{TMS}^{CDCl_3}$: 0.72 (s, 3 H), 1.04 (d, J=6 Hz, 3 H), 1.10 (s, 3 H), 3.2–3.7 (10 H), 4.39 (br. s, 1 H), 6.08 (d, 1 H).

EXAMPLE 60

To a solution of 0.402 g (1 mmole) of 1α,2α;6α,7α-diepoxy-21,21-dimethoxy-20-methylpregn-4-en-3-one in 30 ml of tetrahydrofuran was added 38 mg (1 mmole) of sodium borohydride at a temperature of 0° C. and the mixture was stirred at 0° C. for 30 minutes. The reaction mixture was diluted with water and neutralized by adding cold 1N-hydrochloric acid in small portions. From this mixture, the tetrahydrofuran was distilled off under reduced pressure at a temperature not exceeding 20° C. and the residue was diluted with water and extracted with methylene chloride. The extract was washed with aqueous sodium chloride solution and dried over magnesium sulfate. The solvent was then distilled off under reduced pressure. Finally the residue was purified by silica gel chromatography (eluent: ethyl acetate-hexane =1:10, v/v) to recover 0.250 g of 1α,2α;6α,7α-diepoxy-21,21-dimethoxy-20-methylpregn-4-en-3β-ol (yield: 62%).

$^1$H-NMR spectrum (90 MHz) $\delta_{TMS}^{CDCl_3}$: 0.71 (s, 3 H), 0.93 (s, 3 H), 1.04 (d, J=6 Hz, 3 H), 3.2–3.7 (10 H), 4.3–4.5 (2 H), 5.69 (1 H).

EXAMPLE 61

To a mixture of 0.202 g (0.50 mmole) of 1α,2α;6α,7α-diepoxy-21,21-dimethoxy-20-methylpregn-4-en-3β-ol, 0.5 (6.18 mmoles) of dry pyridine and 10 m of methylene chloride was gradually added 0.1 ml (1.06 mmoles) of acetic anhydride dropwise at a temperature of 0° C. and the resulting solution was stirred at room temperature for 14 hours. The reaction mixture was then worked up in the same manner as Example 10 to recover 0.185 g of 1α,2α;6α,7α-diepoxy-21,21-dimethoxy-20-methylpregn-4-yl acetate (yield: 83%).

$^1$H-NMR spectrum (90 MHz) $\delta_{TMS}^{CDCl_3}$: 0.73 (s, 3 H), 0.97 (s, 3 H), 1.05 (d, J=6 Hz, 3 H), 2.13 (s, 3 H), 3.1–3.7 (10 H), 4.40 (br. s, 1 H), 5.5–5.7 (2 H).

EXAMPLE 62

The procedure of Example 11 was repeated except that 25.0 mg (0.0561 mmole) of 1α,2α;6α,7α-diepoxy-21,21-dimethoxy-20-methylpregn-4-en-3β-yl acetate was used in lieu of 27.3 mg of 20-(5,5-dimethyl-1,3-dioxan-2-yl)-1α,2α;6α,7α-diepoxypregn-4-en-3β-yl acetate to give 9.8 mg of 1α,2α-epoxy-7α-hydroxy-21,21-dimethoxy-20-methylpregn-5-en-3β-yl acetate (yield: 39%) and, as a byproduct, 10.6 mg of 1α,2α-epoxy-7α-hydroxy-21,21-dimethoxy-20-methylpregn-4-en-3β-yl acetate (yield: 42%).

Analytical data on
1α,2α-epoxy-7α-hydroxy-21,21-dimethoxy-20-methylpregn-5-en-3β-yl acetate $^1$H-NMR spectrum (90 MHz) $\delta_{TMS}^{CDCl_3}$: 0.70 (s, 3 H), 1.04 (s, 3 H), 1.18 (d, J=6 Hz, 3 H), 2.09 (s, 3 H), 3.1–3.7 (8 H), 3.7–3.9 (1 H), 4.39 (1 H), 5.1–5.3 (1 H), 5.70 (d, J=5 Hz, 1 H).

Analytical data on
1α,2α-epoxy-7α-hydroxy-1,21-dimethoxy-20-methylpregn-4-en-3β-yl acetate $^1$H-NMR spectrum (90 MHz) $\delta_{TMS}^{CDCl_3}$: 0.70 (s, 3 H), 1.06 (d, J=6 Hz, 3 H), 1.09 (s, 3 H), 2.14 (s, 3 H), 3.2–3.9 (9 H), 4.39 (br. s, 1 H), 5.14 (d, J=2 Hz, 1 H), 5.56 (dd, J=5.5, 3 Hz, 1 H).

EXAMPLE 63

The procedure of Example 12 was repeated except that 45.0 mg (0.1 mmole) of 1α,2α-epoxy-7α-hydroxy-21,21-dimethoxy-20-methylpregn-5-en-3β-yl acetate was used in lieu of 49.0 mg of 20-(5,5-dimethyl-1,3-dioxan2-yl)-1α,2α-epoxy-7α-hydroxypregn-5-en-3β-yl acetate to give 39.0 mg of 1α,2α-epoxy-21,21-dimethoxy-7α-methoxycarbonyloxy-20-methylpregn-5-en-3β-yl acetate (yield: 77%).

$^1$H-NMR spectrum (90 MHz) $\delta_{TMS}^{CDCl_3}$: 0.70 (s, 3 H), 1.03 (s, 3 H), 1.16 (d, J=6 Hz, 3 H), 2.10 (s, 3 H), 3.1–4.0 (11 H), 4.40 (br. s, 1 H), 4.7–4.9 (1 H), 5.1–5.3 (1 H), 5.70 (d, J=5 Hz, 1 H).

EXAMPLE 64

The procedure of Example 17 was repeated except that 40.4 mg (0.0798 mmole) of 1α,2α-epoxy-21,21-dimethoxy-7α-methoxycarbonyloxy-20-methylpregn-5-en-3β-yl acetate was used in lieu of 43.6 mg of 20-(5,5-dimethyl-1,3-dioxan-2-yl)-1α,2α-epoxy-7α-methoxycarbonyloxypregn-5-en-3β-yl acetate to give 15.6 mg of 1α,2α-epoxy-21,21-dimethoxy-20-methylpregna-5,7-dien-3β-yl acetate. In addition, 14.1 mg of the starting compound 1α,2α-epoxy-21,21-dimethoxy-7α-methoxycarbonyloxy-20-methylpregn-5-en-3β-yl acetate was recovered. The yield of 1α,2α-epoxy-21,21-dimethoxy-20-methylpregna-5,7-dien-3β-yl acetate was 70% based on consumed 1α,2α-epoxy-21,21-dimethoxy-7α-methoxycarbonyloxy-20-methylpregn-5-en-3β-yl acetate.

$^1$H-NMR spectrum (90 MHz) $\delta_{TMS}^{CDCl_3}$: 0.62 (s, 3 H), 0.99 (s, 3 H), 1.09 (d, J=6 Hz, 3 H), 2.09 (s, 3 H), 2.3–2.6 (m, 2 H), 3.16 (d, J=4 Hz, 1 H), 3.2–3.7 (7 H), 4.40 (br. s, 1 H), 5.0–5.7 (3 H).

EXAMPLE 65

The procedure of Example 23 was repeated except that 4.6 mg (0.0106 mmole) of 1α,2α-epoxy-21,21-dimethoxy-20-methylpregna-5,7-dien-3β-yl acetate was used in lieu of 5 mg of 20-(5,5-dimethyl-1,3-dioxan-2-yl)-1α,2α-epoxypregna-5,7-dien-3β-yl acetate to give 3.5 mg of 1α,2α-epoxy-21,21-dimethoxy-20-methylpregna-5,7-dien-3β-ol (yield: ca. 85%).

$^1$H-NMR spectrum (90 MHz) $\delta_{TMS}^{CDCl_3}$: 0.64 (s, 3 H), 1.01 (s, 3 H), 1.09 (d, J=6 Hz, 3 H), 3.16 (d, J=4 Hz, 1 H), 3.2–3.7 (7 H), 4.0–4.3 (1 H), 4.39 (br. s, 1 H), 5.3–5.5 (m, 1 H), 5.6–5.8 (m, 1 H).

EXAMPLE 66

The procedure of Example 24 was repeated except that 3.4 mg (0.00887 mmole) of 1α,2α-epoxy-21,21-dimethoxy-20-methylpregna-5,7-dien-3β-ol was used in lieu of 3.8 mg of 20-(5,5-dimethyl-1,3-dioxan-1,3-dioxan-2-yl)-1α,2α-epoxypregna-5,7-dien-3β-ol to give 2.6 mg of 21,21-dimethoxy-20-methylpregna-5,7-diene-1α,3α-diol (yield: ca. 75%).

$^1$H-NMR spectrum (90 MHz) $\delta_{TMS}^{CDCl_3}$: 0.64 (s, 3 H), 0.92 (s, 3 H), 1.11 (d, J=6 Hz, 3 H), 3.2–3.7 (7 H), 4.0–4.3 (m, 1 H), 4.40 (br. s, 1 H), 5.3–5.5 (m, 1 H), 5.6–5.8 (m, 1 H).

EXAMPLE 67

The procedure of Example 25 was repeated except that 2.6 mg (0.00667 mmole) of 21,21-dimethoxy-20-methylpregna-5,7-diene-1α,3β-diol was used in lieu of 4.3 mg of 20-(5,5-dimethyl-1,3-dioxan-2-yl)pregna-5,7-diene-1α,3β-diol to give 1.8 mg of 1α,3β-dihydroxypregna-5,7-diene-20-carbaldehyde (yield: 78%).

EXAMPLE 68

In 200 ml of ethanol was dissolved 13.0 g of 20-(5,5-dimethyl-1,3-dioxan-2-yl)-1α,2α-epoxypregna-4,6-dien-3-one, followed by addition of 1.0 g of sodium borohydride under ice-cooling. The mixture was stirred at room temperature for 2 hours. The resulting reaction mixture was neutralized with diluted hydrochloric acid under ice-cooling, diluted with water and extracted with methylene chloride. The extract was washed with aqueous sodium chloride solution and dried over magnesium sulfate. The solvent was then distilled off under reduced pressure to recover 12.1 g of a crude product. Purification of this crude product by silica gel chromatography gave 10.6 g of 20-(5,5-dimethyl-1,3-dioxan-2-yl)-1α,2α-epoxypregna-4,6-dien-3α-ol (yield: 81%) having the following physical properties.

$^1$H-NMR spectrum (90 MHz) $\delta_{TMS}^{CDCl_3}$: 0.70 (s, 3 H), 0.74 (s, 3 H), 1.07 (d, J=6.2 Hz, 3 H), 1.17 (s, 6 H), 3.11–3.74 (6 H), 4.38 (d, J=1.8 Hz, 1 H), 4.50 (br. s, 1 H), 5.18 (br. s, 1 H), 5.66 (d, J=9.7 Hz, 1 H), 5.90 (dd, J=9.7, 2 Hz, 1 H).

IR spectrum (KBr): 3480 cm$^{-1}$.

EXAMPLE 69

In 200 ml of tetrahydrofuran was dissolved 11.7 g of 20-(1,3-dioxolan-2-yl)-1α,2α-epoxypregna-4,6-dien-3-one, followed by addition of 36 ml of a 1.0M solution of diisobutylaluminum hydride in toluene under ice-cooling. The mixture was stirred under ice-cooling for minutes. Then, the reaction mixture was worked up in the same manner as Example 68 to recover 9.4 g of 20-(1,3-dioxolan-2-yl)-1α,2α-epoxypregna-4,6-dien-3α-ol (yield: 80%) showing the following physical properties.

$^1$H-NMR spectrum (90 MHz) $\delta_{TMS}^{CDCl_3}$: 0.79 (s, 3 H), 0.95 (d, J=6.2 Hz, 3 H), 1.17 (s, 3 H), 3.10–3.36 (2 H), 3.70–4.00 (4 H), 4.50 (br. s, 1 H), 4.80 (br. s, 1 H), 5.18 (br. s, 1 H), 5.66 (d, J=9.7 Hz, 1 H), 5.90 (dd, J=9.7, 2 Hz, 1 H).

IR spectrum (KBr): 3480 cm$^{-1}$.

EXAMPLE 70

In 200 ml of tetrahydrofuran was dissolved 11.8 g of 1α,2α-epoxy-21,21-dimethoxy-20-methylpregna-4,6-dien-3-one, followed by addition of 36 ml of a 1.0M solution of sodium triethylborohydride in tetrahydrofuran under ice-cooling. The mixture was stirred under ice-cooling for 15 minutes, after which it was worked up in the same manner as Example 68 to give 10.24 g of 1α,2α-epoxy-21,21-dimethoxy-20-methylpregna-4,6-dien-3α-ol (yield: 85%) showing the following physical properties.

$^1$H-NMR spectrum (90 MHz) $\delta_{TMS}^{CDCl_3}$: 0.75 (s, 3 H), 0.96 (d, J=6.2 Hz, 3 H), 1.16 (s, 3 H), 3.10–3.36 (2 H), 3.38 (s, 3 H), 3.41 (s, 3 H), 4.38 (br. s, 1 H), 4.51 (br. s, 1 H), 5.18 (br. s, 1 H), 5.66 (d, J=9.7 Hz, 1 H), 5.90 (dd, J=9.7, 2 Hz, 1 H).

IR spectrum (KBr): 3480 cm$^{-1}$.

EXAMPLE 71

In 250 ml of methylene chloride was dissolved 10.6 g of 20-(5,5-dimethyl-1,3-dioxan-2-yl)-1,α2α-epoxypregna-4,6-dien-3α-ol and the solution was stirred under ice-cooling. To this solution were added 200 ml of saturated aqueous sodium hydrogen carbonate solution and 7.67 g of 80% m-chloroperbenzoic acid, and the solution was stirred at room temperature for 2 hours. The organic layer was separated from the reaction mixture and the aqueous layer was extracted with ethyl acetate. The organic layer was combined with the extract and the mixture was washed successively with water, aqueous potassium iodide solution, aqueous sodium thiosulfate solution, water, aqueous sodium hydrogen carbonate solution and aqueous sodium chloride solution and dried over potassium carbonate. The solution was then concentrated under reduced pressure to recover 15.5 g of 20-(5,5-dimethyl-1,3-dioxan-2-yl)-1α,2α;4α,5α-diepoxypregn-6-en-3α-ol as a substantially pure product showing the following physical properties.

¹H-NMR spectrum (90 MHz) $\delta_{TMS}{}^{CDCl_3}$: 0.70 (s, 3 H), 0.74 (s, 3 H), 1.07 (d, J=6.2 Hz, 3 H), 1.18 (s, 6H), 3.04-3.75 (7 H), 4.24 (br. s, 1 H), 4.38 (d, J=1.8 Hz, 1 H), 5.14 (dd, J=9.9 Hz, 2.0 Hz, 1 H), 5.88 (d, J=9.9 Hz, 1 H).

IR spectrum (KBr): 3400 cm$^{-1}$.

EXAMPLE 72

The procedure of Example 71 was repeated except that the reaction was conducted using 9.56 g of 20-(1,3-dioxolan-2-yl)-1α,2α-epoxypregna-4,6-dien-3α-ol in lieu of 10.6 g of 20-(5,5-dimethyl-1,3-dioxan-2-yl)-1α,2α-epoxypregna-4,6-dien-3α-ol in the absence of an aqueous sodium hydrogen carbonate solution to give 13.3 g of 20-(1,3-dioxolan-2-yl)-1α,2α;4α,5α-diepoxypregn-6-en-3α-ol. This is a substantially pure product showing the following physical properties.

¹H-NMR spectrum (90 MHz) $\delta_{TMS}{}^{CDCl_3}$: 0.78 (s, 3 H), 0.94 (d, J=6.2 Hz, 3 H), 1.18 (s, 3 H), 3.04-3.40 (3 H), 3.72-3.98 (4 H), 4.24 (br. s, 1 H), 4.79 (d, J=1.8 Hz, 1 H), 5.15 (dd, J=9.8 Hz, 2.0 Hz, 1 H), 5.90 (d, J=9.9 Hz, 1 H).

IR spectrum (KBr): 3420 cm$^{-1}$.

EXAMPLE 73

The procedure of Example 71 was repeated except that 9.61 g of 1α,2α-epoxy-21,21-dimethoxy-20-methylpregna-4,6-dien-3α-ol was used in lieu of 10.6 g of 20-(5,5-dimethyl-1,3-dioxan-2-yl)-1α,2α-epoxypregna-4,6-dien-3α-ol to give 14.2 g of 1α,2α;4α,5α-diepoxy-21,21-dimethoxy-20-methylpregn-6-en-3α-ol as a substantially pure product showing the following physical properties.

¹H-NMR spectrum (90 MHz) $\delta_{TMS}{}^{CDCl_3}$: 0.76 (s, 3 H), 0.97 (d, J=6.2 Hz, 3 H), 1.18 (s, 3 H), 3.05-3.42 (3 H), 3.38 (s, 3 H), 3.42 (s, 3 H), 4.24 (br. s, 1 H), 4.39 (br. s, 1 H), 5.14 (dd, J=9.8 Hz, 2.0 Hz, 1 H), 5.89 (d, J=9.9 Hz, 1 H).

IR spectrum (KBr): 3450 cm$^{-1}$.

EXAMPLE 74

In 100 ml of methylene chloride was dissolved 15.5 g of the 20-(5,5-dimethyl-1,3-dioxan-2-yl)-1α,2α;4α,5α-diepoxypregn-6-en-3α-ol obtained in Example 71. This solution was added dropwise, under ice-cooling, to a complex prepared from 45 ml of pyridine and 24.8 g of chromium oxide in 160 ml of methylene chloride and after completion of dropwise addition, the mixture was further stirred under ice-cooling for 1 hour. The reaction mixture thus obtained was diluted with ethyl acetate and filtered with the aid of Celite. The filtrate was washed successively with water, aqueous copper sulfate solution, water, aqueous sodium hydrogen carbonate solution and aqueous sodium chloride solution and dried over sodium sulfate. Finally, the solution was concentrated under reduced pressure to recover 8.9 g of 20-(5,5-dimethyl-1,3-dioxan-2-yl)-1α,2α;4α,5α-diepoxypregn-6-en-3-one as a substantially pure product showing the following physical properties.

¹H-NMR spectrum (90 MHz) $\delta_{TMS}{}^{CDCl_3}$: 0.70 (s, 3 H), 0.74 (s, 3 H), 1.07 (d, J=6.2 Hz, 3 H), 1.08 (s, 3H), 1.12 (s, 3 H), 3.20-3.67 (7 H), 4.38 (br. s, 1 H), 5.05 (d, J=9.8 Hz, 1 H), 5.95 (d, J=9.8 Hz, 1 H).

IR spectrum (KBr): 1705 cm$^{-1}$.

EXAMPLE 75

The procedure of Example 74 was repeated except that 13.3 g of the 20-(1,3-dioxolan-2-yl)-1α,2α;4α,5α-diepoxypregn-6-en-3α-ol prepared in Example 72 was used in lieu of 15.5 g of 20-(5,5-dimethyl-1,3-dioxan-2-yl)-1α,2α;4α,5α-diepoxypregn-6-en-3α-ol to give 9.1 g of 20-(1,3-dioxolan-2-yl)-1α,2α;4α,5α-diepoxypregn-6-en-3-one as a substantially pure product showing the following physical properties.

¹H-NMR spectrum (90 MHz) $\delta_{TMS}{}^{CDCl_3}$: 0.79 (s, 3 H), 0.96 (d, J=6.2 Hz, 3 H), 1.12 (s, 3 H), 3.20-3.40 (3 H), 3.69-4.00 (4 H), 4.80 (br. s, 1 H), 5.05 (d, J=9.8 Hz, 1 H), 5.95 (d, J=9.8 Hz, 1 H).

IR spectrum (KBr): 1705 cm$^{-1}$.

EXAMPLE 76

The procedure of Example 74 was repeated except that 14.2 g of 1α,2α;4α,5α-diepoxy-21,21-dimethoxy-20-methylpregn-6-en-3α-ol prepared in Example 73 was used in lieu of 15.5 g of 20-(5,5-dimethyl-1,3-dioxan-2-yl)-1α,2α;4α,5α-diepoxypregn-6-en-3α-ol to give 8.5 g of 1α,2α;4α,5α-diepoxy-21,21-dimethoxy-20-methylpregn-6-en-3-one as a substantially pure product showing the following physical properties.

¹H-NMR spectrum (90 MHz) $\delta_{TMS}{}^{CDCl_3}$: 0.75 (s, 3H), 0.98 (d, J=6.2 Hz, 3 H), 1.13 (s, 3 H), 3.20-3.40 (3 H), 3.39 (s, 3 H), 3.42 (s, 3 H), 4.39 (br. s, 1 H), 5.05 (d, J=9.8 Hz, 1 H), 5.95 (d, J=9.8 Hz, 1H).

IR spectrum (KBr): 1705 cm$^{-1}$.

EXAMPLE 77

In 10 ml of toluene was dissolved 1.5 g of the 20-(5,5-dimethyl-1,3-dioxan-2-yl)-1α,2α;4α,5α-diepoxypregn-6-en-3α-ol, followed by addition of 0.62 g of benzoic acid and 1.07 g of triphenylphosphine. The mixture was stirred under ice-cooling. To the mixture thus obtained, 0.71 g of diethyl azodicarboxylate was added dropwise and the mixture was stirred under ice-cooling for 30 minutes. The resulting reaction mixture was poured in water and extracted with ether. The extracts were combined, washed with aqueous sodium chloride solution and dried over sodium sulfate, followed by concentration under reduced pressure. The procedure yielded 1.6 g of substantially pure 20-(5,5-dimethyl-1,3-dioxan-2-yl)-1α,2α;4α,5α-diepoxy-3β-benzoyloxypregn-6-ene having the following physical properties.

¹H-NMR spectrum (90 MHz) $\delta_{TMS}{}^{CDCl_3}$: 0.65 (s, 3H), 0.70 (s, 3 H), 1.00 (d, J=6.2 Hz, 3 H), 1.12 (s, 6 H), 2.70-3.80 (7 H), 4.38 (br. s, 1 H), 5.11 (dd, J=9.6, 2.0 Hz, 1 H), 5.50 (br. s, 1 H), 5.84 (d, J=9.6 Hz, 1 H), 7.2-7.7 (m, 3 H), 7.9-8.2 (m, 2 H).

IR spectrum (KBr): 1720 cm$^{-1}$.

EXAMPLE 78

The procedure of Example 77 was repeated except that 1.4 g of the 20-(1,3-dioxolan-2-yl)-1α,2α;4α,5α-diepoxypregn-6-en-3α-ol prepared in Example 72 and 0.27 g of acetic acid were used in lieu of 1.5 g of 20-(5,5-dimethyl-1,3-dioxan-2-yl)-1α,2α;4α,5α-diepoxypregn-6-en-3α-ol and 0.62 g of benzoic acid, respectively, to give 1.5 g of 20-(1,3-dioxolan-2-yl)-3β-acetoxy-1α,2α;4α,5α-diepoxypregn-6-ene as a substantially pure product showing the following physical properties.

¹H-NMR spectrum (90 MHz) $\delta_{TMS}{}^{CDCl_3}$: 0.75 (s, 3 H), 0.94 (d, J=6.2 Hz, 3 H), 1.12 (s, 3 H), 2.07 (s, 3 H), 3.1-3.5 (3 H), 3.7-4.0 (4 H), 4.81 (br. s, 1 H), 5.12 (d, J=9.6 Hz, 1 H), 5.38 (br. s, 1 H), 5.85 (d, J=9.5 Hz, 1 H).

IR spectrum (KBr): 1735 cm$^{-1}$.

EXAMPLE 79

The procedure of Example 77 was repeated except that 1.4 g of the 1α,2α;4α,5α-diepoxy-21,21-dimethoxy-20-methylpregna-6-dien-3α-ol prepared in Example 73 was used in lieu of 1.5 g of 20-(5,5-dimethyl-1,3-dioxan-2-yl)-1α,2α;4α,5α-diepoxypregn-6-en-3α-ol to give 1.6 g of 3β-benzoyloxy-1α,2α;4α,5α-diepoxy-21,21-dimethoxy-20-methylpregn-6-ene as a substantially pure product showing the following physical properties.

$^1$H-NMR spectrum (90 MHz) $\delta_{TMS}^{CDCl_3}$: 0.76 (s, 3 H), 0.97 (d, J=6.2 Hz, 3 H), 1.18 (s, 3 H), 3.1-3.5 (3 H), 3.38 (s, 3 H), 3.42 (s, 3 H), 4.38 (br. s, 1 H), 5.11 (dd, J=9.6, 2.0 Hz, 1 H), 5.50 (br. s, 1 H), 5.84 (d, J=9.6 Hz, 1 H), 7.2-7.7 (m, 3 H), 7.9-8.2 (m, 2 H).

IR spectrum (KBr): 1720 cm$^{-1}$.

EXAMPLE 80

In 20 ml of methanol was dissolved 1.6 g of the 20-(5,5-dimethyl-1,3-dioxan-2-yl)-1α,2α;4α,5α-diepoxy-3β-benzoyloxypregn-6-ene obtained in Example 77, followed by addition of 1.0 g of potassium carbonate. The mixture was stirred under ice-cooling for 2 hours. The reaction mixture thus obtained was poured in water and extracted with ether. The extracts were pooled, washed with aqueous sodium chloride solution and dried over sodium sulfate, followed by concentration under reduced pressure. The procedure yielded 1.2 g of substantially pure 20-(5,5-dimethyl-1,3-dioxan-2-yl)-1α,2α;4α,5α-diepoxypregn-6-en-3β-ol having the following physical properties.

$^1$H-NMR spectrum (90 MHz) $\delta_{TMS}^{CDCl_3}$: 0.65 (s, 3 H), 0.70 (s, 3 H), 1.00 (d, J=6.2 Hz, 3 H), 1.12 (s, 6 H) 2.70-3.80 (7 H), 4.33 (br. s, 1 H), 4.58 (1 H), 5.12 (d, J=9.6 Hz, 1 H), 5.85 (d, J=9.5 Hz, 1 H).

IR spectrum (KBr): 3450 cm$^{-1}$.

EXAMPLE 81

The procedure of Example 80 was repeated except that 1.5 g of the 20-(1,3-dioxolan-2-yl)-3β-acetoxy-1α,2α;4α,5α-diepoxypregn-6-ene prepared in Example 78 was used in lieu of 1.6 g of 20-(5,5-dimethyl-1,3-dioxan-2-yl)-1α,2α;4α,5α-diepoxy-3β-benzoyloxypregn-6-ene to give 1.1 g of 20-(1,3-dioxolan-2-yl)-3β-acetoxy-1α,2α;4α,5α-diepoxypregn-6-en-3β-ol as a substantially pure product showing the following physical properties.

$^1$H-NMR spectrum (90 MHz) $\delta_{TMS}^{CDCl_3}$: 0.75 (s, 3 H), 0.94 (d, J=6.2 Hz, 3 H), 1.12 (s, 3 H), 3.1-3.5 (3 H), 3.7-4.0 (4 H), 4.57 (1 H), 4.81 (br. s, 1 H), 5.12 (d, J=9.6 Hz, 1 H), 5.85 (d, J=9.6 Hz, 1 H).

IR spectrum (KBr): 3450 cm$^{-1}$.

EXAMPLE 82

The procedure of Example 80 was repeated except that 1.6 g of the 3β-benzoyloxy-1α,2α;4α,5α-diepoxy-21,21-dimethoxy-20-methylpregn-6-ene prepared in Example 79 was used in lieu of 1.6 g of 20-(5,5-dimethyl-1,3-dioxan-2-yl)-1α,2α;4α,5α-diepoxy-3β-benzoyloxypregn-6-ene to give 1.1 g of 1α,2α;4α,5α-diepoxy-21,21-dimethoxy-20-methylpregn-6-en-3β-ol as a substantially pure product showing the following physical properties.

$^1$H-NMR spectrum (90 MHz) $\delta_{TMS}^{CDCl_3}$: 0.76 (s, 3 H), 0.97 (d, J=6.2 Hz, 3 H), 1.18 (s, 3 H), 3.1-3.5 (3 H), 3.38 (s, 3 H), 3.42 (s, 3 H), 4.38 (br. s, 1 H), 4.55 (br. s, 1 H), 5.11 (dd, J=9.6, 2.0 Hz, 1 H), 5.84 (d, J=9.6 Hz, 1 H).

IR spectrum (KBr): 3450 cm$^{-1}$.

EXAMPLE 83

In 20 ml of ethanol was dissolved 2.0 g of the 20-(5,5-dimethyl-1,3-dioxan-2-yl)-1α,2α;4α,5α-diepoxypregn-6-en-3-one obtained in Example 74, followed by addition of 0.2 g of sodium borohydride under ice-cooling. The mixture was stirred under ice-cooling for 2 hours. The reaction mixture thus obtained was poured in water and extracted with ether. The extracts were pooled, washed with aqueous sodium chloride solution and dried over sodium sulfate, followed by concentration under reduced pressure. The procedure gave 1.5 g of substantially pure 20-(5,5-dimethyl-1,3-dioxan-2-yl)-1α,2α;4α,5α-diepoxypregn-6-en-3β-ol showing physical properties identical with those of the compound obtained in Example 80.

EXAMPLE 84

The procedure of Example 83 was repeated except that 1.8 g of the 20-(1,3-dioxolan-2-yl)-1α,2α;4α,5α-diepoxypregn-6-en-3-one prepared in Example 75 was used in lieu of 2.0 g of 20-(5,5-dimethyl-1,3-dioxan-2-yl)-1α,2α;4α,5α-diepoxypregn-6-en-3-one to give 1.1 g of 20-(1,3-dioxolan-2-yl)-1α,2α;4α,5α-diepoxypregn-6-en-3β-ol as a substantially pure product showing the same physical properties as the compound obtained in Example 81.

EXAMPLE 85

The procedure of Example 83 was repeated except that 1.8 g of 1α,2α;4α,5α-diepoxy-21,21-dimethoxy-20-methylpregn-6-en-3-one prepared in Example 76 was used in lieu of 2.0 g of 20-(5,5-dimethyl-1,3-dioxan-2-yl)-1α,2α;4α,5α-diepoxypregn-6-en-3-one to give 1.1 g of 1α,2α;4α,5α-diepoxy-21,21-dimethoxy-20-methylpregn-6-en-3β-ol as a substantially pure product showing the same physical properties as the compound obtained in Example 82.

EXAMPLE 86

In 10 ml of methylene chloride was dissolved 0.1 g of 20-(5,5-dimethyl-1,3-dioxan-2-yl)-1,α2α;4α,5α-diepoxypregn-6-en-3β-ol, followed by addition of 1 ml of pyridine and 0.05 g of N,N-dimethyl-4-aminopyridine. Then, 0.1 ml of methyl chlorocarbonate was added slowly dropwise under ice-cooling, and the resulting mixture was stirred at room temperature for 3 hours. The reaction mixture thus obtained was poured in cold diluted hydrochloric acid and extracted with methylene chloride. The extracts were pooled, washed with water, aqueous copper sulfate solution, water, aqueous sodium hydrogen carbonate solution and aqueous sodium chloride solution in that order and dried over sodium sulfate. The solution was concentrated under reduced pressure to recover 0.11 g of substantially pure 20-(5,5-dimethyl-1,3-dioxan-2-yl)-1,α2α;4α,5α-diepoxy-3β-methoxycarbonyloxypregn-6-ene having the following physical properties.

$^1$H-NMR spectrum (90 MHz) $\delta_{TMS}^{CDCl_3}$: 3.77 (s, 3 H).

IR spectrum (KBr): 1745 cm.$^{-1}$.

EXAMPLE 87

In 10 ml of toluene was dissolved 0.1 g of 20-(1,3-dioxolan-2-yl)-1α,2α;4α,5α-diepoxypregn-6-en-3β-ol, followed by addition of one drop of pyridine. Then, 0.2 ml of methyl isocyanate was added under ice-cooling.

The mixture was stirred at a temperature of 60° C. for 30 minutes. The reaction mixture thus obtained was poured in ice-water and extracted with methylene chloride. The extracts were pooled, washed with water and aqueous sodium chloride solution and dried over sodium sulfate, followed by concentration under reduced pressure. The procedure gave 0.11 g of substantially pure 20-(1,3-dioxolan-2-yl)-1α,2α;4α,5α-diepoxy-3β-(N-methylcarbamoyl)oxypregn-6-ene showing the following physical properties.

$^1$H-NMR spectrum (90 MHz) $\delta_{TMS}^{CDCl_3}$: 2.80 (d, J=6 Hz, 3 H).

IR spectrum (KBr): 1710 cm$^{-1}$.

EXAMPLE 88

In 10 ml of toluene was dissolved 0.1 g of 1α, 2α;4α,-5α-diepoxy-21,21-dimethoxy-20-methylpregn-6-en-3β-ol, followed by addition of one drop of pyridine. Then, 0.14 ml of phenyl isocyanate was added under ice-cooling. This solution was stirred at a temperature of 60° C. for 30 minutes. The reaction mixture thus obtained was poured in ice-water and extracted with methylene chloride. The extracts were pooled, washed with water and aqueous sodium chloride solution and dried over sodium sulfate, followed by concentration under reduced pressure. The procedure gave 0.12 g of substantially pure 1α,2α;4α,5α-diepoxy-21,21-dimethoxy-20-methyl-3β-(N-phenylcarbamoyl)oxypregn-6-ene showing the following physical properties.

$^1$H-NMR spectrum (90 MHz) $\delta_{TMS}^{CDCl_3}$: 6.92 (br. s, 1 H), 7.1-7.7 (m, 5 H).

IR spectrum (KBr): 1725 cm$^{-1}$.

EXAMPLE 89

In 10 ml of toluene was dissolved 0.1 g of 20-(5,5-dimethyl-1,3-dioxan-2-yl)-1α,2α;4α,5α-diepoxypregn-6-en-3β-ol, followed by addition of 1 ml of pyridine and 0.05 g of N,N-dimethyl-4-aminopyridine. Then, 0.1 ml of N,N-dimethylcarbamoyl chloride was slowly added dropwise under ice-cooling. The mixture was stirred at 60° C. for 10 hours, at the end of which time the mixture was poured in cold diluted hydrochloric acid and extracted with methylene chloride. The extracts were pooled, washed successively with water, aqueous copper sulfate solution, water, aqueous sodium hydrogen carbonate solution and aqueous sodium chloride solution and dried over sodium sulfate, followed by concentration under reduced pressure. The procedure gave 0.12 g of substantially pure 20-(5,5-dimethyl-1,3-dioxan-2-yl)-1α,2α;4α,5α-diepoxy-3β-(N,N-dimethylcarbamoyl)oxypregn-6-ene showing the following physical properties.

$^1$H-NMR spectrum (90 MHz) $\delta_{TMS}^{CDCl_3}$: 2.79 (s, 3 H), 2.82 (s, 3 H).

IR spectrum (KBr): 1690 cm$^{-1}$.

EXAMPLE 90

In 5 ml of N,N-dimethylformamide was dissolved 0.1 g of 20-(5,5-dimethyl-1,3-dioxan-2-yl)-1α,2α;4α,5α-diepoxypregn-6-en-3β-ol, followed by addition of 0.15 g of imidazole and 0.17 g of tert-butyldimethylsilyl chloride. The mixture was stirred at room temperature for 10 hours. The reaction mixture thus obtained was poured in water and extracted with ether. The extracts were pooled, washed with water and aqueous sodium chloride solution and dried over sodium sulfate, followed by concentration under reduced pressure. The procedure gave 0.12 g of substantially pure 20-(5,5-dimethyl-1,3-dioxan-2-yl)-1α,2α;4α,5α-diepoxy-3β-(tert-butyldimethylsilyl)oxypregn-6-ene showing the following physical properties.

$^1$H-NMR spectrum (90 MHz) $\delta_{TMS}^{CDCl_3}$: 0.15 (s, 6 H), 0.94 (s, 9 H).

EXAMPLE 91

In 2 ml of tetrahydrofuran was dissolved 0.1 g of 20-(1,3-dioxolan-2-yl)-1α, 2α;4α,5α-diepoxypregn-6-en-3β-ol and the solution was added to a suspension of 0.015 g of 60% sodium hydride in 5 ml of tetrahydrofuran. The mixture was stirred at room temperature for 1 hour, at the end of which time 0.03 g of chloromethyl methyl ether was added. The mixture was stirred at a temperature of 40° C. for 4 hours. The reaction mixture thus obtained was poured in ice-water and extracted with ether. The extracts were pooled, washed successively with aqueous sodium hydrogen carbonate solution and aqueous sodium chloride solution, and dried over sodium sulfate, followed by concentration under reduced pressure. The procedure gave 0.10 g of substantially pure 20-(1,3-dioxolan-2-yl)-1α,2α;4α,5α-diepoxy-3β-(methoxymethyl)oxypregn-6-ene showing the following physical properties.

$^1$H-NMR spectrum (90 MHz) $\delta_{TMS}^{CDCl_3}$: 3.34 (s, 3 H), 4.65 (br. s, 2 H).

EXAMPLE 92

The procedure of Example 90 was repeated except that 0.1 g of 1α,2α;4α,5α-diepoxy-21,21-dimethoxy-20-methylpregn-6-en-3β-ol was used in lieu of 0.1 g of 20-(5,5-dimethyl-1,3-dioxan-2-yl)-1α,2α;4α,5α-diepoxypregn-6-en-3β-ol to give 0.11 g of 3β-(tert-butyldimethylsilyl)oxy-1α,2α;4α,5α-diepoxy-21,21-dimethoxy-20-methylpregn-6-ene as a substantially pure product showing the following physical properties.

$^1$H-NMR spectrum (90 MHz) $\delta_{TMS}^{CDCl_3}$: 0.12 (s, 6 H), 0.92 (s, 9 H).

EXAMPLE 93

In 20 ml of tetrahydrofuran was dissolved 8.9 g of the 20-(5,5-dimethyl-1,3-dioxan-2-yl)-1α, 2α;4α,5α-diepoxypregn-6-ene-3-one obtained in Example 74 and the solution was added dropwise to a suspension of 2.8 g of lithium aluminum hydride in 50 ml of tetrahydrofuran under ice-cooling. After completion of dropwise addition, the mixture was stirred at room temperature for 2 hours. The excess reducing agent was decomposed with saturated aqueous sodium sulfate solution and the mixture was filtered with the aid of Celite. The residue was washed thoroughly with ethyl acetate and the washings were combined with the filtrate. This solution was concentrated under reduced pressure and the concentrate was recrystallized from ethyl acetate. The procedure yielded 2.93 g of 20-(5,5-dimethyl-1,3-dioxan-2-yl)pregn-6-ene-1α,3β,5α-triol showing the following physical properties.

$^1$H-NMR spectrum (90 MHz) $\delta_{TMS}^{CDCl_3}$: 0.70 (s, 3H), 0.71 (s, 3 H), 0.88 (s, 3 H), 1.05 (d, J=6.2 Hz, 3 H), 1.17 (3 H, s), 3.34 (d, J=10.6 Hz, 1 H), 3.43 (d, J=10.6 Hz, 1 H), 3.58 (d, 10.6 Hz, 2 H), 3.84 (m, 1 H), 4.11 (d, J=10.3 Hz, 1 H), 4.38 (d, J=2.5 Hz, 1 H), 5.56 (d, J=9.7 Hz, 1 H), 5.71 (d, J=9.7 Hz, 1 H).

IR spectrum (KBr): 3500 cm$^{-1}$.

EXAMPLE 94

In 50 ml of tetrahydrofuran was dissolved 9.1 g of the 20-(1,3-dioxolan-2-yl)-1α,2α;4α,5α-diepoxypregn-6-en- 3-one, followed by addition of 22 ml of a 3.4M solution of sodium bis(2-methoxyethoxy)aluminum hydride in toluene under ice-cooling. The mixture was stirred at room temperature for 2 hours. After the excess reducing agent was decomposed with saturated aqueous sodium sulfate solution, the reaction mixture was filtered with the aid of Celite. The residue was thoroughly washed with ethyl acetate and the washings were combined with the filtrate. This solution was concentrated under reduced pressure and the concentrate was recrystallized from ethyl acetate to give 2.75 g of 20-(1,3-dioxolan-2-yl)pregn-6-ene-1α,3β,5α-triol showing the following physical properties.

$^1$H-NMR spectrum (90 MHz) $\delta_{TMS}^{CDCl_3}$: 0.75 (s, 3 H), 0.88 (s, 3 H), 0.97 (d, J=6.2 Hz, 3 H), 3.65-4.01 (m, 4 H), 3.84 (m, 1 H), 4.11 (d, J=10.3 Hz, 1 H), 4.79 (d, J=2.5 Hz, 1 H), 5.56 (d, J=9.7 Hz, 1 H), 5.71 (d, J=9.7 Hz, 1 H).

IR spectrum (KBr): 3450 cm$^{-1}$.

EXAMPLE 95

In 50 ml of tetrahydrofuran was dissolved 8.5 g of the 1α,2α;4α,5α-diepoxy-21,21-dimethoxy-20-methylpregn-6-en-3-one obtained in Example 76, followed by dropwise addition of 100 ml of a 1.0M solution of lithium tri-sec-butylborohydride in tetrahydrofuran under ice-cooling. After completion of dropwise addition, the mixture was stirred at room temperature for 2 hours. The excess reducing agent was decomposed with water and the residual alkylborane was decomposed with alkaline hydrogen peroxide, followed by extraction with ethyl acetate. The extracts were pooled, washed with aqueous sodium chloride solution, and dried over sodium sulfate, followed by concentration under reduced pressure. Recrystallization of the concentrate from ethyl acetate gave 2.90 g of 21,21-dimethoxy-20-methylpregn-6-ene-1α,3β,5a-triol showing the following physical properties.

$^1$H-NMR spectrum (90 MHz) $\delta_{TMS}^{CDCl_3}$: 0.75 (s, 3 H), 0.88 (s, 3 H), 0.97 ( d, J=6.2 Hz, 3 H), 3.75 (s, 3 H), 3.81 (s, 3 H), 3.84 (m, 1 H), 4.11 (d, J=10.3 Hz, 1 H), 4.40 (br. s, 1 H), 5.56 (d, J=9.7 Hz, 1 H), 5.71 (d, J=9.7 Hz, 1 H).

IR spectrum (KBr): 3450 cm$^{-1}$.

EXAMPLE 96

In 5 ml of tetrahydrofuran was dissolved 0.1 g of 20-(5,5-dimethyl-1,3-dioxan-2-yl)-1α,2α;4α,5α-diepoxypregn-6-en-3β-ol and the solution was added dropwise to a suspension of 0.05 g of lithium aluminum hydride in 5 ml of tetrahydrofuran under ice-cooling. After completion of dropwise addition, the mixture was stirred at room temperature for 2 hours. Thereafter, the reaction mixture was worked up in the same manner as Example 93 to recover 0.07 g of 20-(5,5-dimethyl-1,3-dioxan-2-yl)-pregn-6-ene-1α,3β-5α-triol having the same physical properties as the compound obtained in Example 93.

EXAMPLE 97

In 5 ml of tetrahydrofuran was dissolved 0.1 g of 20-(5,5-dimethyl-1,3-dioxan-2-yl)-1α,2α;4α,5α-diepoxy-3β-methoxycarbonyloxypregn-6-ene, followed by addition of 0.2 ml of a 3.4M solution of sodium bis(2-methoxyethoxy)aluminum hydride in toluene under ice-cooling. The mixture was stirred at room temperature for 2 hours. Thereafter, the same workup procedure as described in Example 94 was followed to recover 0.05 g of 20-(5,5-dimethyl-1,3-dioxan-2-yl)pregn-6-ene-1α,3β,5α-triol showing the same physical properties as the compound obtained in Example 93.

EXAMPLE 98

In 5 ml of tetrahydrofuran was dissolved 0.1 g of 20-(1,3-dioxolan-2-yl)-3β-acetoxy-1α,2α;4α,5α-diepoxypregn-6-ene, followed by dropwise addition of 1 ml of a 1.0M solution of lithium tri-sec-butylborohydride in tetrahydrofuran under ice-cooling. After completion of dropwise addition, the mixture was stirred at room temperature for 2 hours. Thereafter, the same workup procedure as described in Example 95 was followed to recover 0.06 g of 20-(1,3-dioxolan-2-yl)pregn-6-ene-1α,3β,5α-triol showing the same physical properties as the compound obtained in Example 94.

EXAMPLE 99

In 5 ml of tetrahydrofuran was dissolved 0.1 g of 20-(1,3-dioxolan-2-yl)-1α,2α;4α,5α-diepoxy-3β-(N-methylcarbamoyl)oxypregn-6-ene and this solution was added dropwise to a suspension of 0.05 g of lithium aluminum hydride in 5 ml of tetrahydrofuran under ice-cooling. After completion of dropwise addition, the mixture was stirred at room temperature for 2 hours. Thereafter, the reaction mixture was worked up in the same manner as Example 93 to recover 0.07 g of 20-(1,3-dioxolan-2-yl)pregn-6-ene-1α,3β,5α-triol showing the same physical properties as the compound obtained in Example 94.

EXAMPLE 100

In 5 ml of tetrahydrofuran was dissolved 0.1 g of 20-(5,5-dimethyl-1,3-dioxan-2-yl)-1α,2α;4α,5α-diepoxy-3β-(N,N-dimethylcarbamoyl)oxypregn-6-ene and the solution was added dropwise to a suspension of 0.05 g of lithium aluminum hydride in 5 ml of tetrahydrofuran under ice-cooling. After completion of dropwise addition, the mixture was stirred at room temperature for 2 hours. Thereafter, the reaction mixture was worked up in the same manner as Example 93 to recover 0.06 g of 20-(5,5-dimethyl-1,3-dioxan-2-yl)pregn-6-ene-1α,3β,5α-triol showing the same physical properties as the compound obtained in Example 93.

EXAMPLE 101

In 5 ml of tetrahydrofuran was dissolved 0.1 g of 1α,2α;4α,5α-diepoxy-21,21-dimethoxy-20-methyl-3β-(N-phenylcarbamoyl)oxypregn-6-ene and the solution was added dropwise to a suspension of 0.05 g of lithium aluminum hydride in 5 ml of tetrahydrofuran under ice-cooling. After completion of dropwise addition, the mixture was stirred at room temperature for 2 hours. Thereafter, the reaction mixture was worked up in the same manner as Example 93 to give 0.07 g of 21,21-dimethoxy-20-methylpregn-6-ene-1α,3β,5α-triol showing the same physical properties as the compound obtained in Example 95.

EXAMPLE 102

In 5 ml of tetrahydrofuran was dissolved 0.1 g of 3β-benzoyloxy-1α,2α;4α,5α-diepoxy-21,21-dimethoxy-20-methylpregn-6-ene and the solution was added dropwise to a suspension of 0.05 g of lithium aluminum hydride in 5 ml of tetrahydrofuran under ice-cooling. After completion of dropwise addition, the mixture was stirred at room temperature for 2 hours. Thereafter, the reaction mixture was worked up in the same manner as Example 93 to recover 0.07 g of 21,21-dimethoxy-20- methylpregn-6-ene-1α,3β,5α-triol showing the same physical properties as the compound obtained in Example 95.

EXAMPLE 103

In 9 ml of methylene chloride was suspended 400 mg of 20-(5,5-dimethyl-1,3-dioxan-2-yl)pregn-6-ene-1α,3β,5α-triol, followed by addition of 2.2 ml of pyridine and a catalytic amount of N,N-dimethyl-4-aminopyridine. To this mixture was slowly added 0.75 ml of methyl chlorocarbonate dropwise under ice-cooling and the mixture was stirred at room temperature for 45 minutes. The resulting reaction mixture was poured in cold diluted hydrochloric acid and extracted with methylene chloride. The extracts were pooled, washed with aqueous sodium hydrogen carbonate solution and aqueous sodium chloride solution, and dried over magnesium sulfate, followed by concentration under reduced pressure. Finally the concentrate was purified by silica gel chromatography to recover 486 mg of 20-(5,5-dimethyl-1,3-dioxan-2-yl)-3β-(methoxycarbonyl)oxypregn-6-ene-1α,5α-diol showing the following physical properties.

$^1$H-NMR spectrum (90 MHz) $\delta_{TMS}^{CDCl_3}$: 0.70 (s, 6 H), 0.88 (s, 3 H), 1.05 (d, J=6.2 Hz, 3 H), 1.18 (s, 3 H), 3.34 (d, J=10.5 Hz, 1 H), 3.44 (d, J=10.5 Hz, 1 H), 3.57 (d, J=10.5 Hz, 2 H), 3.77 (s, 3 H), 4.10 (1 H), 4.38 (d, J=2.4 Hz, 1 H), 5.33 (m, 1 H), 5.51 (d, J=9.8 Hz, 1 H), 5.91 (d, J=9.8 Hz, 1 H).

IR spectrum (KBr): 3250, 1750 cm$^{-1}$.

EXAMPLE 104

In 5 ml of pyridine was dissolved 400 mg of 20-(1,3-dioxolan-2-yl)pregn-6-ene-1α,3β,5α-triol. To this solution was added 0.11 ml of acetic anhydride at a temperature of −10°-0° C. and the mixture was stirred under ice-cooling for 2 hours. The reaction mixture thus obtained was poured in ice-water and stirred at room temperature for 30 minutes. This mixture was then extracted with ether and the extracts were pooled, washed successively with water, cold diluted hydrochloric acid, water, aqueous sodium hydrogen carbonate solution and aqueous sodium chloride solution and dried over magnesium sulfate, followed by concentration under reduced pressure. Finally the concentrate was purified by silica gel chromatography to give 420 mg of 20-(1,3-dioxolan-2-yl)-3β-acetoxypregn-6-ene-1α,5α-diol showing the following properties.

$^1$H-NMR spectrum (90 MHz) $\delta_{TMS}^{CDCl_3}$: 0.72 (s, 3 H), 0.88 (s, 3 H), 0.95 (d, J=6.2 Hz, 3 H), 2.05 (s, 3 H), 3.70-4.05 (m, 4 H), 4.10 (1 H), 4.79 (br. s, 1 H), 5.23 (m, 1 H), 5.51 (d, J=9.8 Hz, 1 H), 5.91 (d, J=9.8 Hz, 1H).

IR spectrum (KBr): 3240, 1730 cm$^{-1}$.

EXAMPLE 105

In methylene chloride was suspended 400 mg of 21,21-dimethoxy-20-methylpregn-6-ene-1α,3β,5α-triol, followed by addition of 2 ml of pyridine. To this suspension was added 0.14 ml of benzoyl chloride and the mixture was stirred for 2 hours. Thereafter, the reaction mixture was worked up in the same manner as Example 103 to recover 430 mg of 3β-benzoyloxy-21,21-dimethoxy-20-methylpregn-6-ene-1α,5α-diol showing the following physical properties.

$^1$H-NMR spectrum (90 MHz) $\delta_{TMS}^{CDCl_3}$: 0.72 (s, 3 H), 0.88 (s, 3 H), 0.95 (d, J=6.2 Hz, 3 H), 3.38 (s, 3 H), 3.40 (s, 3 H), 4.10 (1 H), 4.38 (br. s, 1 H), 5.30 (m, 1 H), 5.51 (d, J=9.8 Hz, 1 H), 5.91 (d, J=9.8 Hz, 1 H), 7.2-7.7 (m, 3 H), 7.9-8.2 (m, 2 H).

IR spectrum (KBr): 3240, 1720 cm$^{-1}$.

EXAMPLE 106

In 20 ml of toluene was suspended 400 mg of 20-(5,5-dimethyl-1,3-dioxan-2-yl)pregn-6-ene-1α,3β,5α-triol, followed by addition of one drop of pyridine. To this suspension was added 0.8 ml of methyl isocyanate under ice-cooling and the mixture was stirred at 60° C. for 45 minutes. The reaction mixture thus obtained was poured in ice-water and extracted with methylene chloride. The extracts were pooled, washed with water and aqueous sodium chloride solution, and dried over sodium sulfate, followed by concentration under reduced pressure. Finally the concentrate was purified by silica gel chromatography to recover 486 mg of 20-(5,5-dimethyl-1,3-dioxan-2-yl)-3β-(N-methylcarbamoyl)oxypregn-6-ene-1α,5α-diol showing the following physical properties.

$^1$H-NMR spectrum (90 MHz) $\delta_{TMS}^{CDCl_3}$: 0.70 (s, 6 H), 0.88 (s, 3 H), 1.05 (d, J=6.2 Hz, 3 H), 1.18 (s, 3 H), 2.76 (d, J=6 Hz, 3 H), 3.34 (d, J=10.5 Hz, 1 H), 3.44 (d, J=10.5 Hz, 1 H), 3.57 (d, J=10.5 Hz, 2 H), 4.10 (1 H), 4.38 (d, J=2.4 Hz, 1 H), 5.20 (1 H), 5.33 (m, 1 H), 5.51 (d, J=9.8 Hz, 1 H), 5.91 (d, J=9.8 Hz, 1 H).

IR spectrum (KBr): 3250, 1710 cm$^{-1}$.

EXAMPLE 107

In 20 ml of toluene was suspended 400 mg of 20-(5,5-dimethyl-1,3-dioxan-2-yl)pregn-6-ene-1α,3β,5α-triol, followed by addition of one drop of pyridine. To this suspension was added 0.8 ml of phenyl isocyanate under ice-cooling and the mixture was stirred at 60° C. for 45 minutes. The reaction mixture thus obtained was poured in ice-water and extracted with methylene chloride. The extracts were pooled, washed with water and aqueous sodium chloride solution, and dried over sodium sulfate, followed by concentration under reduced pressure. Finally the concentrate was purified by silica gel chromatography to recover 412 mg of 20-(5,5-dimethyl-1,3-dioxan-2-yl)-3β-(N-phenylcarbamoyl)oxypregn-6-ene-1α,5α-diol showing the following physical properties.

$^1$H-NMR spectrum (90 MHz) $\delta_{TMS}^{CDCl_3}$: 0.70 (s, 6 H), 0.88 (s, 3 H), 1.05 (d, J=6.2 Hz, 3 H), 1.18 (s, 3 H), 3.34 (d, J=10.5 Hz, 1 H), 3.44 (d, J=10.5 Hz, 1 H), 3.57 (d, J=10.5 Hz, 2 H), 4.10 (1 H), 4.38 (d, J=2.4 Hz, 1 H), 5.30 (m, 1 H), 5.49 (d, J=9.8 Hz, 1 H), 5.90 (d, J=9.8 Hz, 1 H), 6.80 (br. s, 1 H), 7.1-7.7 (5 H).

IR spectrum (KBr): 3350, 1720 cm$^{-1}$.

EXAMPLE 108

In 20 ml of toluene was suspended 400 mg of 20-(5,5-dimethyl-1,3-dioxan-2-yl)pregn-6-ene-1α,3β,5α-triol, followed by addition of 5 ml of pyridine and 0.1 g of N,N-dimethyl-4-aminopyridine. To this suspension was added 0.8 ml of N,N-dimethylcarbamoyl chloride under ice-cooling and the mixture was stirred at 60° C. for 10 hours. The reaction mixture thus obtained was poured in cold diluted hydrochloric acid and extracted with methylene chloride. The extracts were pooled, washed with aqueous sodium hydrogen carbonate solution and aqueous sodium chloride solution, and dried over sodium sulfate, followed by concentration under reduced pressure. Finally the concentrate was purified by silica gel chromatography to recover 435 mg of 20-(5,5-dimethyl-1,3-dioxan-2-yl)-3β-(N,N-dimethylcarbamoyl)oxypregn-6-ene-1α,5α-diol showing the following physical properties.

$^1$H-NMR spectrum (90 MHz) $\delta_{TMS}^{CDCl_3}$: 0.70 (s, 6 H), 0.88 (s, 3 H), 1.05 (d, J=6.2 Hz, 3 H), 1.18 (s, 3 H), 2.78 & 2.81 (each s, 6 H), 3.34 (d, J=10.5 Hz, 1 H), 3.44 (d, J=10.5 Hz, 1 H), 3.57 (d, J=10.5 Hz, 2 H), 4.10 (1 H), 4.38 (d, J=2.4 Hz, 1 H), 5.34 (m, 1 H), 5.50 (d, J=9.8 Hz, 1 H), 5.89 (d, J=9.8 Hz, 1 H).

IR spectrum (KBr): 3300, 1695 cm$^{-1}$.

EXAMPLE 109

In 20 ml of N,N-dimethylformamide was dissolved 400 mg of 20-(5,5-dimethyl-1,3-dioxan-2-yl)pregn-6-ene-3β,5α-triol, followed by addition of 0.6 g of imidazole. Then, 0.7 g of tert-butyldimethylsilyl chloride was further added under ice-cooling and the mixture was stirred at room temperature for 10 hours. The reaction mixture thus obtained was poured in water and extracted with ether. The extracts were pooled, washed with water and aqueous sodium chloride solution, and dried over sodium sulfate, followed by concentration under reduced pressure. Finally the concentrate was purified by silica gel chromatography to recover 490 mg of 20-(5,5-dimethyl-1,3-dioxan-2-yl)-3β-(tert-butyldimethylsilyl)oxypregn-6-ene-1α,5α-diol showing the following physical properties.

$^1$H-NMR spectrum (90 MHz) $\delta_{TMS}^{CDCl_3}$: 0.13 (s, 6 H), 0.70 (s, 6 H), 0.88 (s, 3 H), 0.95 (s, 9 H), 1.05 (d, J=6.2 Hz, 3 H), 1.18 (s, 3 H), 3.34 (d, J=10.5 Hz, 1 H), 3.44 (d, J=10.5 Hz, 1 H), 3.57 (d, J=10.5 Hz, 2 H), 4.10–4.50 (2 H), 4.38 (d, J=2.4 Hz, 1 H), 5.50 (d, J=9.8 Hz, 1 H), 5.89 (d, J=9.8 Hz, 1 H).

IR spectrum (KBr): 3350 cm$^{-1}$.

EXAMPLE 110

In 5 ml of tetrahydrofuran was dissolved 20-(1,3-dioxolan-2-yl)pregn-6-ene-1α,3β,5α-triol. This solution was added to a suspension of 60 mg of 60% sodium hydride in 5 ml of tetrahydrofuran under ice-cooling and the mixture was stirred at room temperature for 1 hour. To the resulting mixture was added 120 mg of chloromethyl methyl ether, followed by stirring at a temperature of 60° C. for 2 hours. The reaction mixture was poured in ice-water and extracted with ether. The extracts were pooled, washed with aqueous sodium hydrogen carbonate solution and aqueous sodium chloride solution, and dried over sodium sulfate, followed by concentration under reduced pressure. Finally the concentrate was purified by silica gel chromatography to recover 420 mg of 20-(1,3-dioxolan-2-yl)-3β-(methoxymethyl)oxypregn-6-ene-1α,5α-diol showing the following physical properties.

$^1$H-NMR spectrum (90 MHz) $\delta_{TMS}^{CDCl_3}$: 0.72 (s, 3 H), 0.88 (s, 3 H), 0.95 (d, J=6.2 Hz, 3 H), 3.34 (s, 3 H), 3.70–4.05 (m, 4 H), 4.10 (1 H), 4.40 (m, 1 H), 4.79 (br. s, 2 H), 5.51 (d, J=9.8 Hz, 1 H), 5.91 (d, J=9.8 Hz, 1 H).

IR spectrum (KBr): 3240 cm$^{-1}$.

EXAMPLE 111

The reaction and workup procedures of Example 109 were repeated except that 400 mg of 21,21-dimethoxy-20-methylpregn-6-ene-1α,3β,5α-triol was used in lieu of 400 mg of 20-(5,5-dimethyl-1,3-dioxan-2-yl)pregn-6-ene-1α,3β,5α-triol to give 500 mg of 3β-tert-butyldimethylsilyloxy-21,21-dimethoxy-20-methylpregn-6-ene-1α,5α-diol.

$^1$H-NMR spectrum (90 MHz) $\delta_{TMS}^{CDCl_3}$: 0.12 (s, 6 H), 0.72 (s, 3 H), 0.88 (s, 3 H), 0.93 (s, 9 H), 0.95 (d, J=6.2 Hz, 3 H), 3.38 (s, 3 H), 3.40 (s, 3 H), 4.10–4.50 (3 H), 5.51 (d, J=9.8 Hz, 1 H), 5.91 (d, J=9.8 Hz, 1 H).

IR spectrum (KBr): 3240 cm$^{-1}$.

EXAMPLE 112

In 5 ml of tetrahydrofuran was dissolved 100 mg of 20-(5,5-dimethyl-1,3-dioxan-2-yl)-1α,2α;4α,5α-diepoxy-3β-(tert-butyldimethylsilyl)oxypregn-6-ene and the solution was added dropwise to a suspension of 50 mg of lithium aluminum hydride in 5 ml of tetrahydrofuran under ice-cooling. This mixture was stirred at room temperature for 2 hours. Thereafter, the reaction mixture was worked up in the same manner as Example 93 to recover 49 mg of 20-(5,5-dimethyl-1,3-dioxan-2-yl)-3β-(tert-butyldimethylsilyl)oxypregn-6-ene-1α,5α-diol which showed the same physical properties as the compound obtained in example 109.

EXAMPLE 113

In 5 ml of tetrahydrofuran was dissolved 100 mg of 20-(1,3-dioxolan-2-yl)-1α,2α;4α,5α-diepoxy-3β-(methoxymethyl)oxypregn-6-ene, followed by addition of 0.2 ml of a 3.4M solution of sodium bis(2-methoxyethoxy)aluminum hydride in toluene under ice-cooling. The mixture was stirred at room temperature for 2 hours. Thereafter, the reaction mixture was worked up in the same manner as Example 94 to recover 42 mg of 20-(1,3-dioxolan-2-yl)-3β-(methoxymethyl)oxypregn-6-ene-1α,5α-diol showing the same physical properties as the compound obtained in Example 110.

EXAMPLE 114

The reaction and workup procedures of Example 112 were repeated except that 100 mg of 1α,2α;4α,5α-diepoxy-21,21-dimethoxy-20-methyl-3β-(tert-butyldimethylsilyl)oxypregn-6-ene was used in lieu of 100 mg of 20-(5,5-dimethyl-1,3-dioxan-2-yl)-1α,2α;4α,5α-diepoxy-3β-(tertbutyldimethylsilyl)oxypregn-6-ene to give 50 mg of 3β-tert-butyldimethylsilyloxy-21,21-dimethoxy-20-methylpregn-6-ene-1α,5α-diol showing the same physical properties as the compound obtained in Example 111.

EXAMPLE 115

In 5 ml of methylene chloride was dissolved 262 mg of 20-(5,5-dimethyl-1,3-dioxan-2-yl)-3β-(methoxycarbonyloxy)pregn-6-ene-1α,5α-diol, followed by addition of 1.7 ml of diisopropylethylamine and a catalytic amount of 4-(N,N-dimethylamino)pyridine. The mixture was stirred under ice-cooling. To this mixture was slowly added 0.19 ml of methyl chlorocarbonate and the mixture was stirred at room temperature for 2.5 hours. The reaction mixture thus obtained was poured in ice-water and extracted with ether. The extracts were pooled, washed successively with water, aqueous sodium hydrogen carbonate solution and aqueous sodium chloride solution, and dried over magnesium sulfate, followed by concentration under reduced pressure. Finally the concentrate was purified by column chromatography to recover 243 mg of 20-(5,5-dimethyl-1,3-dioxan-2-yl)-1α,3β-bis(methoxycarbonyloxy)pregn-6-en-5α-ol showing the following physical properties.

$^1$H-NMR spectrum (90 MHz) $\delta_{TMS}^{CDCl_3}$: 0.70 (s, 6 H), 0.99 (s, 3 H), 1.05 (d, J=6.2 Hz, 3 H), 1.16 (s, 3 H), 3.33 (d, J=11.4 Hz, 1 H), 3.43 (d, J=11.4 Hz, 1 H), 3.59 (d, J=11.4 Hz, 2 H), 3.77 & 3.78 (each s, 6 H), 4.37 (br. s, 1 H), 4.85 (t, J=3 Hz, 1 H), 5.53 (m, 1 H), 5.58 (br. s, 2 H).

IR spectrum (KBr): 3320, 1750 cm$^{-1}$.

EXAMPLE 116

The reaction and workup procedures of Example 105 were repeated except that 350 mg of 20-(1,3-dioxolan-2-yl)-3β-acetoxypregn-6-ene-1α,5α-diol was used in lieu of 400 mg of 21,21-dimethoxy-20-methylpregn-6-ene-3β,5α-triol to give 400 mg of 20-(1,3-dioxolan-2-yl)-3β-acetoxy-1α-benzoyloxypregn-6-en-5α-ol showing the following physical properties.

$^1$H-NMR spectrum (90 MHz) $\delta_{TMS}^{CDCl_3}$: 0.72 (s, 3 H), 0.95 (d, J=6.2 Hz, 3 H), 1.00 (s, 3 H), 2.05 (s, 3 H), 3.70–4.05 (m, 4 H), 4.79 (br. s, 1 H), 4.95 (1 H), 5.23 (m, 1 H), 5.60 (br. s, 2 H), 7.2–7.7 (3 H), 7.9–8.2 (2 H).

IR spectrum (KBr): 3320, 1735, 1720 cm$^{-1}$.

EXAMPLE 117

The reaction and workup procedures of Example 106 were repeated except that 350 mg of 3β-benzoyloxy-21,21-dimethoxy-20-methylpregn-6-ene-1α,5α-diol was used in lieu of 400 mg of 20-(5,5-dimethyl-1,3-dioxan-2-yl)pregn-6-ene-1α,3β,5α-triol to give 380 mg of 3β-benzoyloxy-21,21-dimethoxy-20-methyl-1α-(N-methylcarbamoyl)oxypregn-6-ene-1α,5α-diol showing the following physical properties.

$^1$H-NMR spectrum (90 MHz) $\delta_{TMS}^{CDCl_3}$: 0.72 (s, 3 H), 0.95 (d, J=6.2 Hz, 3 H), 1.02 (s, 3 H), 2.80 (d, J=6 Hz, 3 H), 3.38 (s, 3 H), 3.40 (s, 3 H), 4.38 (br. s, 1 H), 4.95 (1 H), 5.15 (1 H), 5.30(m, 1H), 5.61(br. s, 2H), 7.2–7.7 (m, 3 H), 7.9–8.2 (m, 2 H).

IR spectrum (KBr): 3240, 1720, 1710 cm$^{-1}$.

EXAMPLE 118

The reaction and workup procedures of Example 107 were repeated except that 350 mg of 20-(5,5-dimethyl-1,3-dioxan-2-yl)-3β-(N-methylcarbamoyl)oxypregna-1α,5α-diol was used in lieu of 400 mg of 20-(5,5-dimethyl-1,3-dioxan-2-yl)pregn-6-ene-1α,3β,5α-triol to give 355 mg of 20-(5,5-dimethyl-1,3-dioxan-2-yl)-3β-(N-methylcarbamoyl)oxy-1α-(N-phenylcarbamoyl)oxypregn-6-en-5α-ol showing the following physical properties.

$^1$H-NMR spectrum (90 MHz) $\delta_{TMS}^{CDCl_3}$: 0.70 (s, 6 H), 0.99 (s, 3 H), 1.05 (d, J=6.2 Hz, 3 H), 1.18 (s, 3 H), 2.76 (d, J=6 Hz, 3 H), 3.34 (d, J=10.5 Hz, 1 H), 3.44 (d, J=10.5 Hz, 1 H), 3.57 (d, J=10.5 Hz, 2 H), 4.38 (d, J=2.4 Hz, 1 H), 5.01 (1 H), 5.20 (1 H), 5.33 (m, 1 H), 5.70 (br. s, 2 H), 6.75 (br. s, 1 H), 7.1–7.7 (5 H).

IR spectrum (KBr): 3250, 1720, 1710cm$^{-1}$.

EXAMPLE 119

The reaction and workup procedures of Example 108 were repeated except that 350 mg of 20-(5,5-dimethyl-1,3-dioxan-2-yl)-3β-(N-phenylcarbamoyl)oxypregn-6-ene-1α,2α-diol was used in lieu of 400 mg of 20-(5,5-dimethyl-1,3-dioxan-2-yl)pregn-6-ene-1α,3β,5α-triol to give 340 mg of 20-(5,5-dimethyl-1,3-dioxan-2-yl)-1α-(N,N-dimethylcarbamoyl)oxy-3β-(N-phenylcarbamoyl)oxypregn-6-en-5α-ol showing the following physical properties.

$^1$H-NMR spectrum (90 MHz) $\delta_{TMS}^{CDCl_3}$: 0.70 (s, 6 H), 0.99 (s, 3 H), 1.05 (d, J=6.2 Hz, 3 H), 1.18 (s, 3 H), 2.78 & 2.81 (each s, 6 H), 3.34 (d, J=10.5 Hz, 1 H), 3.44 (d, J=10.5 Hz, 1 H), 3.57 (d, J=10.5 Hz, 2 H), 4.38 (d, J=2.4 Hz, 1 H), 5.00 (1 H), 5.30 (m, 1 H), 5.68 (br. s, 2 H), 6.80 (br. s, 1 H), 7.1–7.7 (5 H).

IR spectrum (KBr): 3350, 1720, 1690 cm$^{-1}$.

EXAMPLE 120

The reaction and workup procedures of Example 109 were repeated except that 350 mg of 20(5,5-dimethyl-1,3-dioxan-2-yl)-3β-(N,N-dimethylcarbamoyl)oxypregn-6-ene-1α,5α-diol was used in lieu of 400 mg of 20-(5,5-dimethyl-1,3-dioxan-2-yl)pregn-6-ene-1α,3β,5α-triol to give 335 mg of 20-(5,5-dimethyl-1,3-dioxan-2-yl)-1α-(tert-butyldimethylsilyl)oxy-3β-(N,N-dimethylcarbamoyl)oxypregn-6-en-5α-ol showing the following physical properties.

$^1$H-NMR spectrum (90 MHz) $\delta_{TMS}^{CDCl_3}$: 0.15 (s, 6 H), 0.70 (s, 6 H), 0.93 (s, 3 H), 0.97 (s, 9 H), 1.05 (d, J=6.2 Hz, 3 H), 1.18 (s, 3 H), 2.78 & 2.81 (each s, 6 H), 3.34 (d, J=10.5 Hz, 1 H), 3.44 (d, J=10.5 Hz, 1 H), 3.57 (d, J=10.5 Hz, 2 H), 4.2–4.5 (2 H), 5.34 (m, 1 H), 5.65 (br. s, 2 H).

IR spectrum (KBr): 3320, 1695 cm$^{-1}$.

EXAMPLE 121

The reaction and workup procedures of Example 110 were repeated except that 400 mg of 20-(5,5-dimethyl-1,3-dioxan-2-yl)-3β-(tert-butyldimethylsilyl)oxypregn-6-ene-1α,5α-diol was used in lieu of 400 mg of 20-(1,3-dioxolan-2-yl)pregn-6-ene-1α,3β,5α-triol to give 320 mg of 20-(5,5-dimethyl-1,3-dioxan-2-yl)-3β-(tertbutyldimethylsilyl)oxy-1α-(methoxymethyl)oxypregn-6-en-5α-ol showing the following physical properties.

$^1$H-NMR spectrum (90 MHz) $\delta_{TMS}^{CDCl_3}$: 0.13 (s, 6 H), 0.70 (s, 6 H), 0.95 (s, 9 H), 0.99 (s, 3 H), 1.05 (d, J=6.2 Hz, 3 H), 1.18 (s, 3 H), 3.34 (d, J=10.5 Hz, 1 H), 3.36 (s, 3 H), 3.44 (d, J=10.5 Hz, 1 H), 3.57 (d, J=10.5 Hz, 2 H), 4.10–4.50 (2 H), 4.38 (d, J=2.4 Hz, 1 H), 4.80 (br. s, 2H), 5.65 (br. s, 2H).

IR spectrum (KBr): 3350 cm$^{-1}$.

EXAMPLE 122

The reaction and workup procedures of Example 104 were repeated except that 350 mg of 20-(1,3-dioxolan-2-yl)-3β-(methoxymethyl)oxypregn-6-ene-1α,5α-diol was used in lieu of 400 mg of 20-(1,3-dioxolan-2-yl)pregn-6-ene-1α,3β,5α-triol to give 360 mg of 20-(1,3-dioxolan-2yl)-1α-acetoxy-3β-(methoxymethyl)oxypregn-6-ene-1α,5α-diol showing the following physical properties.

$^1$H-NMR spectrum (90 MHz) $\delta_{TMS}^{CDCl_3}$: 0.72 (s, 3 H), 0.95 (d, J=6.2 Hz, 3 H), 0.98 (s, 3 H), 2.07 (s, 3 H), 3.70–4.05 (m, 4 H), 4.40 (m, 1 H), 4.79 (br. s, 1 H), 4.99 (1 H), 5.70 (br. s, 2 H).

IR spectrum (KBr): 3240, 1735 cm$^{-1}$.

EXAMPLE 123

In 5 ml of pyridine was dissolved 400 mg of 20-(5,5-dimethyl-1,3-dioxan-2-yl)pregn-6-ene-1α,3β,5α-triol, followed by addition of 50 mg of 4-(N,N-dimethylamino)pyridine and 1 ml of acetic anhydride. The mixture was stirred at room temperature for 2 hours. The reaction mixture was then worked up in the same manner as Example 104 to give 420 mg of 20-(5,5-dimethyl-1,3-dioxan-2-yl)-1α,3β-diacetoxypregn-6-en-5α-ol showing the following physical properties.

$^1$H-NMR spectrum (90 MHz) $\delta_{TMS}^{CDCl_3}$: 0.70 (s, 6 H), 0.99 (s, 3 H), 1.05 (d, J=6.2 Hz, 3 H), 1.16 (s, 3 H), 2.03 & 2.07 (each s, 6 H), 3.33 (d, J=11.4 Hz, 1 H), 3.43 (d, J=11.4 Hz, 1 H), 3.59 (d, J=11.4 Hz, 2 H), 4.37 (br. s, 1 H), 4.85 (t, J=3 Hz, 1 H), 5.53 (m, 1 H), 5.58 (br. s, 2 H).

IR spectrum (KBr): 3320, 1735 cm$^{-1}$.

EXAMPLE 124

In 10 ml of dimethyl carbonate was dissolved 345 mg of 20-(5,5-dimethyl-1,3-dioxan-2-yl)-1α,3β-bis(methoxycarbonyloxy)pregn-6-en-5α-ol, followed by addition of 0.2 ml of acetic acid. The mixture was refluxed in an atmosphere of argon gas for 10 hours. The reaction mixture was poured in ice-water and extracted with ether. The extracts were pooled, neutralized with cold aqueous sodium hydroxide solution and aqueous sodium hydrogen carbonate solution, and washed with aqueous sodium chloride solution, followed by concentration under reduced pressure. Finally the concentrate was purified by column chromatography to recover 40 mg of 20-(5,5-dimethyl-1,3-dioxan-2-yl)-1α,3β-bis(methoxycarbonyloxy)pregna-5,7-diene showing the following physical properties.

$^1$H-NMR spectrum (90 MHz) $\delta_{TMS}^{CDCl_3}$: 0.61 (s, 3 H), 0.70 (s, 3 H), 1.00 (s, 3 H), 1.07 (d, J=6.2 Hz, 3 H), 1.17 (s, 3 H), 3.25 (d, J=10.8 Hz, 1 H), 3.42 (d, J=10.8 Hz, 1 H), 3.60 (d, J=10.8 Hz, 2 H), 3.77 & 3.79 (each s, 6 H), 4.39 (br. s, 1 H), 4.62-5.12 (2 H), 5.36 (m, 1 H), 5.68 (m, 1 H).

IR spectrum (KBr): 1740 cm$^{-1}$.

EXAMPLE 125

In 10 ml of diethyl carbonate was dissolved 350 mg of 20-(1,3-dioxolan-2-yl)-3β-acetoxy-1α-benzoyloxypregn-6-en-5α-ol, followed by addition of 0.1 ml of monochloroacetic acid. The mixture was stirred under heating at 100° C. in an atmosphere of argon gas for 10 hours. The reaction mixture was then worked up in the same manner as Example 124 to give 120 mg of 20-(1,3-dioxolan-2yl)-3β-acetoxy-1α-benzoyloxypregna-5,7-diene showing the following physical properties.

$^1$H-NMR spectrum (90 MHz) $\delta_{TMS}^{CDCl_3}$: 0.65 (s, 3 H), 0.95 (d, J=6.2 Hz, 3 H), 1.00 (s, 3 H), 2.05 (s, 3 H), 3.70-4.05 (m, 4 H), 4.79 (br. s, 1 H), 4.70-5.10 (2 H), 5.38 (m, 1 H), 5.70 (m, 1 H), 7.2-7.7 (3 H), 7.9-8.2 (2 H).

IR spectrum (KBr): 1735, 1720 cm$^{-1}$.

EXAMPLE 126

In 10 ml of tetrahydrofuran was dissolved 350 mg of 3β-benzoyloxy-21,21-dimethoxy-20-methyl-1α-(N-methylcarbamoyl)oxypregn-6-en-5α-ol, followed by addition of 50 mg of dichloroacetic acid. The mixture was refluxed in an atmosphere of argon gas for 12 hours. The reaction mixture was then worked up in the same manner as Example 124 to give 120 mg of 3β-benzoyloxy-21,21-dimethoxy-20-methyl-1α-(N-methylcarbamoyl)oxypregna-5,7-diene showing the following physical properties.

$^1$H-NMR spectrum (90 MHz) $\delta_{TMS}^{CDCl_3}$: 0.64 (s, 3 H), 0.95 (d, J=6.2 Hz, 3H), 1.02 (s, 3 H), 2.80 (d, J=6 Hz, 3 H), 3.38 (s, 3 H), 3.40 (s, 3 H), 4.38 (br. s, 1 H), 4.95 (1 H), 4.7-5.1 (2 H), 5.36 (m, 1 H), 5.68 (m, 1 H), 7.2-7.7 (m, 3 H), 7.9-8.2 (m, 2H).

IR spectrum (KBr): 1720, 1710 cm$^{-1}$.

EXAMPLE 127

In 10 ml of dioxane was dissolved 350 mg of 20-(5,5-dimethyl-1,3-dioxan-2-yl)-1α-(N-phenylcarbamoyl)oxy-3β-(N-methylcarbamoyl)-oxypregn-5α-ol, followed by addition of 50 mg of p-toluenesulfonic acid. The mixture was stirred in an atmosphere of argon gas at room temperature for 3 hours. The reaction mixture was then worked up in the same manner as Example 124 to methylcarbamoyl)oxy-1α-(N-phenylcarbamoyl)oxypregna-5,7-diene showing the following physical properties.

$^1$H-NMR spectrum (90 MHz) $\delta_{TMS}^{CDCl_3}$: 0.65 (s, 3 H), 0.70 (s, 3 H), 0.99 (s, 3 H), 1.05 (d, J=6.2 Hz, 3 H), 1.18 (s, 3 H), 2.76 (d, J=6 Hz, 3 H), 3.34 (d, J=10.5 Hz, 1 H), 3.44 (d, J=10.5 Hz, 1 H), 3.57 (d, J=10.5 Hz, 2 H), 4.38 (d, J=2.4 Hz, 1 H), 4.65-5.15 (2 H), 5.20 (1 H), 5.36 (m, 1 H), 5.68 (m, 1 H), 6.75 (br. s, 1 H), 7.1-7.7 (5 H).

IR spectrum (KBr): 1720, 1710 cm$^{-1}$.

EXAMPLE 128

In 10 ml of toluene was dissolved 350 mg of 20-(5,5-dimethyl-1,3-dioxan-2-yl)-1α-(N,N-dimethylcarbamoyl)oxy-3β-(N-phenylcarbamoyl)oxypregn-6-en-5α-ol, followed by addition of 50 mg of pyridinium p-toluenesulfonate. The mixture was stirred in an atmosphere of argon gas at room temperature for 10 hours. The reaction mixture was then worked up in the same manner as Example 124 to give 100 mg of 20-(5,5-dimethyl-1,3-dioxan-2-yl)-1α-(N,N-dimethylcarbamoyl)oxy-3β-(N-phenylcarbamoyl)oxypregna-5,7-diene showing the following physical properties.

$^1$H-NMR spectrum (90 MHz) $\delta_{TMS}^{CDCl_3}$: 0.61 (s, 3 H), 0.70 (s, 3 H), 0.99 (s, 3 H), 1.05 (d, J=6.2 Hz, 3 H), 1.18 (s, 3 H), 2.78 & 2.81 (each s, 6 H), 3.34 (d, J=10.5 Hz, 1 H), 3.44 (d, J=10.5 Hz, 1 H), 3.57 (d, J=10.5 Hz, 2 H), 4.38 (d, J=2.4 Hz, 1 H), 4.65-5.15 (2 H), 5.36 (m, 1 H), 5.70 (m, 1 H), 6.80 (br. s, 1 H), 7.1-7.7 (5 H).

IR spectrum (KBr): 1720, 1695 cm$^{-1}$.

EXAMPLE 129

In 10 ml of benzene was dissolved 350 mg of 20-(5,5-dimethyl-1,3-dioxan-2-yl)-1α-(tert-butyldimethylsilyl)oxy-3β-(N,N-dimethylcarbamoyl)oxypregn-6-en-5α-ol, followed by addition of one drop of concentrated sulfuric acid. The mixture was stirred in an atmosphere of argon gas under ice-cooling for 1 hour. The reaction mixture was then worked up in the same manner as Example 124 to give 135 mg of 20-(5,5-dimethyl-1,3-dioxan-2-yl)-1α-(tert-butyldimethylsilyl)oxy-3β-(N,N-dimethylcarbamoyl)oxypregna-5,7-diene showing the following properties.

$^1$H-NMR spectrum (90 MHz $\delta_{TMS}^{CDCl_3}$: 0.15 (s, 6 H), 0.61 (s, 3 H), 0.70 (s, 3 H), 0.93 (s, 3 H), 0.97 (s, 9 H), 1.05 (d, J=6.2 Hz, 3 H), 1.18 (s, 3 H) 2.78 & 2.81 (each s, 6 H), 3.34 (d, J=10.5 Hz, 1 H), 3.44 (d, J=10.5 Hz, 1 H), 3.57 (d, J=10.5 Hz, 2 H), 4.2-4.5 (2 H), 4.90 (m, 1 H), 5.38 (m, 1 H), 5.68 (m, 1 H).

IR spectrum (KBr): 1695 cm$^{-1}$.

EXAMPLE 130

In 10 ml of ethyl acetate was dissolved 400 mg of 20-(5,5-dimethyl-1,3-dioxan-2-yl)-3β-(tert-butyldimethylsilyl)oxy-1α-(methoxymethyl)oxypregn-6-en-5α-ol, followed by addition of 0.2 ml of acetic acid. The mixture was refluxed in an atmosphere of argon gas for 12 hours. The reaction mixture was then worked up in the same manner as Example 124 to give 150 mg of 20-(5,5-dimethyl-1,3-dioxan-2-yl)-3β-(tert-butyldimethylsilyl)oxy-1α-(methoxymethyl)oxypregna-5,7-diene showing the following physical properties.

$^1$H-NMR spectrum (90 MHz) $\delta_{TMS}^{CDCl_3}$: 0.13 (s, 6 H), 0.61 (s, 3 H), 0.70 (s, 3 H), 0.95 (s, 9 H), 0.99 (s, 3 H), 1.05 (d, J=6.2 Hz, 3 H), 1.18 (s, 3 H), 3.34 (d, J=10.5 Hz, 1 H), 3.36 (s, 3 H), 3.44 (d, J=10.5 Hz, 1 H), 3.57 (d, J=10.5 Hz, 2 H), 4.10-4.50 (2 H), 4.38 (d, J=2.4 Hz, 1 H), 4.80 (br. s, 2 H), 5.35 (m, 1 H), 5.70 (m, 1 H).

EXAMPLE 131

In 10 ml of butyl acetate was dissolved 350 mg of 20-(1,3-dioxolan-2-yl)-1α-acetoxy-3β-(methoxymethyl)oxypregn-6-en-5α-ol, followed by addition of 0.2 ml of acetic acid. The mixture was stirred in an atmosphere of argon gas under heating at 100° C. for 12 hours. The reaction mixture was then worked up in the same manner as Example 124 to give 100 mg of 20-(1,3-dioxolan-2-yl)-1α--acetoxy-3β-(methoxymethyl)oxypregna-5,7-diene showing the following physical properties.

$^1$H-NMR spectrum (90 MHz) $\delta_{TMS}^{CDCl3}$: 0.62 (s, 3 H), 0.95 (d, J=6.2 Hz, 3 H), 0.98 (s, 3 H), 2.07 (s, 3 H), 3.35 (s, 3 H), 3.70–4.05 (m, 4 H), 4.30 (m, 1 H), 4.65 (br. s, 2 H), 4.79 (br. s, 1 H), 4.99 (1 H), 5.35 (m, 1 H), 5.70 (m, 1 H).

IR spectrum (KBr): 1735 cm$^{-1}$.

EXAMPLE 132

In 10 ml of dimethyl carbonate was dissolved 345 mg of 20-(5,5-dimethyl-1,3-dioxan-2-yl)-1α,3β-bis(methoxycarbonyloxy)pregn-6-en-5α-ol, followed by addition of 0.2 ml of acetic acid. The mixture was refluxed in an atmosphere of argon gas for 10 hours. The reaction mixture was poured in ice-water and extracted with ether. The extracts were pooled, neutralized with cold aqueous sodium hydroxide solution and aqueous sodium hydrogen carbonate solution, and washed with aqueous sodium chloride solution. The solvent was distilled off under reduced pressure and the residue was purified by column chromatography to recover 140 mg of 20-(5,5-dimethyl-1,3-dioxan-2-yl)-1α,3β,7α-tris(methoxycarbonyloxy)pregn-5-ene showing the following physical properties.

$^1$H-NMR spectrum (90 MHz) $\delta_{TMS}^{CDCl3}$: 0.68 (s, 6 H), 1.05 (s, J=6.2 Hz, 3 H), 1.08 (s, 3 H), 1.16 (s, 3 H), 3.25 (d, J=10.8 Hz, 1 H), 3.42 (d, J=10.8 Hz, 1 H), 3.60 (d, J=10.8 Hz, 2 H), 3.77, 3.78 & 3.80 (each s, 9 H), 4.37 (br. s, 1 H), 4.72-5.12 (3 H), 5.90 (d, J=5.7 Hz, 1 H).

IR spectrum (KBr): 1745 cm$^{-1}$.

EXAMPLE 133

In 10 ml of dimethyl carbonate was dissolved 350 mg of 20-(1,3-dioxolan-2-yl)-3β-acetoxy-1α-benzoyloxy-pregn-6-en-5α-ol, followed by addition of 0.1 ml of monochloroacetic acid. The mixture was stirred in an atmosphere of argon gas under heating at a temperature of 100° C. for 10 hours. The reaction mixture was then worked up in the same manner as Example 132 to give 100 mg of 20-(1,3-dioxolan- 2-yl)-3β-acetoxy-1α-benzoyloxy-7α-(methoxycarbonyl)oxypregn-5-ene showing the following physical properties.

$^1$H-NMR spectrum (90 MHz) $\delta_{TMS}^{CDCl3}$: 0.72 (s, 3 H), 0.95 (d, J=6.2 Hz, 3 H), 1.08 (s, 3 H), 2.05 (s, 3 H), 3.70–4.05 (m, 4 H), 3.80 (s, 3 H), 4.79 (br. s, 1 H), 4.70–5.10 (3 H), 5.91 (d, J=5.8 Hz, 1 H), 7.2–7.7 (3 H), 7.9–8.2 (2 H).

IR spectrum (KBr): 1745, 1735, 1720 cm$^{-1}$.

EXAMPLE 134

In 10 ml of dimethyl carbonate was dissolved 350 mg of 3β-benzoyloxy-21,21-dimethoxy-20-methyl-1α-(N-methylcarbamoyl)oxypregn-6-en-5α-ol, followed by addition of 50 mg of dichloroacetic acid, and the mixture was heated in an atmosphere of argon gas for 12 hours. The reaction mixture was then worked up in the same manner as Example 132 to give 90 mg of 3β-benzoyloxy-21,21-dimethoxy-20-methyl-1α-(N-methylcarbamoyl)oxy-7α-(methoxycarbonyl)oxypregn-5-ene showing the following physical properties.

$^1$H-NMR spectrum (90 MHz) $\delta_{TMS}^{CDCl3}$: 0.74 (s, 3 H), 0.95 (d, J=6.2 Hz, 3 H), 1.08 (s, 3 H), 2.80 (d, J=6 Hz, 3 H), 3.38 (s, 3 H), 3.40 (s, 3 H), 3.77 (s, 3 H), 4.38 (br. s, 1 H), 4.95 (1 H), 4.7–5.1 (3 H), 5.88 (d, J=5.7 Hz, 1 H), 7.2–7.7 (m, 3 H), 7.9–8.2 (m, 2 H).

IR spectrum (KBr): 1750, 1720, 1710 cm$^{-1}$.

EXAMPLE 135

In 10 ml of dimethyl carbonate was dissolved 350 mg of 20-(5,5-dimethyl-1,3-dioxan-2-yl)-1α-(N-phenylcarbamoyl)oxy-3β-(N-methylcarbamoyl)oxypregn-5α-ol, followed by addition of 50 mg of p-toluenesulfonic acid. The mixture was stirred in an atmosphere of argon gas at room temperature for 3 hours. The reaction mixture was then worked up in the same manner as Example 132 to give 120 mg of 20-(5,5-dimethyl-1,3-dioxan-2-yl)-3β-(N-methylcarbamoyl)oxy-1α-(N-phenylcarbamoyl)oxy-7α-(methoxycarbonyl)oxypregn-5-ene showing the following physical properties.

$^1$H-NMR spectrum (90 MHz) $\delta_{TMS}^{CDCl3}$: 0.70 (s, 6 H), 1.05 (d, J=6.2 Hz, 3 H), 1.05 (s, 3 H), 1.18 (s, 3 H), 2.76 (d, J=6 Hz, 3 H), 3.34 (d, J=10.5 Hz, 1 H), 3.44 (d, J=10.5 Hz, 1 H), 3.57 (d, J=10.5 Hz, 2 H), 3.78 (s, 3 H), 4.38 (d, J=2.4 Hz, 1 H), 4.65–5.15 (3 H), 5.20 (1 H), 5.90 (d, J=5.7 Hz, 1 H), 6.75 (br. s, 1 H), 7.1–7.7 (5 H).

IR spectrum (KBr): 1745, 1720, 1710 cm$^{-1}$.

EXAMPLE 136

In 10 ml of dimethyl carbonate was dissolved 350 mg of 20-(5,5-dimethyl-1,3-dioxan-2-yl)-1α-(N,N-dimethylcarbamoyl)oxy-3β-(N-phenylcarbamoyl)oxypregn-6-en-5α-ol, followed by addition of 50 mg of pyridinium p-toluenesulfonate. The mixture was stirred in an atmosphere of argon gas at room temperature for 10 hours. The reaction mixture was then worked up in the same manner as Example 132 to give 150 mg of 20-(5,5-dimethyl-1,3-dioxan-2-yl)-1α-(N,N-dimethylcarbamoyl)oxy-3β-(N-phenylcarbamoyl)oxy-7α-(methoxycarbonyl)oxypregn-5-ene showing the following physical properties.

$^1$H-NMR spectrum (90 MHz) $\delta_{TMS}^{CDCl3}$: 0.70 (s, 6 H), 1.05 (d, J=6.2 Hz, 3 H), 1.08 (s, 3 H), 1.18 (s, 3 H), 2.78 & 2.81 (each s, 6 H), 3.34 (d, J=10.5 Hz, 1 H), 3.44 (d, J=10.5 Hz, 1 H), 3.57 (d, J=10.5 Hz, 2 H), 3.76 (s, 3 H), 4.38 (d, J=2.4 Hz, 1 H), 4.65–5.15 (3 H), 5.90 (d, J=5.7 Hz, 1 H), 6.80 (br. s, 1 H), 7.1–7.7 (5 H).

IR spectrum (KBr): 1745, 1720, 1695 cm$^{-1}$.

EXAMPLE 137

In 10 ml of dimethyl carbonate was dissolved 350 mg of 20-(5,5-dimethyl-1,3-dioxan-2-yl)-1α-(tert-butyldimethylsilyl)oxy-3β-(N,N-dimethylcarbamoyl)oxypregn-6-en-5α-ol, followed by addition of one drop of concentrated sulfuric acid. The mixture was stirred in an atmosphere of argon gas under ice-cooling for 1 hour. The reaction mixture was then worked up in the same manner as Example 132 to give 95 mg of 20-(5,5-dimethyl-1,3-dioxan-2-yl)-1α -(tert-butyldimethylsilyl)oxy-3β-(N,N-dimethylcarbamoyl)oxy-7α-(methoxycarbonyl)oxypregn-5-ene showing the following physical properties.

$^1$H-NMR spectrum (90 MHz) $\delta_{TMS}^{CDCl3}$: 0.15 (s, 6 H), 0.70 (s, 6 H), 0.97 (s, 9 H), 1.05 (d, J=6.2 Hz, 3 H), 1.08 (s, 3 H), 1.18 (s, 3 H), 2.78 & 2.81 (each s, 6 H), 3.34 (d, J=10.5 Hz, 1 H), 3.44 (d, J=10.5 Hz, 1 H), 3.57 (d, J=10.5 Hz, 2 H), 3.77 (s, 3 H), 4.2–4.5 (3 H), 4.7–5.1 (2 H), 5.90 (d, J=5.8 Hz, 1 H).

IR spectrum (KBr): 1745, 1695 cm$^{-1}$.

EXAMPLE 138

In 10 ml of dimethyl carbonate was dissolved 400 mg of 20-(5,5-dimethyl-1,3-dioxan-2-yl)-3β-(tert-butyldimethylsilyl)oxy-1α-(methoxymethyl)oxypregn-6-en-5α-ol, followed by addition of 0.2 ml of acetic acid. The mixture was refluxed in an atmosphere of argon gas for 12 hours. The reaction mixture was then worked up in the same manner as Example 132 to give 120 mg of 20-(5,5-dimethyl-1,3-dioxan-2-yl)-3β-(tert-butyldimethylsilyl)oxy-1α-(methoxymethyl)oxy-7α-(methoxycarbonyl)oxypregn-5-ene showing the following physical properties.

$^1$H-NMR spectrum (90 MHz) $\delta_{TMS}^{CDCl_3}$: 0.13 (s, 6 H), 0.70 (s, 6 H), 0.95 (s, 9 H), 1.05 (d, J=6.2 Hz, 3 H), 1.08 (s, 3 H), 1.18 (s, 3 H), 33.34 (d, J=10.5 Hz, 1 H), 3.36 (s, 3 H), 3.44 (d, J=10.5 Hz, 1 H), 3.57 (d, J=10.5 Hz, 2 H), 3.78 (s, 3 H), 4.10–4.50 (2 H), 4.38 (d, J=2.4 Hz, 1 H), 4.7–5.1 (2 H), 5.90 (d, J=5.7 Hz, 1 H).

IR spectrum (KBr): 1745 cm$^{-1}$.

EXAMPLE 139

In 10 ml of dimethyl carbonate was dissolved 350 mg of 20-(1,3-dioxolan-2-yl)-1α-acetoxy-3β-(methoxyoxypregn-6-en-5α-ol, following by addition of 0.2 ml of acetic acid. The mixture was stirred in an atmosphere of argon gas at a temperature of 100° C. for 12 hours. The reaction mixture was then worked up in the same manner as Example 132 to give 130 mg of 20-(1,3-dioxolan-2-yl)-1α-acetoxy-3β-(methoxymethyl)oxy-7α-(methoxycarbonyl)oxypregn-5-ene showing the following physical properties.

$^1$H-NMR spectrum (90 MHz) $\delta_{TMS}^{CDCl_3}$: 0.75 (s, 3 H), 0.95 (d, J=6.2 Hz, 3 H), 1.07 (s, 3 H), 2.07 (s, 3 H), 3.35 (s, 3 H), 3.70–4.05 (m, 4 H), 3.78 (s, 3 H), 4.30 (m, 1 H), 4.79 (br. s, 2 H), 4.7–5.1 (2 H), 5.90 (d, J=5.7 Hz, 1 H).

IR spectrum (KBr): 1745, 1735 cm$^{-1}$.

EXAMPLE 140

In 5 ml of methanol was dissolved 100 mg of 20-(5,5-dimethyl-1,3-dioxan-2-yl)-1α,3β,7α-tris(methoxycarbonyloxy)pregn-5-ene, followed by addition of 30 mg of sodium methoxide, and the mixture was stirred at room temperature for 5 hours. The reaction mixture was poured in water and extracted with methylene chloride. The extracts were pooled, washed with aqueous sodium chloride solution and concentrated under reduced pressure. The concentrate was recrystallized from ethyl acetate to give 65 mg of 20-(5,5-dimethyl-1,3-dioxan-2-yl)pregn-5-ene-1α,3β,7α-triol showing the following physical properties.

$^1$H-NMR spectrum (90 MHz) $\delta_{TMS}^{CDCl_3}$: 0.68 (s, 6 H), 0.95 (s, 3 H), 1.05 (d, J=6.2 Hz, 3 H), 1.16 (s, 3 H), 3.25 (d, J=10.8 Hz, 1 H), 3.42 (d, J=10.8 Hz, 1 H), 3.60 (d, J=10.8 Hz, 2 H), 4.37 (br. s, 1 H), 3.7–4.2 (3 H), 5.80 (d, J=5.7 Hz, 1 H).

IR spectrum (KBr): 3450 cm$^{-1}$.

EXAMPLE 141

The reaction and workup procedures of Example 140 were repeated except that 95 mg of 20-(5,5-dimethyl-1,3-dioxan-2-yl)-1α-(tert-butyldimethylsilyl)oxy-3β-(N,N-dimethylcarbamoyl)oxy-7α-(methoxycarbonyl)oxypregn-5-ene was used in lieu of 100 mg of 20-(5,5-dimethyl-1,3-dioxan-2-yl)-1α,3β,7α-tris(methoxycarbonyloxy)pregn-5-ene to give 55 mg of 20-(5,5-dimethyl-1,3-dioxan-2-yl)-1α-(tert-butyldimethylsilyl)oxypregn-5-ene-3β,7α-diol showing the following physical properties.

$^1$H-NMR spectrum (90 MHz) $\delta_{TMS}^{CDCl_3}$: 0.15 (s, 6 H), 0.70 (s, 6 H), 0.92 (s, 3 H), 0.97 (s, 9 H), 1.05 (d, J=6.2 Hz, 3 H), 1.18 (s, 3 H), 3.34 (d, J=10.5 Hz, 1 H), 3.44 (d, J=10.5 Hz, 1 H), 3.57 (d, J=10.5 Hz, 2 H), 3.8–4.5 (4 H), 5.70 (d, J=5.8 Hz, 1 H).

IR spectrum (KBr): 3350 cm$^{-1}$.

EXAMPLE 142

The reaction and workup procedures of Example 140 were repeated except that 120 mg of 20-(5,5-dimethyl-1,3-dioxan-2-yl)-3β-(tert-butyldimethylsilyl)oxy-1α-(methoxymethyl)oxy-7α-(methoxycarbonyl)oxypregn-5-ene was used in lieu of 100 mg of 20-(5,5-dimethyl-1,3-dioxan-2-yl)-1α,3β,7α-tris(methoxycarbonyloxy)pregn-5-ene to give 65 mg of 20-(5,5-dimethyl-1,3-dioxan-2-yl)-3β-(tert-butyldimethylsilyl)oxy-1α-(methoxymethyl)oxypregn-5-en-7α-ol showing the following physical properties.

$^1$H-NMR spectrum (90 MHz) $\delta_{TMS}^{CDCl_3}$: 0.13 (s, 6 H), 0.70 (s, 6 H), 0.95(s, 9 H), 1.05 (d, J=6.2 Hz, 3 H), 1.08 (s, 3 H), 1.18 (s, 3 H), 3.34 (d, J=10.5 Hz, 1 H), 3.36 (s, 3 H), 3.44 (d, J=10.5 Hz, 1 H), 3.57 (d, J=10.5 Hz, 2 H), 3.78 (s, 3 H), 4.10–4.50 (3 H), 4.38 (d, J=2.4 Hz, 1 H), 4.79 (br. s, 2 H), 5.90 (d, J=5.7 Hz 1 H).

IR spectrum (KBr): 3400 cm$^{-1}$.

EXAMPLE 143

The reaction and workup procedures of Example 140 were repeated except that 90 mg of 20-(1,3-dioxolan-2-yl)-1α-acetoxy-3β-(methoxymethyl)oxy-7α-(methoxycarbonyl)oxypregn-5-ene was used in lieu of 100 mg of 20-(5,5-dimethyl-1,3-dioxan-2-yl)-1α,3β,7α-tris(methoxycarbonyloxy)pregn-5-ene to give 65 mg of 20-(1,3-dioxolan-2-yl)-3β-(methoxymethyl)oxypregn-5-ene-1α,7α-diol showing the following properties.

$^1$H-NMR spectrum (90 MHz) $\delta_{TMS}^{CDCl_3}$: 0.75 (s, 3 H), 0.94 (s, 3 H), 0.95 (d, J=6.2 Hz, 3 H), 3.35 (s, 3 H), 3.70–4.05 (m, 4 H), 3.8–4.3 (3 H), 4.79 (br. s, 2 H), 5.75 (d, J=5.7 Hz, 1 H).

IR spectrum (KBr): 3400 cm$^{-1}$.

EXAMPLE 144

The reaction and workup procedures of Example 140 were repeated except that 85 mg of 3β-benzoyloxy-21,21-dimethoxy-20-methyl-1α-(N-methylcarbamoyl)oxy-7α-(methoxycarbonyl)oxypregn-5-ene was used in lieu of 100 mg of 20-(5,5-dimethyl-1,3-dioxan-2-yl)-1α,3β,7α-tris(methoxycarbonyloxy)pregn-5-ene to give 45 mg of 21,21-dimethoxy-20-methylpregn-5-ene-1α,3β,7α-triol showing the following physical properties.

$^1$H-NMR spectrum (90 MHz) $\delta_{TMS}^{CDCl_3}$: 0.69 (s, 3 H), 0.94 (s, 3 H), 0.95 (d, J=6.2 Hz, 3 H), 3.38 & 3.40 (each s, 6 H), 3.7–4.3 (3 H), 4.40 (br. s, 1 H), 5.75 (d, J=5.7 Hz, 1 H).

IR spectrum (KBr): 3350 cm$^{-1}$.

EXAMPLES 145 TO 149

The esterification reaction of the 7α-hydroxy group of compound (I-9-1b) (100 mg) and the separation and purification of the product compound (I-9-1c) were conducted in the same manner as described in Examples 104 to 108. The groups possessed by the specific compounds (I-9-1b) used in the reaction are shown in Table 1 and the groups possessed by the product compounds (I-9-1c), and the yields and IR spectra (KBr) of the latter are shown in Table 2.

bonyloxy)pregna-5,7-diene showing the same physical properties as the compound obtained in Example 124.

EXAMPLES 151 TO 155

TABLE 1

| Example | The groups possessed by material compound (I-9-1b) (Note 1) | | | | Example referred to |
|---|---|---|---|---|---|
| | $Z^6$ | $Z^7$ | $Y^1$ | $Y^2$ | |
| 145 | H | H | $-OCH_2C(CH_3)(CH_3)CH_2O-$ | | 104 |
| 146 | H | $-Si(CH_3)_2C(CH_3)_3$ | $-OCH_2C(CH_3)(CH_3)CH_2O-$ | | 105 |
| 147 | $-Si(CH_3)_2C(CH_3)_3$ | $-CH_2OCH_3$ | $-OCH_2C(CH_3)(CH_3)CH_2O-$ | | 106 |
| 148 | $-CH_2OCH_3$ | H | $-OCH_2CH_2O-$ | | 107 |
| 149 | H | H | $-OCH_3$ | $-OCH_3$ | 108 |

(Note 1)
Refer to general formula (I-9-1b)

TABLE 2

| Example | The groups possessed by product compound (I-9-1c) (Note 1) | | | | | Compound (I-9-1c) | |
|---|---|---|---|---|---|---|---|
| | $Z^3$ | $Z^4$ | $Z^8$ | $Y^1$ | $Y^2$ | Yield (mg) | IR (cm$^{-1}$) |
| 145 | $-COCH_3$ | $-COCH_3$ | $-COCH_3$ | $-OCH_2C(CH_3)(CH_3)CH_2O-$ | | 100 | 1735 |
| 146 | $-COC_6H_5$ | $-Si(CH_3)_2C(CH_3)_3$ | $-COC_6H_5$ | $-OCH_2C(CH_3)(CH_3)CH_2O-$ | | 95 | 1720 |
| 147 | $-Si(CH_3)_2C(CH_3)_3$ | $-CH_2OCH_3$ | $-CONHCH_3$ | $-OCH_2C(CH_3)(CH_3)CH_2O-$ | | 105 | 1710 |
| 148 | $-CH_2OCH_3$ | $-CONHC_6H_5$ | $-CONHC_6H_5$ | $-OCH_2CH_2O-$ | | 98 | 1720 |
| 149 | $-CON(CH_3)_2$ | $-CON(CH_3)_2$ | $-CON(CH_3)_2$ | $-OCH_3$ | $-OCH_3$ | 92 | 1695 |

(Note 1)
Refer to general formula (I-9-1c)

EXAMPLE 150

In 10 ml of dioxane was dissolved 25 mg of tris(dibenzylideneacetone)dipalladium(chloroform), followed by addition of 45 μl of tri-n-butylphosphine. The mixture was stirred in an atmosphere of argon gas at room temperature for 10 minutes. To this mixture was added a solution of 270 mg of 20-(5,5-dimethyl-1,3-dioxan-2-yl)-1α,3β,7α-tris(methoxycarbonyloxy)pregn-5-ene in 10 ml of dioxane and the mixture was refluxed for 12 hours. The resulting reaction mixture was cooled to room temperature and filtered with the aid of Florisil. The filtrate was concentrated under reduced pressure and the concentrate was purified by column chromatography. The procedure yielded 118 mg of 20-(5,5-dimethyl-1,3-dioxan-2-yl)-1α,3β-bis(methoxycar- The conjugated diene-forming reaction of compound (I-9-1c) (in a given amount) in the presence of the palladium compound and tertiary phosphine (provided, however, that no tertiary phosphine was used in Example 155) and the separation and purification of the resulting product compound (I-5-3) were carried out in the same manner as described in Example 150. The groups possessed by the specific compounds (I-9-1c) used for the reaction, the amounts of said compounds and the species of palladium compound and tertiary phosphine used are shown in Table 3 and the yields and physical values of the product compounds (I-5-3) are shown in Table 4. The amounts of palladium compound and tertiary phosphine were 0.1 and 0.4 equivalents, respectively, based on compound (I-9-1c).

TABLE 3

| Example | The groups possessed by material compound (I-9-1c) (Note 1) | | | | | Amount of material compound (I-9-1c) (mg) | Species of palladium compound (Note 2) | Species of tertiary phosphine (Note 2) |
|---|---|---|---|---|---|---|---|---|
| | $Z^3$ | $Z^4$ | $Z^8$ | $Y^1$ | $Y^2$ | | | |
| 151 | —COCH$_3$ | —COCH$_3$ | —COCH$_3$ | —OCH$_2$C(CH$_3$)(CH$_3$)CH$_2$O— | | 250 | Pd(OAc)$_2$ | PPh$_3$ |
| 152 | —COC$_6$H$_5$ | —Si(CH$_3$)$_2$C(CH$_3$)$_3$ | —COC$_6$H$_5$ | —OCH$_2$C(CH$_3$)(CH$_3$)CH$_2$O— | | 220 | Pd(NO$_3$)$_2$ | PTol$_3$ |
| 153 | —Si(CH$_3$)$_2$C(CH$_3$)$_3$ | —CH$_2$OCH$_3$ | —CONHCH$_3$ | —OCH$_2$C(CH$_3$)(CH$_3$)CH$_2$O— | | 275 | PdCl$_2$ | (Ph$_2$PCH$_2$)$_2$ |
| 154 | —CH$_2$OCH$_3$ | —CONHC$_6$H$_5$ | —CONHC$_6$H$_5$ | —OCH$_2$CH$_2$O— | | 230 | Pd(acac)$_2$ | PPh$_3$ |
| 155 | —CON(CH$_3$)$_2$ | —CON(CH$_3$)$_2$ | —CON(CH$_3$)$_2$ | —OCH$_3$ | —OCH$_3$ | 200 | Pd(PPh$_3$)$_4$ | — |

(Note 1) Refer to general formula (I-9-1c)
(Note 2) Ac: an acetyl group, acac: an acetylacetonato group, Ph: a phenyl group, Tol: a tolyl group.

TABLE 4

| Example | Product compound (I-5-3) (Note 1) | | |
|---|---|---|---|
| | Yield Yield (mg) | IR spectrum (KBr) (cm$^{-1}$) | $^1$H-NMR spectrum (90 MHz) $\delta_{TMS}^{CDCl_3}$ |
| 151 | 120 | 1735 | 5.40 (m, 1 H), 5.65 (m, 1 H) |
| 152 | 90 | — | 5.38 (m, 1 H), 5.70 (m, 1 H) |
| 153 | 100 | 1710 | 5.36 (m, 1 H), 5.68 (m, 1 H) |
| 154 | 120 | 1720 | 5.36 (m, 1 H), 5.68 (m, 1 H) |
| 155 | 95 | 1695 | 5.36 (m, 1 H), 5.70 (m, 1 H) |

(Note 1) Each product compound (I-5-3) has the $Z^3$, $Z^4$, $Y^1$ and $Y^2$ possessed by the corresponding material compound (I-9-1c).

EXAMPLE 156

In 5 ml of acetone was dissolved 100 mg of 20-(5,5-dimethyl-1,3-dioxan-2-yl)-1α,3β-bis(methoxycarbonyloxy)pregna-5,7-diene, followed by addition of one drop of concentrated sulfuric acid, and the mixture was refluxed in an atmosphere of argon gas for 3 hours. The reaction mixture was poured in ice-water and extracted with ether. The extracts were pooled and washed with aqueous sodium hydrogen carbonate solution and aqueous sodium chloride solution, followed by concentration under reduced pressure. Finally the concentrate was purified by recrystallization from ether. The procedure yielded 55 mg of 1α,3β-bis(methoxycarbonyloxy)-pregna-5,7-diene-20-carbaldehyde showing the following physical properties.

$^1$H-NMR spectrum (90 MHz) $\delta_{TMS}^{CDCl_3}$: 0.66 (s, 3 H), 1.02 (s, 3 H), 1.15 (d, J=6.4 Hz, 3 H), 3.77 & 3.79 (each s, 6 H), 4.6–5.2 (2 H), 5.40 (m, 1 H), 5.65 (m, 1 H), 9.58 (d, J=3.5 Hz, 1 H).

IR spectrum (KBr): 1740, 1725 cm$^{-1}$.

EXAMPLE 157

In 5 ml of tetrahydrofuran was dissolved 100 mg of 20-(1,3-dioxolan-2-yl)-3β-acetoxy-1α-benzoyloxypregna-5,7-diene, followed by addition of 1 ml of water and 10 mg of p-toluenesulfonic acid. The mixture was stirred in an atmosphere of argon gas at 50° C. for 3 hours. The reaction mixture was then worked up in the same manner as Example 156 to give 45 mg of 3β-acetoxy-1α-benzoyloxypregna-5,7-diene-20-carbaldehyde showing the following physical properties.

$^1$H-NMR spectrum (90 MHz) $\delta_{TMS}^{CDCl_3}$: 0.66 (s, 3 H), 1.01 (s, 3 H), 1.15 (d, J=6.2 Hz, 3 H), 2.05 (s, 3 H), 4.60–5.20 (2 H), 5.38 (m, 1 H), 5.70 (m, 1 H), 7.2–7.7 (3 H), 7.9–8.2 (2 H), 9.58 (d, J=3.5 Hz, 1 H).

IR spectrum (KBr): 1735, 1725, 1720 cm$^{-1}$.

EXAMPLE 158

In 5 ml of methanol was dissolved 100 mg of 3β-benzoyloxy-21,21-dimethoxy-20-methyl-1α-(N-methylcarbamoyl)oxypregna-5,7-diene, followed by addition of 5 ml of water and 100 mg of copper sulfate. The mixture was stirred in an atmosphere of argon gas at a temperature of 60° C. for 7 hours. The reaction mixture was then worked up in the same manner as Example 156 to give 60 mg of 3β-benzoyloxy-1α-(N-methylcarbamoyl)oxypregna-5,7-diene-20-carbaldehyde showing the following physical properties.

$^1$H-NMR spectrum (90 MHz) $\delta_{TMS}^{CDCl_3}$: 0.66 (s, 3 H), 1.02 (s, 3 H), 1.15 (d, J=6.2 Hz, 3 H), 2.80 (d, J=6 Hz, 3 H), 4.6–5.2 (3 H), 5.36 (m, 1 H), 5.68 (m, 1 H), 7.2–7.7 (m, 3 H), 7.9–8.2 (m, 2 H), 9.58 (d, J=3.5 Hz, 1 H).

IR spectrum (KBr): 1725, 1720, 1710 cm$^{-1}$.

EXAMPLE 159

In 5 ml of ethanol was dissolved 105 mg of 20-(5,5-dimethyl-1,3-dioxan-2-yl)-1α-(N-phenylcarbamoyl)oxy-3β-(N-methylcarbamoyl)oxypregna-5,7-diene, followed by addition of 1 ml of 3N-hydrochloric acid, and the mixture was stirred in an atmosphere of argon gas at 40° C. for 3 hours. The reaction mixture was then worked up in the same manner as Example 156 to give 52 mg of 3β-(N-methylcarbamoyl)oxy-1α-(N-phenylcarbamoyl)oxypregna-5,7-diene-20-carbaldehyde showing the following physical properties.

$^1$H-NMR spectrum (90 MHz) $\delta_{TMS}^{CDCl_3}$: 0.65 (s, 3 H), 1.02 (s, 3 H), 1.15(d, J=6.2 Hz, 3 H), 2.76 (d, J=6 Hz, 3 H), 4.65–5.15 (2 H), 5.20 (1 H), 5.36 (m, 1 H), 5.68 (m, 1 H), 6.75 (br. s, 1 H), 7.1–7.7 (5 H), 9.58 (d, J=3.5 Hz, 1 H).

IR spectrum (KBr): 1725, 1720, 1710 cm$^{-1}$.

EXAMPLE 160

In 10 ml of 2-butanone was dissolved 95 mg of 20-(5,5-dimethyl-1,3-dioxan-2-yl)-1α-(N,N-dimethylcarbamoyl)oxy-3β-(N-phenylcarbamoyl)oxypregna-5,7-diene, followed by addition of 50 mg of pyridinium p-toluenesulfonate, and the mixture was stirred in an atmosphere of argon gas at a temperature of 50° C. for 10 hours. The reaction mixture was then worked up in the same manner as Example 156 to give 45 mg of 1α-(N,N-dimethylcarbamoyl)oxy-3β-(N-phenylcarbamoyl)oxypregna-5,7-diene-20-carbaldehyde showing the following physical properties.

$^1$H-NMR spectrum (90 MHz) $\delta_{TMS}^{CDCl_3}$: 0.66 (s, 3 H), 1.02 (s, 3 H), 1.15 (d, J=6.2 Hz, 3 H), 2.78 & 2.81 (each s, 6 H), 4.65–5.15 (2 H), 5.36 (m, 1 H), 5.70 (m, 1 H), 6.80 (br. s, 1 H), 7.1–7.7 (5 H), 9.60 (d, J=3.5 Hz, 1 H).

IR spectrum (KBr): 1725, 1720, 1695 cm$^{-1}$.

EXAMPLE 161

In 10 ml of acetone was dissolved 110 mg of 20-(5,5-dimethyl-1,3-dioxan-2-yl)-1α-(tert-butyldimethylsilyl)oxy-3β-(N,N-dimethylcarbamoyl)oxypregna-5,7diene, followed by addition of 10 mg of p-toluenesulfonic acid. The mixture was refluxed in an atmosphere of argon gas for 4 hours. The reaction mixture was then worked up in the same manner as Example 156 to give 63 mg of 1α-(tert-butyldimethylsilyl)oxy-3β-(N,N-dimethylcarbamoyl)oxypregna-5,7-diene-20-carbaldehyde showing the following physical properties.

$^1$H-NMR spectrum (90 MHz) $\delta_{TMS}^{CDCl_3}$: 0.15 (s, 6 H), 0.66 (s, 3 H), 0.97 (s, 9 H), 1.02 (s, 3 H), 1.15 (d, J=6.2 Hz, 3 H), 2.78 & 2.81 (each s, 6 H), 4.2–4.5 (1 H), 4.90 (m, 1 H), 5.38 (m, 1 H), 5.68 (m, 1 H), 9.60 (d, J=3.4 Hz, 1 H).

IR spectrum (KBr): 1725, 1695 cm$^{-1}$.

EXAMPLE 162

In 5 ml of tetrahydrofuran was dissolved 20-(5,5-dimethyl-1,3-dioxan-2-yl)-3β-(tert-butyldimethylsilyl)oxy-1α-(methoxymethyl)oxypregna-5,7-diene, followed by addition of 5 ml of 80% acetic acid. The mixture was refluxed in an atmosphere of argon gas for 12 hours. The reaction mixture was then worked up in the same manner as Example 156 to give 50 mg of 3β-(tert-butyldimethylsilyl)oxy-1α-(methoxymethyl)oxypregna-5,7-diene-20-carbaldehyde showing the following physical properties.

$^1$H-NMR spectrum (90 MHz) $\delta_{TMS}^{CDCl_3}$: 0.13 (s, 6 H), 0.66 (s, 3 H), 0.95 (s, 9 H), 1.01 (s, 3 H), 1.14 (d, J=6.2 Hz, 3 H), 3.40 (s, 3 H), 4.10–4.50 (2 H), 4.80 (br. s, 2 H), 5.35 (m, 1 H), 5.70 (m, 1 H), 9.59 (d, J=3.5 Hz, 1 H).

IR spectrum (KBr): 1725 cm$^{-1}$.

EXAMPLE 163

In 10 ml of acetone was dissolved 100 mg of 20-(1,3-dioxolan-2-yl)-1α-acetoxy-3β-(methoxymethyl)oxypregna-5,7-diene, followed by addition of one drop of 70% perchloric acid, and the mixture was refluxed in an atmosphere of argon gas for 2 hours. The reaction mixture was then worked up in the same manner as Example 156 to give 40 mg of 1α-acetoxy-3β-(methoxymethyl)oxypregna-5,7-diene-20-carbaldehyde showing the following physical properties.

$^1$H-NMR spectrum (90 MHz) $\delta_{TMS}^{CDCl_3}$: 0.66 (s, 3 H), 1.00 (s, 3 H), 1.16 (d, J=6.2 Hz, 3 H), 2.07 (s, 3 H), 3.35 (s, 3 H), 4.30 (m, 1 H), 4.65 (br. s, 2 H), 4.99 (1 H), 5.35 (m, 1 H), 5.70 (m, 1 H), 9.57 (d, J=3.5 Hz, 1 H).

IR spectrum (KBr): 1735, 1725 cm$^{-1}$.

EXAMPLE 164

In 10 ml of methanol was dissolved 100 mg of 1α,3β-bis(methoxycarbonyloxy)pregna-5,7-diene-20-carbaldehyde, followed by addition of 100 mg of potassium carbonate. The mixture was stirred at room temperature for 1 hour. The reaction mixture thus obtained was poured in water and extracted with methylene chloride. The extracts were pooled and washed with aqueous sodium chloride solution, followed by concentration under reduced pressure. The concentrate was recrystallized from ether to recover 78 mg of 3β-hydroxy-1α-(methoxycarbonyloxy)pregna-5,7-diene-20-carbaldehyde showing the following physical properties.

$^1$H-NMR spectrum (90 MHz) $\delta_{TMS}^{CDCl_3}$: 0.66 (s, 3 H), 1.02 (s, 3 H), 1.15 (d, J=6.4 Hz, 3 H), 3.77 (s, 3 H), 4.03 (m, 1 H), 4.90 (br. s, 1 H), 5.40 (m, 1 H), 5.65 (m, 1 H), 9.58 (d, J=3.5 Hz, 1 H).

IR spectrum (KBr): 3450, 1740, 1725 cm$^{-1}$.

EXAMPLE 165

In 10 ml of methanol was dissolved 100 mg of 1α-acetoxy-3β-(methoxymethyl)oxypregna-5,7-diene-20-carbaldehyde, followed by addition of 50 mg of sodium methoxide. The mixture was stirred in an atmosphere of argon gas for 2 hours. The reaction mixture was then worked up in the same manner as Example 164 to give 80 mg of 1α-hydroxy-3β-(methoxymethyl)oxypregna-5,7-diene-20-carbaldehyde showing the following physical properties.

$^1$H-NMR spectrum (90 MHz) $\delta_{TMS}^{CDCl_3}$: 0.66 (s, 3 H), 0.94 (s, 3 H), 1.16 (d, J=6.2 Hz, 3 H), 3.35 (s, 3 H), 3.76 (br. s, 1 H), 4.20 (m, 1 H), 4.65 (br. s, 2 H), 5.35 (m, 1 H), 5.70 (m, 1 H), 9.57 (d, J=3.5 Hz, 1 H).

IR spectrum (KBr): 3450, 1725 cm$^{-1}$.

EXAMPLE 166

The reaction and workup procedures of Example 164 were repeated except that 100 mg of 20-(5,5-dimethyl-1,3-dioxan-2-yl)-1α,3β-bis(methoxycarbonyloxy)pregna-5,7-diene was used in lieu of 100 mg of 1α,3β-bis(methoxycarbonyloxy)pregna-5,7-diene-20-carbaldehyde to give 85 mg of 20-(5,5-dimethyl-1,3-dioxan-2-yl)-1α-(methoxycarbonyl)oxypregna-5,7-dien-3β-ol showing the following physical properties.

$^1$H-NMR spectrum (90 MHz) $\delta_{TMS}^{CDCl_3}$: 0.63 (s, 3 H), 0.70 (s, 3 H), 1.02 (s, 3 H), 1.09 (d, J=6.4 Hz, 3 H), 1.17 (s, 3 H), 3.2–3.7 (4 H), 3.77 (s, 3 H), 4.05 (m, 1 H), 4.40 (br. s, 1 H), 4.90 (br. s, 1 H), 5.40 (m, 1 H), 5.65 (m, 1 H).

IR spectrum (KBr): 3450, 1740 cm$^{-1}$.

EXAMPLE 167

The reaction and workup procedures of Example 164 were repeated except that 100 mg of 3β-benzoyloxy-21,21-dimethoxy-20-methyl-1α-(N-methylcarbamoyl)oxypregna-5,7-diene was used in lieu of 100 mg of 1α,3β-bis(methoxycarbonyloxy)pregna-5,7-diene-20-carbaldehyde to give 65 mg of 21,21-dimethoxy-20- methylpregna-5,7-diene-1α,3β diol showing the following physical properties.

1H-NMR spectrum (90 MHz) $\delta_{TMS}^{CDCl3}$: 0.75 (s, 3 H), 0.94 (s, 3 H), 0.96 (d, J=6.2 Hz, 3 H), 3.38 & 3.41 (each s, 6 H), 3.76 (br. s, 1 H), 4.03 (m, 1 H), 4.38 (br. s, 1 H), 5.36 (m, 1 H), 5.68 (m, 1 H).

IR spectrum (KBr): 3400 cm$^{-1}$.

EXAMPLE 168

The reaction and workup procedures of Example 164 were repeated except that 100 mg of 20-(1,3-dioxolan-2-yl)-1α-acetoxy-3β-(methoxymethyl)oxypregna-5,7-diene was used in lieu of 100 mg of 1α,3β-bis(methoxycarbonyloxy)pregna-5,7-diene-20-carbaldehyde to give 72 mg of 20-(1,3-dioxolan-2-yl)-3β-(methoxymethyl)oxypregna-5,7-dien-1α-ol showing the following physical properties.

1H-NMR spectrum (90 MHz) $\delta_{TMS}^{CDCl3}$: 0.79 (s, 3 H), 0.95 (d, J=6.2 Hz, 3 H), 0.96 (s, 3 H), 3.35 (s, 3 H), 3.7–4.0 (5 H), 4.30 (m, 1 H), 4.65 (br. s, 2 H), 4.80 (br. s, 1 H), 5.35 (m, 1 H), 5.70 (m, 1H).

IR spectrum (KBr): 3350 cm$^{-1}$.

EXAMPLE 169

The reaction and workup procedures of Example 156 were repeated except that 100 mg of 20-(5,5-dimethyl-1,3-dioxan-2-yl)-3β-(methoxycarbonyl)oxypregna-5,7-dien-1α-ol was used in lieu of 100 mg of 20-(5,5-dimethyl-1,3-dioxan-2-yl)-1α,3β-bis(methoxycarbonyloxy)-pregna-5,7-diene to give 55 mg of 3β-hydroxy-1α-(methoxycarbonyl)oxypregna-5,7-diene-20-carbaldehyde showing the following physical properties.

1H-NMR spectrum (90 MHz) $\delta_{TMS}^{CDCl3}$: 0.66 (s, 3 H), 1.02 (s, 3 H), 1.15 (d, J=6.4 Hz, 3 H), 3.77 (s, 3 H), 4.05 (m, 1 H), 4.40 (br. s, 1 H), 4.65 (br. s, 2 H), 5.40 (m, 1 H), 5.65 (m, 1 H), 9.58 (d, J=3.5 Hz, 1 H).

IR spectrum (KBr): 3450, 1740, 1725 cm$^{-1}$.

EXAMPLE 170

The reaction and workup procedures of Example 156 were repeated except that 100 mg of 21,21-dimethoxy-20-methyl-pregna-5,7-diene-1α,3β-diol was used in lieu of 100 mg of 20-(5,5-dimethyl-1,3-dioxan-2-yl)-1α,3β-bis(methoxycarbonyloxy)pregna-5,7-diene to give 45 mg of 1α,3β-dihydroxypregna-5,7-diene-20-carbaldehyde showing the following physical properties.

1H-NMR spectrum (90 MHz) $\delta_{TMS}^{CDCl3}$: 0.66 (s, 3 H), 0.94 (s, 3 H), 1.15 (d, J=6.2 Hz, 3 H), 3.76 (br. s, 1 H), 4.03 (m, 1 H), 5.36 (m, 1 H), 5.68 (m, 1 H), 9.58 (d, J=3.5 Hz, 1 H).

IR spectrum (KBr): 3400, 1725 cm$^{-1}$.

EXAMPLE 171

The reaction and workup procedures of Example 156 were repeated except that 100 mg of 20-(1,3-dioxolan-2-yl)-3β-(methoxymethyl)oxypregna-5,7-dien-1α-ol was used in lieu of 100 mg of 20-(5,5-dimethyl-1,3-dioxan-2-yl)-1α,3β-bis(methoxycarbonyloxy)pregna-5,7-diene to give 53 mg of 1α-hydroxy-3β-(methoxymethyl)oxypregna-5,7-diene-20-carbaldehyde showing the following physical properties.

1H-NMR spectrum (90 MHz) $\delta_{TMS}^{CDCl3}$: 0.65 (s, 3 H), 0.95 (d, J=6.2 Hz, 3 H), 0.96 (s, 3 H), 3.35 (s, 3 H) 3.77 (br. s, 1 H), 4.30 (m, 1 H), 4.65 (br. s, 2 H), 5.35 (m, 1 H), 5.70 (m, 1 H), 9.58 (d, J=3.5 Hz, 1 H).

IR spectrum (KBr): 3350, 1725 cm$^{-1}$.

EXAMPLE 172

In 10 ml of methylene chloride was dissolved 0.50 g of 1α,3β-dihydroxypregna-5,7-diene-20-carbaldehyde, followed by addition of 1 ml of 3,4-dihydropyran and 0.05 g of p-toluenesulfonic acid. The mixture was stirred at room temperature for 2 hours. The reaction mixture thus obtained was diluted with ether, washed successively with aqueous sodium hydrogen carbonate solution and aqueous sodium chloride solution, and dried over sodium sulfate, followed by concentration under reduced pressure. Finally the concentrate was purified by column chromatography to give 0.48 g of 1α,3β-bis(tetrahydropyran-2-yloxy)pregna-5,7-diene-20-carbaldehyde showing the following physical properties.

IR spectrum (KBr): 1725 cm$^{-1}$.

Reference Examples (1) To 20 ml of a tetrahydrofuran solution of the isoamylmagnesium bromide prepared from 2.27 g of isoamyl bromide and 0.48 g of magnesium was slowly added a solution of 5.12 g of 1α, 3β-bis(tetrahydropyran-2-yloxy)pregna-5,7-diene-20-carbaldehyde in 30 ml of tetrahydrofuran under ice-cooling. After the addition, the mixture was further stirred at 0° C. for 1 hour. To the reaction mixture thus obtained was added 2N aqueous sodium hydroxide solution, followed by extraction with diethyl ether. The extract was washed with aqueous sodium chloride solution and dried over anhydrous sodium sulfate. The low-boiling fraction was then distilled off under reduced pressure and the residue was purified by silica gel column chromatography. The procedure yielded 4.84 g of 1α,3β-bis(tetrahydropyran-2-yloxy)cholesta-5,7-dien-22-ol (yield: 83%) showing the following physical property.

FD mass spectrum: [M]$^+$ 584.

(2) In 20 ml of pyridine was dissolved 0.58 g of the 1α,3β-bis(tetrahydropyran-2-yloxy)cholesta-5,7-dien-22-ol obtained as above. To this solution was added 0.12 g of methanesulfonyl chloride and the mixture was stirred at 0° C. for 2 hours. Then, at room temperature, the reaction mixture was diluted with water and extracted with diethyl ether. The extract was washed with water and dried over anhydrous sodium sulfate. The low-boiling fraction was then distilled off under reduced pressure and the residue was purified by silica gel column chromatography. The procedure yielded 0.57 g of 1α,3β-bis(tetrahydropyran-2-yloxy)cholesta-5,7-dien-22-yl methanesulfonate (yield: 86%).

(3) To a solution of 0.10 g of lithium aluminum hydride in 5 ml of tetrahydrofuran was added 0.66 g of 1α,3β-bis(tetrahydropyran-2-yloxy)cholesta-5,7-dien-22-yl methanesulfonate under heating and the mixture was refluxed for 2 hours. The resulting reaction mixture was cooled and, then, water and diluted hydrochloric acid were added in succession. The mixture was stirred at room temperature for 2 hours. The resulting solution was diluted with water and extracted with diethyl ether. The extract was washed with diluted hydrochloric acid and aqueous sodium chloride solution and dried over anhydrous sodium sulfate. The low-boiling fraction was then distilled off and the residue was purified by silica gel column chromatography and recrystallized from methanol. The procedure yielded 0.18 g of cholesta-5,7-diene-1α,3β-diol (yield: 45%) showing the following physical properties.

m.p.: 155°–158° C.

UV spectrum $\lambda_{max}$ (ethanol): 263, 272, 282 nm.
FD mass spectrum: [M]+ 400.

Industrial Applicability

The invention provides novel pregnane derivatives which are of use as synthetic intermediates for the production of vitamin $D_3$ derivatives having a hydroxy group in the 1α-position such as 1α-hydroxy-vitamin $D_3$.

Reference to the deposited microorganisms under Rule 13-2 of the Rules.

Culture collection: Fermentation Research Institute, the Agency of Industrial Science and Technology, the Ministry of International Trade and Industry Address: 1-3, Higashi 1 chome, Tsukuba-shi, Ibaraki Prefecture, Japan Deposit Nos. and dates:
1. FERM BP-182 Jan. 4, 1982
2. FERM BP-204 Jan. 4, 1982

We claim:

1. A pregnane derivative of the formula

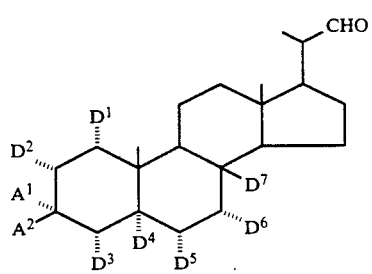

wherein $A^1$ is in the α-configuration and represents a hydrogen atom or a hydroxyl group, and $A^2$ is such that where $A^1$ is in the α-configuration and represents a hydrogen atom, $A^2$ is in the β-configuration and represents a hydroxyl group, an acyloxy group, a lower alkoxycarbonyloxy group, and N-lower alkylcarbamoyloxy group, an N-arylcarbamoyloxy group, and N,N-di(lower alkyl)carbamoyloxy group, a tri-lower alkyl or phenyl substituted silyloxy group, an alkoxymethoxy group or an alkoxymethoxy group substituted by methoxy and that where $A^1$ is in the α-configuration and represents a hydroxyl group, $A^2$ is in the β-configuration and represents a hydrogen atom, or $A^1$ and $A^2$ jointly represent an oxo group (=O); $D^1$ is in the α-configuration and represents a hydroxyl group, an acyloxy group, a lower alkoxycarbonyloxy group, and N-lower alkylcarbamoyloxy group, an N-arylcarbamoyloxy group, an N,N-di(lower alkyl)carbamoyloxy group, a tri-lower alkyl or phenyl substituted silyloxy group, an alkoxymethoxy group or an alkoxymethoxy group substituted by methoxy, and $D^2$ is in the α-configuration and represents a hydrogen atom, or $D^1$ and $D^2$ jointly represent an epoxy group (—O—) which is in the α-configuration or a single bond; $D^3$ is in the α-configuration and represents a hydrogen atom, $D^4$ is in the α-configuration and represents a hydroxyl group, $D^5$ is in the α-configuration and represents a hydrogen atom, $D^6$ is in the α-configuration and represents a hydroxyl group, a lower alkoxycarbonyloxy group, an acyloxy group, an N-lower alkylcarbamoyloxy group, an N-arylcarbamoyloxy group or an N,N-di(lower alkyl)carbamoyloxy group, $D^7$ is in the β-configuration and represents a hydrogen atom; provided that $D^3$ and $D^4$ may jointly represent an epoxy group (—O—) which is in the α-configuration or a single bond, $D^4$ and $D^5$ may jointly represent a single bond, $D^5$ and $D^6$ may jointly represent an epoxy group (—O—) which is int he α-configuration or a single bond, and $D^6$ and $D^7$ may jointly represent a single bond.

2. The pregnane derivative of claim 1, which has the formula

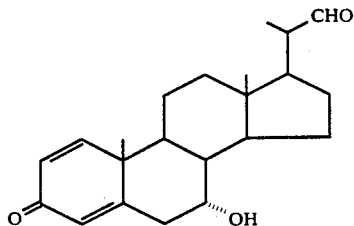

3. The pregnane derivative of claim 1, which has the formula

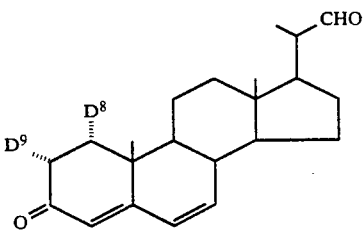

wherein $D^8$ and $D^9$ jointly represent an epoxy group (—O—) which is in the α-configuration or a single bond.

4. The pregnane derivative of claim 1, which has the formula

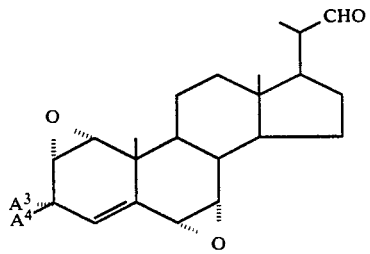

where $A^3$ is in the α-configuration and represents a hydrogen atom, $A^4$ is in the β-configuration and represents a hydroxyl group or a lower alkanoyloxy group, or $A^3$ and $A^4$ jointly represent an oxo group (=O).

5. The pregnane derivative of claim 1, which has the formula

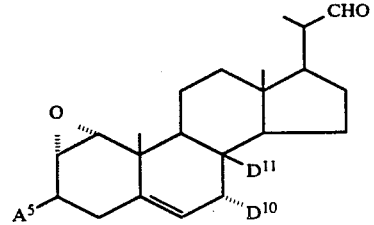

wherein $A^5$ is in the β-configuration and represents a hydroxyl group or a lower alkanoyloxy group; $D^{10}$ is in the α-configuration and represents a hydroxyl group, a lower alkoxycarbonyloxy group, a lower alkanoyloxy group, an N-lower alkylcarbamoyloxy group, an N-arylcarbamoyloxy group or an N,N-di(lower alkyl)carbamoyloxy group, and $D^{11}$ is in the $\beta$-configuration and represents a hydrogen atom, or $D^{10}$ and $D^{11}$ jointly represent a single bond.

6. A pregnane derivative of claim 1, which has the formula

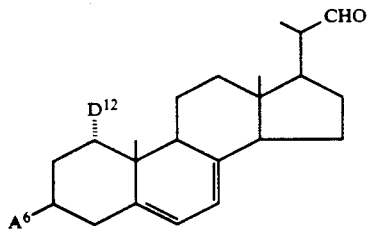

wherein $A^6$ is in the $\beta$-configuration and represents a hydroxyl group, an acyloxy group, a lower alkoxycarbonyloxy group, an N-lower alkylcarbamoyloxy group, an N-arylcarbamoyloxy group, an N,N-di(lower alkyl)-carbamoyloxy group, a tri-lower alkyl or phenyl substituted silyloxy group, an alkoxymethoxy group or an alkoxymethoxy group substituted by methoxy; $D^{12}$ is in the $\alpha$-configuration and represents a hydroxyl group, an acyloxy group, a lower alkoxycarbonyloxy group, an N-lower alkylcarbamoyloxy group, an N-arylcarbamoyloxy group, an N,N-di(lower alkyl)carbamoyloxy group, a tri-lower alkyl or phenyl substituted silyloxy group, an alkoxy methoxy group or an alkoxymethoxy substituted by methoxy.

7. The pregnane derivative of claim 1, which has the formula

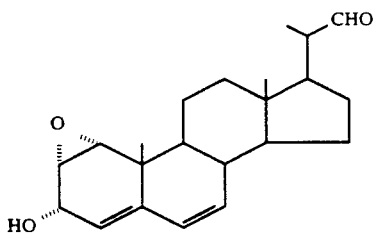

8. The pregnane derivative of claim 1, which has the formula

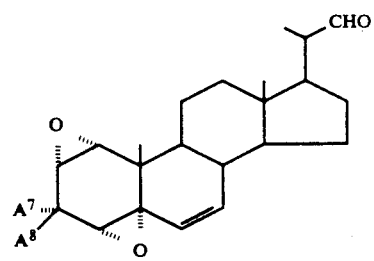

wherein $A^7$ is in the $\alpha$-configuration and represents a hydrogen atom or a hydroxyl group, and $A^8$ is such that where $A^7$ is a hydrogen atom in the $\alpha$-configuration, $A^8$ is in the $\beta$-configuration and represents a hydroxyl group, an acyloxy group, a lower alkoxycarbonyloxy group, an N-lower alkylcarbamoyloxy group, an N-aryl-carbamoyloxy group, an N,N-di(lower alkyl)carbamoyloxy group, a tri-lower alkyl or phenyl substituted silyloxy group, an alkoxy-methoxy group or an alkoxymethoxy group substituted by methoxy and where $A^7$ is a hydroxyl group in the $\alpha$-configuration, $A^8$ is in the $\beta$-configuration and represents a hydrogen atom, or $A^7$ and $A^8$ jointly represent an oxo group (=O).

9. The pregnane derivative of claim 1, which has the formula

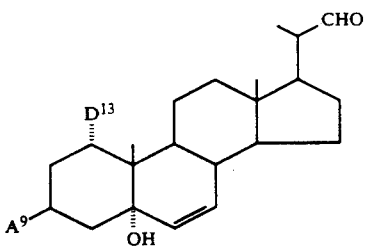

wherein $A^9$ is in the $\beta$-configuration and represents a hydroxyl group, an acyloxy group, a lower alkoxycarbonyloxy group, an N-lower alkylcarbamoxloxy group, an N-arylcarbamoyloxy group, an N,N-di(lower alkyl)-carbamoyloxy group, a tri-lower alkyl or phenyl substituted silyloxy group, an alkoxymethoxy group or an alkoxymethoxy group substituted by methoxy; $D^{13}$ is in the $\alpha$-configuration and represents a hydroxyl group, an acyloxy group, a lower alkoxycarbonyloxy group, an N-lower alkylcarbamoyloxy group, an N-arylcarbamoyloxy group, an N,N-di(lower alkyl)-carbamoyloxy group, a tri-lower alkyl or phenyl substituted silyloxy group, an alkoxymethoxy group or an alkoxymethoxy group substituted by methoxy.

10. The pregnane derivative of claim 1, which has the formula

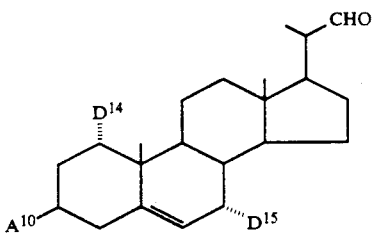

wherein $A^{10}$ is in the $\beta$-configuration and represents a hydroxyl group, an acyloxy group, a lower alkoxycarbonyloxy group, an N-lower alkylcarbamoxloxy group, an N-arylcarbamoyloxy group, an N,N-di(lower alkyl)-carbamoyloxy group, a tri-lower alkyl or phenyl substituted silyloxy group, an alkoxymethoxy group or an alkoxymethoxy group substituted by methoxy; $D^{14}$ is in the $\alpha$-configuration and represents a hydroxyl group, an acyloxy group, a lower alkoxycarbonyloxy group, an N-lower alkylcarbamoyloxy group, an N-arylcarbamoyloxy group, an N,N-di(lower alkyl)carbamoyloxy group, a tri-lower alkyl or phenyl substituted silyloxy group, an alkoxymethoxy group or an alkoxymethoxy group substituted by methoxy; $D^{15}$ is the $\alpha$-configuration and represents a hydroxyl group, an acyloxy group, a lower alkoxycarbonyloxy group, an N-lower alkylcarbamoyloxy group, an N-arylcarbamoyloxy group or an N,N-di(lower alkyl)carbamoyloxy group.

* * * * *